US011154634B1

(12) United States Patent
Sims, Jr. et al.

(10) Patent No.: US 11,154,634 B1
(45) Date of Patent: Oct. 26, 2021

(54) ULTRAVIOLET LIGHT FIXTURE

(71) Applicants: Dewey McKinley Sims, Jr., Royal Oak, MI (US); Dewey McKinley Sims, III, Berkley, MI (US)

(72) Inventors: Dewey McKinley Sims, Jr., Royal Oak, MI (US); Dewey McKinley Sims, III, Berkley, MI (US)

(73) Assignee: McKinley Sims Holdings LLC, Berkley, MI (US)

( * ) Notice: Subject to any disclaimer, the term of this patent is extended or adjusted under 35 U.S.C. 154(b) by 0 days.

(21) Appl. No.: 17/140,060

(22) Filed: Jan. 2, 2021

(51) Int. Cl.

| | |
|---|---|
| *A61L 9/20* | (2006.01) |
| *F21S 8/04* | (2006.01) |
| *F21V 11/02* | (2006.01) |

(52) U.S. Cl.
CPC . *A61L 9/20* (2013.01); *F21S 8/04* (2013.01); *F21V 11/02* (2013.01); *A61L 2209/12* (2013.01)

(58) Field of Classification Search
None
See application file for complete search history.

(56) References Cited

U.S. PATENT DOCUMENTS

| | | | | |
|---|---|---|---|---|
| 2,569,772 A * | 10/1951 | Olsen | A61N 5/06 362/217.03 |
| 3,860,903 A * | 1/1975 | Van Steenhoven | F21V 11/04 362/279 |
| 4,422,824 A * | 12/1983 | Eisenhardt, Jr. | F04D 25/088 416/146 R |
| 4,596,935 A | 6/1986 | Lumpp | |
| 5,600,456 A * | 2/1997 | Maruyama | G02F 1/133526 349/64 |
| 6,497,840 B1 | 12/2002 | Palestro et al. | |
| 6,656,424 B1 * | 12/2003 | Deal | A61L 2/10 250/455.11 |
| 6,805,733 B2 | 10/2004 | Engel et al. | |
| 7,922,351 B2 | 4/2011 | Welker | |
| 8,080,203 B2 * | 12/2011 | First | A61L 9/20 422/24 |
| 8,350,228 B2 | 1/2013 | Welker | |
| 8,439,517 B2 | 5/2013 | Welker | |

(Continued)

OTHER PUBLICATIONS

Product: VidaShield UV24; Website: https://vidashield.com; Company: Medical Illumination.

*Primary Examiner* — Andrew Smyth
(74) *Attorney, Agent, or Firm* — Mastrogiacomo PLLC; Patrick Mastrogiacomo, Jr.

(57) ABSTRACT

An ultraviolet-C light fixture is provided, the ultraviolet-C light fixture comprising at least one ultraviolet-C light bulb to sterilize an air flow, an ultraviolet-C radiation field created by the at least one ultraviolet-C light bulb to sterilize the air flow, a top end cap, a base and a plurality of louvers, the plurality of louvers positioned proximate one another, the top end cap and the base to create a gap, the gap sized to allow ultraviolet radiation to pass outside the ultraviolet light fixture to create a sterilization field outside the ultraviolet light fixture to eradicate bacterial, viral or pathogen particles from the air flow surrounding the fixture and the gap sized to allow passage of the air flow containing a cloud of infectious bacterial, viral or pathogen particles to pass through a sterilization chamber within the ultraviolet light fixture to eradicate bacterial, viral or pathogen particles from the air flow.

17 Claims, 49 Drawing Sheets

(56) References Cited

U.S. PATENT DOCUMENTS

| | | | | |
|---|---|---|---|---|
| 8,921,813 | B2* | 12/2014 | Palmer | F21V 7/005 |
| | | | | 250/504 R |
| 9,358,313 | B2 | 6/2016 | Deal | |
| 10,603,394 | B2 | 3/2020 | Farren et al. | |
| 10,753,626 | B2* | 8/2020 | Skelton | F24F 3/16 |
| 2006/0159594 | A1* | 7/2006 | Parker | H01J 61/35 |
| | | | | 422/121 |
| 2006/0177356 | A1* | 8/2006 | Miller | A61M 11/06 |
| | | | | 422/121 |
| 2007/0057197 | A1* | 3/2007 | Chor | A61L 2/10 |
| | | | | 250/455.11 |
| 2009/0117000 | A1* | 5/2009 | First | A61L 9/20 |
| | | | | 422/24 |
| 2009/0129974 | A1* | 5/2009 | McEllen | F04D 25/088 |
| | | | | 422/24 |
| 2010/0143205 | A1* | 6/2010 | Engelhard | A61L 9/205 |
| | | | | 422/121 |
| 2010/0260644 | A1* | 10/2010 | Day | A61L 9/205 |
| | | | | 422/121 |
| 2014/0026467 | A1* | 1/2014 | Kaye | A01M 1/145 |
| | | | | 43/113 |
| 2016/0175475 | A1* | 6/2016 | DuPuis | A61L 9/20 |
| | | | | 250/432 R |
| 2017/0007736 | A1* | 1/2017 | Engelhard | B01D 53/8675 |
| 2017/0080373 | A1* | 3/2017 | Engelhard | B01D 46/442 |
| 2018/0056758 | A1* | 3/2018 | Salter | B60H 3/0078 |
| 2019/0219284 | A1* | 7/2019 | Skelton | F24F 3/16 |
| 2019/0240370 | A1* | 8/2019 | Benedek | A61L 9/122 |
| 2019/0240371 | A1* | 8/2019 | Benedek | B01D 46/0028 |
| 2020/0297890 | A1* | 9/2020 | Skelton | A61L 9/20 |
| 2020/0324012 | A1* | 10/2020 | Skelton | G01P 13/00 |

* cited by examiner 16.0 seconds after start of cough
5 inches/second horizontal air flow due to HVAC Air Flow

HVAC

Individual A
Infected

Individual B
Exposed

Cloud of Infectious Particles

Individual C
Exposed

Individual D

FIG. 1E

Cloud 136 of
Infectious Particles

FIG. 2B

UV-C Intensity at Distance from
Center of Bulb
(mW per cm^2)

| Distance from UV-C Lamp (inch) | UV-C Intensity at a given distance (mW/cm^2) | Disinfection Time (sec) | % Disinfection for Air Flow @ 5 in / sec for 1 inch of travel |
|---|---|---|---|
| 1 | 405,000 | 0.099 | 202.50% |
| 2 | 101,250 | 0.395 | 50.63% |
| 3 | 45,000 | 0.889 | 22.50% |
| 4 | 25,313 | 1.580 | 12.66% |
| 5 | 16,200 | 2.469 | 8.10% |
| 6 | 11,250 | 3.556 | 5.63% |
| 7 | 8,265 | 4.840 | 4.13% |
| 8 | 6,328 | 6.321 | 3.16% |
| 9 | 5,000 | 8.000 | 2.50% |
| 10 | 4,050 | 9.877 | 2.03% |
| 11 | 3,347 | 11.951 | 1.67% |
| 12 | 2,813 | 14.222 | 1.41% |
| 13 | 2,396 | 16.691 | 1.20% |
| 14 | 2,066 | 19.358 | 1.03% |
| 15 | 1,800 | 22.222 | 0.90% |
| 16 | 1,582 | 25.284 | 0.79% |
| 17 | 1,401 | 28.543 | 0.70% |
| 18 | 1,250 | 32.000 | 0.63% |
| 19 | 1,122 | 35.654 | 0.56% |

FIG. 25

ULTRAVIOLET LIGHT FIXTURE

CROSS REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON COMPACT DISC

Not Applicable

BACKGROUND OF THE INVENTION

1. Field of the Invention

The present invention relates generally to a light fixture and, more particularly, to a light fixture that incorporates an ultraviolet light source and safety features that enable the use of the ultraviolet light source to kill airborne bacteria, viruses and pathogens that are harmful to humans and animals while humans and animals are present during the operation of the ultraviolet light.

2. Background Art

A threat to the respiratory systems of humans and animals is the Severe Acute Respiratory Syndrome Coronavirus 2 (SARS-CoV-2) virus and subsequent Coronavirus Disease (COVID-19). One means of transmitting the SARS-CoV-2 virus is by exposing or passing infectious viral particles in aerosols or water droplets from one individual to other individuals within the same enclosed area. Examples or an enclosed area may be an indoor restaurant, a working manufacturing plant or a conference room in an office building. A single infected individual may transmit the infectious viral particles to other healthy individuals through breathing, talking, yelling, singing, coughing and/or sneezing within the enclosed area. The healthy individuals merely need to have their mouth, nose or eyes in the pathway of the cloud or aerosol of infectious viral particles contained in water droplets produced by the infected individual to have the infected particles enter into a healthy individual.

As stated above, the infectious viral particles may be released into the environment by a single infected individual through breathing, talking, yelling, singing, coughing and/or sneezing within the enclosed area. However, the different aspects of expelling the viral particles may be done so in drastically different amounts of the viral particles and at varying speeds of expulsion. A single sneeze releases about 30,000 droplets that may contain the infectious viral particles at about 200 miles per hour. A SARS-CoV-2 virus cloud created by the single sneeze may move about 20 inches in 0.3 seconds. After the initial virus cloud is created by the single sneeze, the cloud will move at the speed of the air flow in the room. If there is little to no air flow in the room, the virus cloud will grow in size and remain infectious for hours. Many droplets are small and may travel great distances, easily across and filling an enclosed room in a few minutes.

A single cough releases about 3,000 droplets that may contain the infectious viral particles at about 50 miles per hour. A SARS-CoV-2 virus cloud created by the single cough may move about 20 inches in 0.3 seconds. After the initial virus cloud is created by the single cough, the cloud will move at the speed of the air flow in the room (see FIGS. 1A-1F for an illustration on how the infectious cloud of viral particles may move across a room while expanding exposing several individuals to the SARS-CoV-2 virus). If there is little to no air flow in the room, the virus cloud will grow in size and remain infectious for hours. Many droplets are large and fall quickly to the ground under the force of gravity, but many do stay in the air and may travel across an enclosed room in a few minutes.

A single breath releases 50 to 5000 droplets that may contain the infectious viral particles, but they are expelled at a very low velocity and fall to the ground quickly under the force of gravity. Unlike sneezing and coughing which release a large amount of viral material due to the exhalation force of a sneeze or cough, breathing droplets will contain less of the viral material due to a lower exhalation force. Talking increases the release of droplets about ten-fold and singing even more. There is a large amount of infectious viral material that can be introduced into an enclosed area through normal human actions that can easily fill an enclosed area. Traditional building ventilation systems with typical filtering capability merely help to fill an enclosed area with the infectious viral particles faster and may increase the chances of other individuals contracting the infection and causing the exponential spread of the SARS-CoV-2 virus.

Means have been developed to interrupt the path of the aerosol of infectious viral particles. Many stores and places of business that deal with the public on a daily basis have installed a plexiglass barrier to prevent any infectious viral particles from passing from an infected person to the individual on the other side of the plexiglass barrier. The plexiglass barrier stops the path of the infectious viral particles from reaching the individual behind the barrier. As the infectious person stands in front of the plexiglass barrier for several minutes, the individual could be creating a large cloud of infectious viral particles though breathing, talking, yelling, singing, coughing and/or sneezing within the enclosed area. As the next person in line moves forward, they will move into the cloud of infectious viral particles and increase their chances of becoming infected. The cloud of viral particles may remain infectious for several hours. If there is little to no air flow to move the cloud, the cloud of infectious viral particles may remain to infect several individuals as they move through the cloud. Further, while the plexiglass barrier stands in the path of the infectious viral particles, the viral particles have been deposited onto the surface of the plexiglass barrier. The plexiglass barrier requires a thorough cleaning with cleaners and disinfectants to adequately kill the virus. Still further, there is nothing to prevent other individuals in line from the pathway of the viral particles or touching the plexiglass surface and then their own mouth, nose or eyes and contracting the infection.

Masks and shields are other means to slow the transmission of the infectious viral particles from person to person. Masks covering the mouth and nose area are an effective means to prevent transmission of the viral particles by mouth or nose, but the mask does not cover the eyes. Shields adequately cover the eyes, nose and mouth, but may not be practical for everyday use. Further, all individuals may not be wearing masks or shields and even if they are being worn, they may not be worn correctly or people may continue to touch their eyes, mouth or nose with hands and fingers that may be infected with the infectious viral particles while adjusting the mask or shield. There have been several reports that a community choir group sang for 2.5 hours in a hall roughly the size of a volley ball court. The participants avoided the usual personal contact (handshakes, hugs, etc.) and they brought their own music to avoid sharing. The participants also social distanced themselves during practice. A single asymptomatic carrier infected 45 of the 60 choir members and two dies. Some of the participants that were infected were approximately 50 feet from the infected person.

Many are practicing social distancing by maintaining a distance of six feet from one another and limiting the number of individuals in an enclosed room. But, as described above, a single infected person may fill a room or even infect a socially distanced person with infectious viral material with a single sneeze.

Others may be shutting down their ventilation systems to limit the flow of aerosols of infectious viral particles in an enclosed room and even opening windows to allow fresh outside air into an enclosed room to dilute the cloud of infectious viral material. However, as the weather changes and heating and air conditioning is required for the comfort of the individuals in the enclosed room, ventilation system will have to be reactivated and windows closed.

Many of the above actions are being put in place in an effort to open restaurants, business and schools. However, as stated above, there are many drawbacks to these efforts to protect individuals from coming into contact with SARS-CoV-2 virus. If one examines the individual protections being proposed for schools as an example, one will quickly determine that the protections have serious drawbacks. All students and faculty will be required to wear masks or face coverings of some type as well as maintain social distancing at the requisite distance. There are several issues with this proposal. First, wearing a mask may greatly interfere with communication between the teacher and students and between the students themselves. If the communication between teacher and students is impacted negatively, both teach and students will become frustrated to a point where learning will be impacted negatively. Even worse, a teacher may remove their mask to communicate better with the students. An unmasked infected teacher may become a super spreader of the disease. An infected teacher speaking loudly for several hours may fill a classroom with many clouds of infectious viral particles in little time. Students wearing masks will still be subject to the infectious viral material contained in the room. Infectious viral particles smaller than 5 microns will pass through any mask that is not N95 certified. Even if N95 masks are required by schools, the exterior surface of the mask or any type of face covering will be contaminated with infectious viral particles. Students may touch the exterior surface when removing the mask (at the end of the day, eating lunch, etc.) or adjusting the mask with their fingers and then touch their eyes, nose or mouth thereby subjecting themselves to potential infection. Further, the cost of replacing the mask every few days is expensive and still further, there may be a shortage of masks to provide to school children and others working in a public business. Prolonged mask usage may cause hypercapnia, a condition arising from too much carbon dioxide in the blood. Symptoms of hypercapnia include dizziness, drowsiness, fatigue, headaches, felling disorientated, flushing of the skin, shortness of breath, increased heart rate and increased blood pressure (N95 masks reduce oxygen intake by approximately 5% to 20%). If one were to wear a mask long enough, it may damage the lungs. For a patient in respiratory distress, wearing a mask for a prolonged period of time may be life threatening. Students wearing face shields may alleviate the breathing issues of wearing a mask, but many of the issues discussed above, will not be improved.

Students and teachers will practice social distancing. A typical desk in a classroom is approximately two feet from a neighboring desk. This allows for a classroom to house approximately 30-35 desks depending on the size of the classroom. Social distancing dictates that there must be at least six feet between individuals. With that requirement, the number of desks and, therefore, students will be reduced to approximately 8-9 in the classroom. The other 22-26 students will have to be relocated into at least three other classrooms thereby requiring more classrooms and teachers.

Another proposal to keep students and faculty safe from the transmission of the SARS-CoV-2 virus is to add transparent plastic or plexiglass barriers between teacher and students and between students. The plastic barriers may greatly interfere with communication between the teacher and students and between the students themselves. If the communication between teacher and students is impacted negatively, both teach and students will become frustrated to a point where learning will be impacted negatively. Further, it will be difficult to move around the classroom for the teacher and the students especially if they all had to exit the classroom quickly due to an emergency. The plastic barriers would be a costly solution and the space required to position the barriers between desks within the classroom would reduce the number of desks and students in the room. As discussed above the plastic barriers may become contaminated with infectious viral particles and would require daily cleaning to remove any particles. Students and teachers may still face the possibility of infection either by existing infectious clouds of viral particles that are in the room or the viral particles present on the plastic barriers.

Still another proposal is to transform a traditional classroom into a clean room much like that of a hospital operating room. A drop ceiling may be installed in each class room with the ceiling including a plurality of high-efficiency particulate absorbing (HEPA) filters to trap the SARS-CoV-2 virus particles. Clean air may be forced downward from the ceiling driving any infectious viral particles out of the ingestion zone of students' mouth, nose and eyes and downward to the floor. The air and infectious viral particles at the floor may be forced to the walls of the clean room and sent through the gap between the walls of the clean room and the classroom back to the drop ceiling and the HEPA filters to filter out the infectious viral particles and return clean air to the room. There are several drawbacks with this proposal. The size of the clean room would still limit the number of desks and therefore students in the room. Creating a clean room will be costly and HEPA filters must be changed on a regular basis which may also be quite expensive. Further, there is a risk that those changing the filters may become infected just by handling the filters and infectious viral particles. Lastly, a continual source of HEPA filters would have to be developed to accommodate all schools and business and it may take several years to outfit and construct clean rooms for all schools and businesses.

The use of ultraviolet-C or UV-C light is well known for its use a disinfectant. The Centers for Disease Control ("CDC") "verifies that UV-C light germicidal irradiation has been employed in the disinfection of drinking water, air, titanium implants, contact lens and the healthcare environment (i.e., operating rooms, isolation rooms, and biological safety cabinets) for both destruction of airborne organisms or inactivation of microorganisms on surfaces." (from Centers for Disease Control—Infection Control https:// www.cdc.gov). UV-C light can be adapted for use in commercial and residential buildings globally along with the ventilation system of the building to eradicate airborne viruses and bacteria including coronaviruses such as SARS-CoV-2 which causes COVID19. UV-C light in the 254 nm wavelength inactivates coronaviruses by damaging their DNA and RNA genetic material. (from Centers for Disease Control https://www.cdc.gov and Food & Drug Administration https://www.fda.gov).

Several prior art references discuss the benefits of UV-C for the eradication of airborne pathogens, viruses and bacteria. U.S. Pat. No. 2,569,772 entitled "Germicidal Lamp Mounting and Reflector" issued to Olsen requires a UV-C lamp to be held in a horizontal position. Every point along the axis of the lamp emits radiation in a 360-degree plan normal to the axis of the lamp. The desired effect of the invention is to have the UV-C radiation travel outward and away from the UV-C lamp in a horizontal plane. The invention calls for the use of parabolic reflectors to direct the UV-C radiation into a horizontal plane for use in disinfecting a particular area. Of the 360-degree output of the lamp, about 260-degrees of the output is redirected into a horizontal plane for use in disinfecting the area. The reflectance off the reflectors is approximately 70% which, in turn, means approximately 22% of the total output of the lamp, the total UV-C radiation, is lost or wasted due to reflectance. Further, of the 100-degrees of radiation that is not reflected off the parabolic reflectors, approximately 98% of that radiation is absorbed by the louvers and shields of the invention leading to additional wasted energy of approximately 27% which results in a total loss of unusable radiation of approximately 49%. Almost half of the UV-C radiation is ineffective for disinfecting the area.

Another drawback of the present invention is that air will not flow through the fixture, meaning that the high intensity radiation near the source of the UV-C radiation is not being used for disinfecting the air. Only the air flowing away from the fixture and passing through the UV-C radiation in front of the fixture is being disinfected. As is known in the art, the intensity of the UV-C radiation decreases by the square of the distance from the UV-C source or lamp. The distance the radiation travels from the lamp to the outer edges of the fixture is about 6 inches. Therefore, the intensity of the radiation exiting the lamp may be reduced by a factor of 36 times thereby resulting in a significant reduction in the quality of disinfection the fixture can produce.

U.S. Pat. No. 6,656,424 entitled "Ultraviolet Area Sterilizer And Method Of Area Sterilization Using Ultraviolet Radiation" issued to Deal discloses a UV-C Sterilizer for use in disinfecting a room. The drawback with this particular invention is the requirement that all human and animals must be out of the room or building during the disinfection process due to the harmful UV-C light to humans and animals. Furthermore, disinfection only occurs when the invention is deployed into a room. If an individual carries harmful pathogens, viruses or bacteria into a room, the room will become infected along with the potential to infect others in the room before the room can be disinfected with UV-C light. U.S. Pat. No. 9,358,313 titled "Ultraviolet Radiation Emitting Fixture" also issued to Deal discloses a UV-C Light fixture for use in disinfecting a room. As described above in '424, the main drawback with this particular invention is the requirement that all human and animals must be out of the room or building during the disinfection process due to the harmful UV-C light to humans and animals. The same issues described above with a lack of continuous UV-C light eradication also apply to this invention as well.

UV-C light's germicidal effectiveness is influenced by UV intensity, which is affected by distance away from the UV-C light. (from Food & Drug Administration https://www.fda.gov). U.S. Pat. No. 8,921,813 entitled "Reflector For Ultraviolet Sterilizer Fixture" issued to Palmer et al. includes an elaborate system of parabolic reflectors and baffles to reflect the UV-C light laterally to protect the occupants of the room. The execution of the present invention is similar to the execution of the Olsen invention discussed above and is saddled with similar drawbacks. Typically, these units are attached at the wall to ensure the baffles extend laterally. A number of units and, therefore, expense, are required to ensure adequate UV-C light coverage to disinfect the air. Furthermore, as discussed above, the intensity of the UV-C radiation decreases the further away from the source the UV-C light must travel, thereby making it less likely the above invention would be capable of using UV-C to disinfect the center of a larger room.

Both the Palmer et al. and Olsen inventions rely on the use of parabolic reflectors to enable their respective inventions. Parabolic reflectors require very tight tolerances and the surface must be a highly polished metal such as aluminum or steel to ensure reflections which results in a very expensive component. Furthermore, the smallest error (approximately 1-degree to 2-degrees) in location of the parabolic reflectors or the location of the bulb may result in all the UV-C radiation produced by the lamp being absorbed into the fixture prior to having the opportunity to disinfect the area.

U.S. Pat. No. 8,080,203 entitled "Air Sterilization Apparatus" issued to First et al. discloses an air sterilization apparatus that may direct air across UV-C radiation field to sterilize the air. A baffle may also be provided to shield the eyes of occupants of the room form UV-C energy in the radiation field. In this particular invention, much of the UV-C radiation from the lamp (more than 290 degrees of the 360-degree output of the UV-C lamp) is absorbed by the baffle and the base resulting in approximately 80% of the output of the UV-C lamp being lost and wasted. Also, less than 10 degrees of the lamp output shines horizontally outward to disinfect the air. Further, the air approaching the fixture will not be disinfected and the air is not forced to flow into the fixture and around the UV-C bulb where the highest intensity UV-C radiation may be found.

United States Patent Application No. 2009/0129974 entitled "Air Quality Enhancing Ceiling Paddle Fan" issued to McEllen discloses a ceiling paddle fan fixture having a UV-C source to sterilize room air while the fixture is in use. Sterilization of room air is achieved by the passage of a high volume of air at a relatively slow speed through a relatively low intensity UV-C field. The main drawback with the McEllen disclosure is the small opening to allow air and light to pass through. The opening is between 10 degrees and 45 degrees. An opening of 10 degrees results in 350 degrees of the UV-C radiation from the lamp being absorbed by the fixture meaning the fixture is approximately 3% effective for eradication of any virus, bacteria or pathogen from the air near the lamp. An opening of 45 degrees increases the effectiveness of the UV-C radiation from the lamp to approximately 13%. This leads to a coverage area of approximately 50 square feet for a single fixture meaning a number of fixtures and expense will be required to sterilize the air in a large room.

U.S. Pat. No. 10,753,626 entitled "Air Treatment Unit" issued to Skelton discloses an air treatment unit having a UV light source configured to disinfect air. Air from a duct or within a space is directed into a volume that has UV light rays from the source of the UV lights therein capable of disinfecting air. The main disadvantage of this invention is the UV light leaving the source lamp is absorbed by the surface of the ceiling, the bottom wall and the edges of the louvers. Approximately 10 degrees of the 360-degree output of the UV lamp will pass through the spaces between the louvers meaning this fixture is about 3% effective at eradicating viruses, bacteria and pathogens from the air around the fixture leading to the need for a large number of fixtures, and, thus expense, to adequately sterilize the air in a room.

Therefore, a need exists for an inexpensive and practical ultraviolet light fixture that enables constant operation of the ultraviolet light within a room during the presence of humans and animals. A need also exists for a number of inexpensive fixtures to be deployed in an enclosed area such that the entire area may be covered with adequate ultraviolet radiation to disinfect the entire room while at the same time safely allowing the presence of humans and animals within the room during the disinfection process. Furthermore, a need exists for a highly effective ultraviolet light fixture that allows most of the ultraviolet radiation to travel outside the fixture to sterilize a large area with a minimal number of fixtures.

BRIEF SUMMARY OF THE INVENTION

An ultraviolet light fixture is provided, the ultraviolet light fixture comprising at least one ultraviolet light bulb to sterilize an air flow, an ultraviolet radiation field created by the at least one ultraviolet light bulb to sterilize the air flow, a top end cap, a base and a plurality of louvers, the plurality of louvers positioned proximate one another, the top end cap and the base to create a gap, the gap sized to allow ultraviolet radiation to pass outside the ultraviolet light fixture to create a sterilization field outside the ultraviolet light fixture to eradicate bacterial, viral or pathogen particles from the air flow surrounding the fixture and the gap sized to allow passage of the air flow containing a cloud of infectious bacterial, viral or pathogen particles to pass through a sterilization chamber within the ultraviolet light fixture to eradicate bacterial, viral or pathogen particles from the air flow.

BRIEF DESCRIPTION OF THE SEVERAL VIEWS OF THE DRAWINGS

The features and inventive aspects of the present invention will become more apparent from the following detailed description, claims, and drawings, of which the following is a brief description:

FIGS. 1A-1F are side views illustrating how a cloud of infectious viral particles may pass from an infected individual to expose subsequent individuals in a typical room under the operation of a typical heating, ventilation and air conditioning (HVAC) system with a horizontal air flow;

Figure 2B:
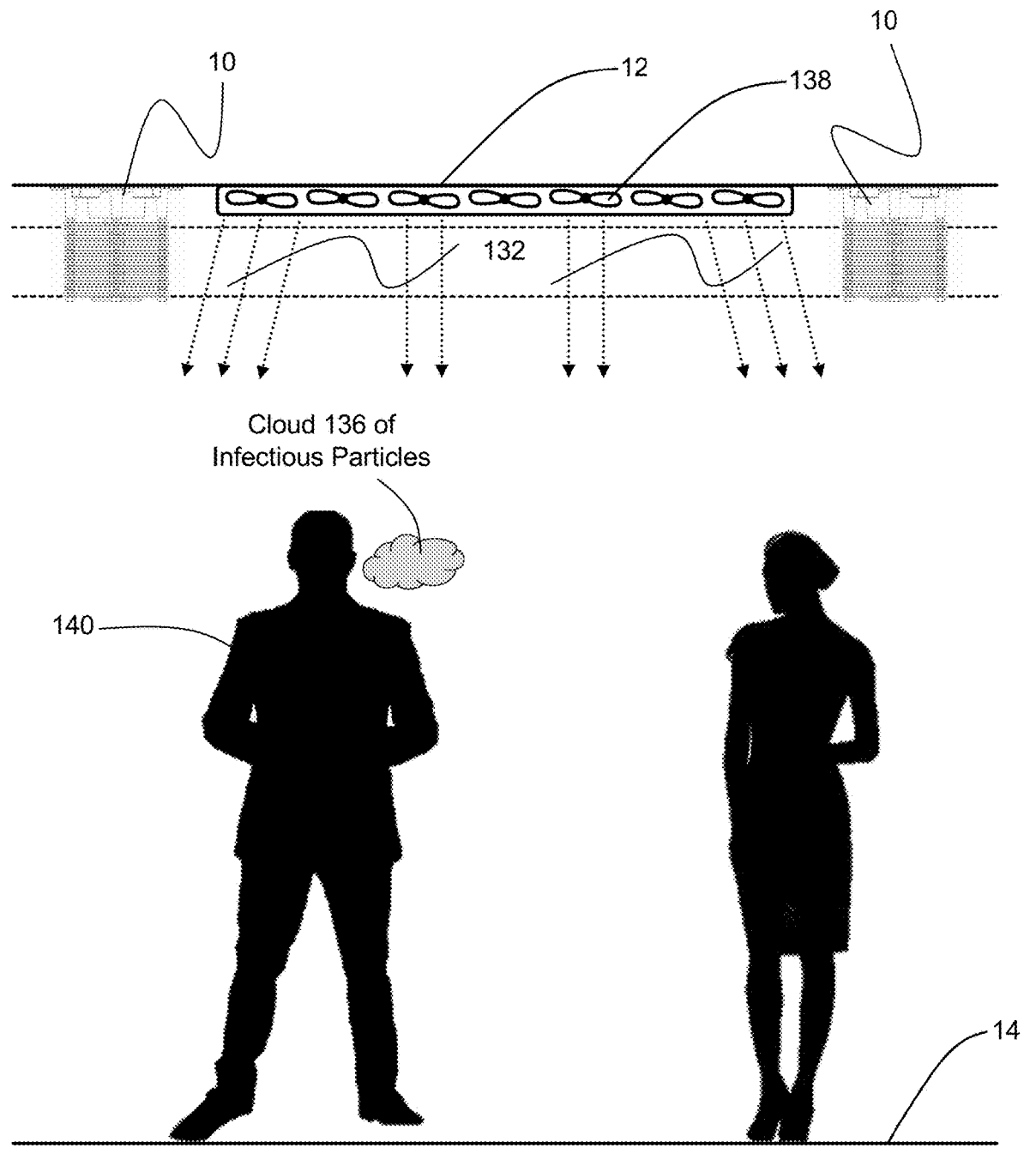

FIGS. 2A-2F are environmental views of a system of ultraviolet light fixtures according to an embodiment of the present invention shown deployed in a typical room to achieve maximum ultraviolet-C radiation exposure to eradicate pathogens, viral particles and bacteria in the room;

FIG. 3 is an isometric view of the ultraviolet light fixture according to the embodiment of the present invention;

FIG. 4 is a plan view of the ultraviolet light fixture according to the embodiment of the present invention;

FIG. 5 is a top view of the ultraviolet light fixture according to the embodiment of the present invention;

FIG. 6 is a bottom view of the ultraviolet light fixture according to the embodiment of the present invention;

FIG. 7A is a side view of a top end cap of the ultraviolet light fixture according to the embodiment of the present invention;

FIG. 7B is a cross-sectional view of a fastener seat and a female post of the top end cap of the ultraviolet light fixture according to the embodiment of the present invention;

FIG. 7C is an underside view of the top end cap of the ultraviolet light fixture according to the embodiment of the present invention;

FIG. 8A is a side view of a base of the ultraviolet light fixture according to the embodiment of the present invention;

FIG. 8B is a cross-sectional view of a pillar and a male peg of the base of the ultraviolet-C light fixture according to the embodiment of the present invention;

FIG. 8C is a top view of the base of the ultraviolet light fixture according to the embodiment of the present invention;

FIG. 9A is a side view of a mounting plate of the ultraviolet light fixture according to the embodiment of the present invention;

FIG. 9B is an underside view of the mounting plate of the ultraviolet light fixture according to the embodiment of the present invention;

FIG. 10A is a side view of a louver of the ultraviolet light fixture according to the embodiment of the present invention;

FIG. 10B is a cross-sectional view of a male peg and a female post of the louver of the ultraviolet light fixture according to the embodiment of the present invention;

FIG. 10C is a top view of the louver of the ultraviolet light fixture according to the embodiment of the present invention;

FIG. 10D is an underside view of the louver of the ultraviolet light fixture according to the embodiment of the present invention;

FIG. 11 is a plan view of a dowel of the ultraviolet light fixture according to the embodiment of the present invention;

FIG. 12 is a plan view of a light bulb of the ultraviolet light fixture according to the embodiment of the present invention;

FIG. 13 is a plan view of a light bulb base of the ultraviolet light fixture according to the embodiment of the present invention;

FIGS. 14A-14C are exploded views of the ultraviolet light fixture according to the embodiment of the present invention;

FIG. 14D is a cross-sectional view of the top end cap, the base, the louver and the dowel of the ultraviolet light fixture according to the embodiment of the present invention;

FIGS. 15A-15D are plan views of the ultraviolet light fixture according to the embodiment of the present invention depicting alternative means of mounting the light fixture within a structure;

FIGS. 16-20 are plan views of the ultraviolet light fixture configured to support the use of several sizes and types of ultraviolet bulbs and enable the adjustment of the intensity of ultraviolet-C radiation produced by the ultraviolet bulb;

FIG. 21A is an exploded view of an ultraviolet light fixture according to another embodiment of the present invention;

FIG. 21B is a plan view of the ultraviolet light fixture according to the embodiment of the present invention;

FIGS. 21C and 21D are cross-sectional views of the top end cap, the base, the louver, the dowel and a sleeve of the ultraviolet light fixture according to the embodiment of the present invention;

FIG. 25. is a table listing the change in intensity of ultraviolet light radiation at several distances from the center of the bulb according to an embodiment of the present invention.

DETAILED DESCRIPTION OF THE INVENTION

Figure 1A:
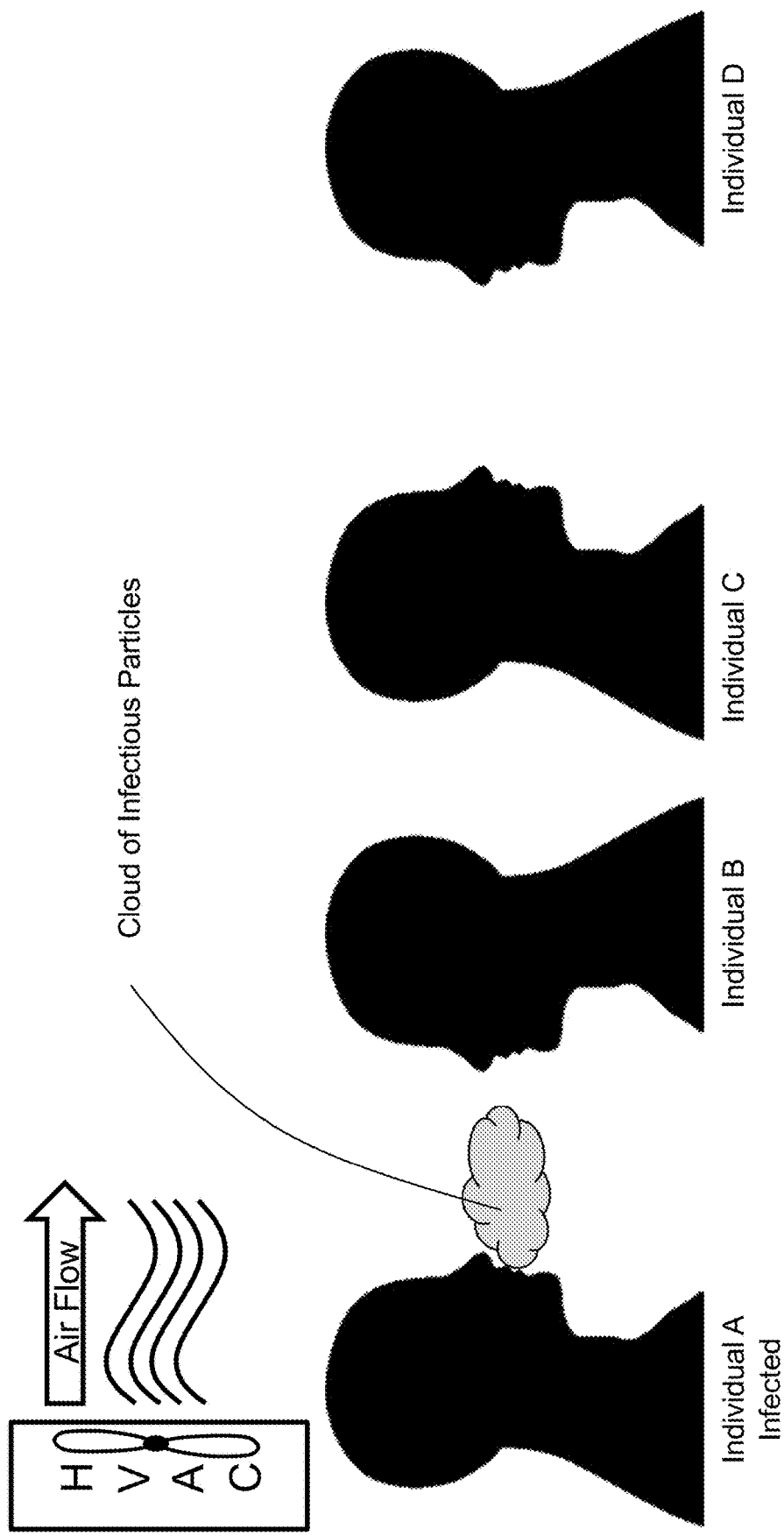
Figure 1B:
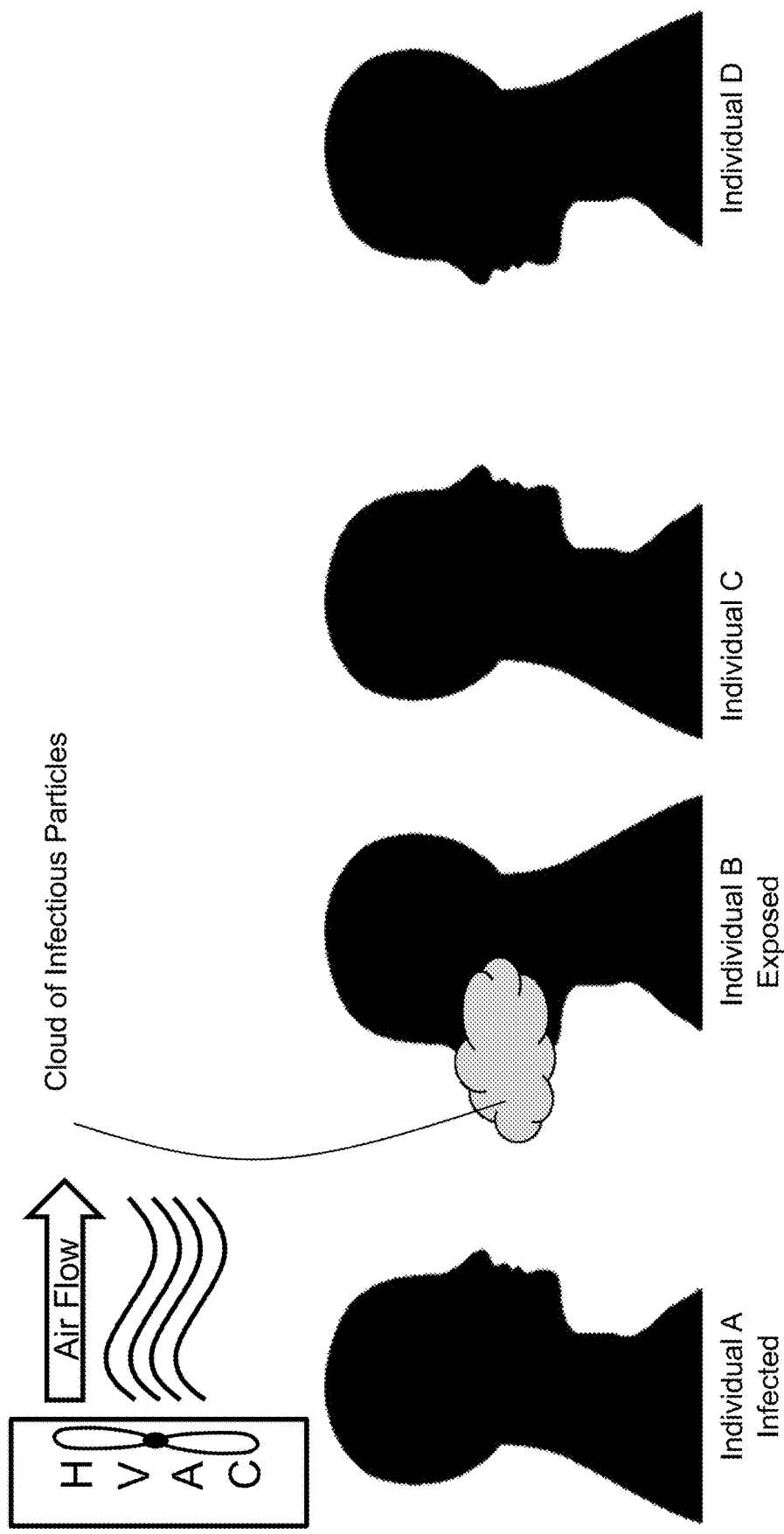
Figure 1C:
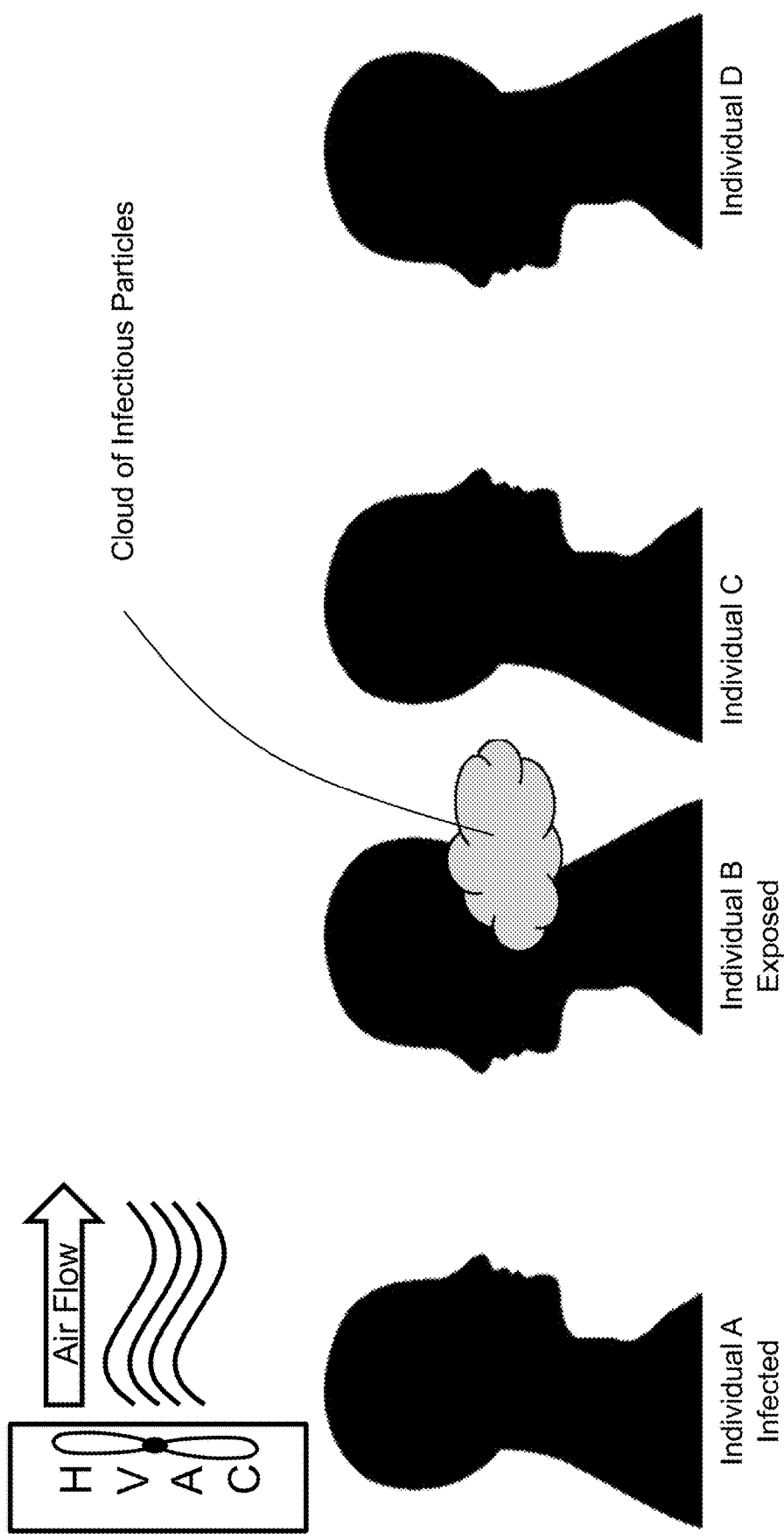
Figure 1D:
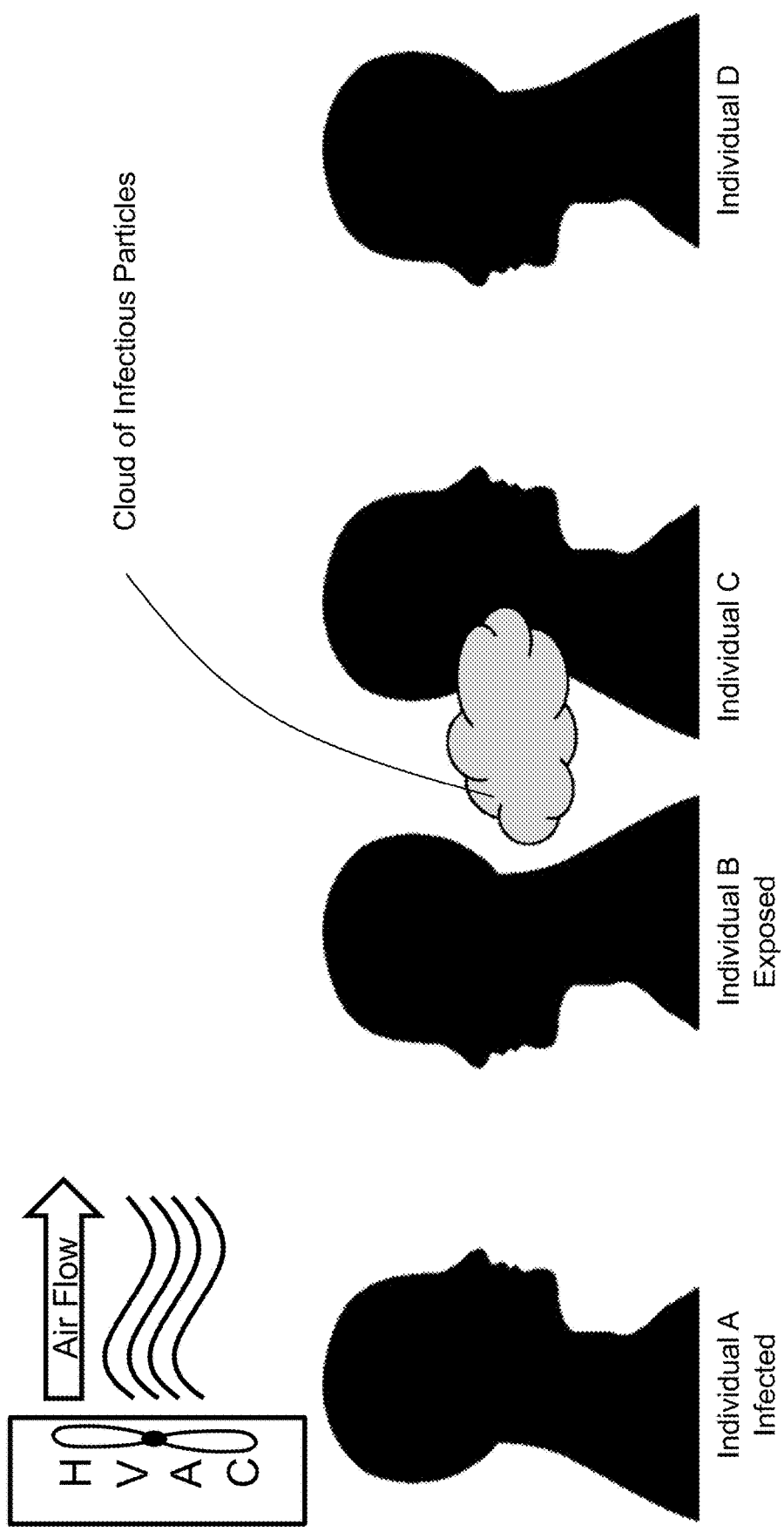
Figure 1F:
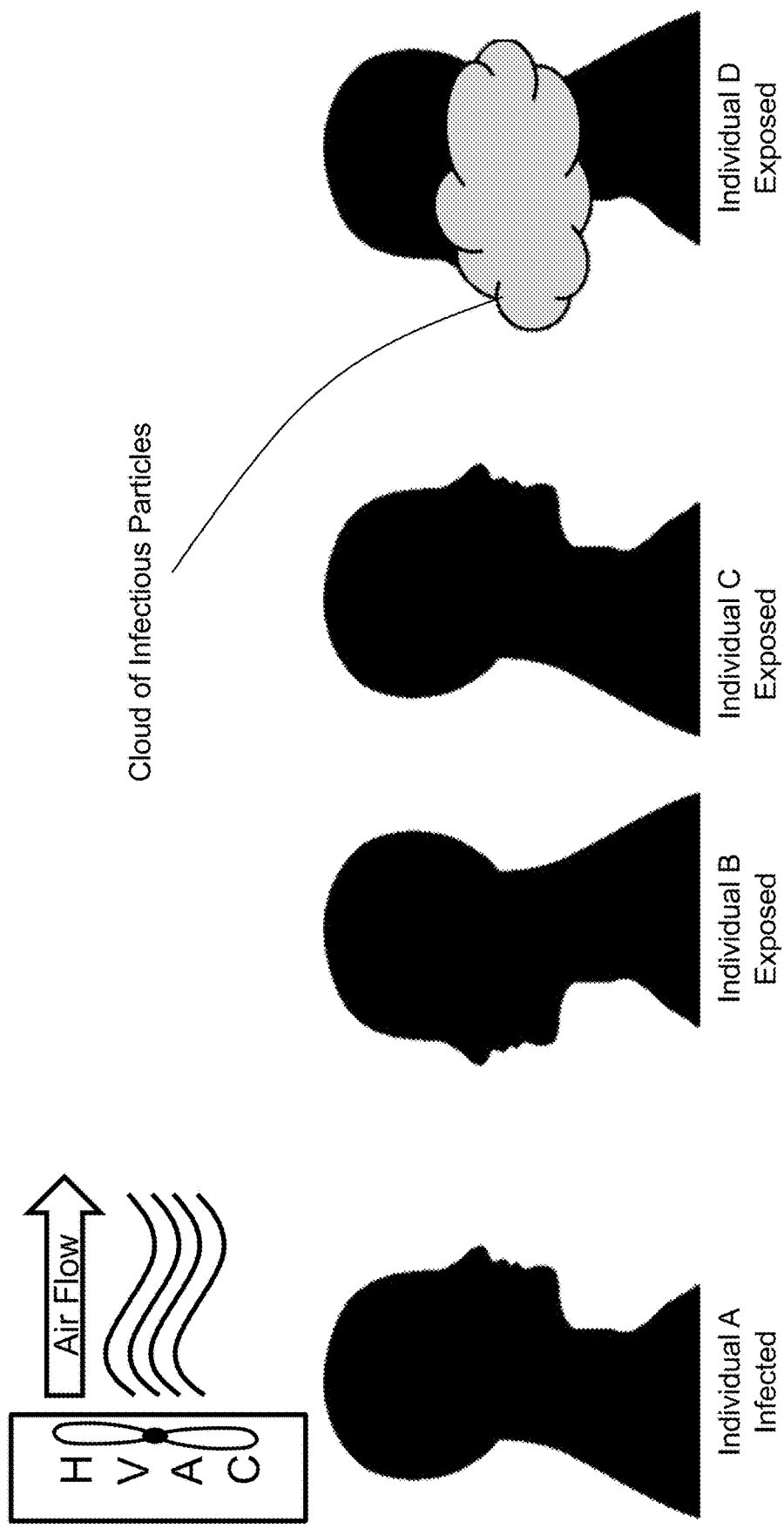
Figure 2A:
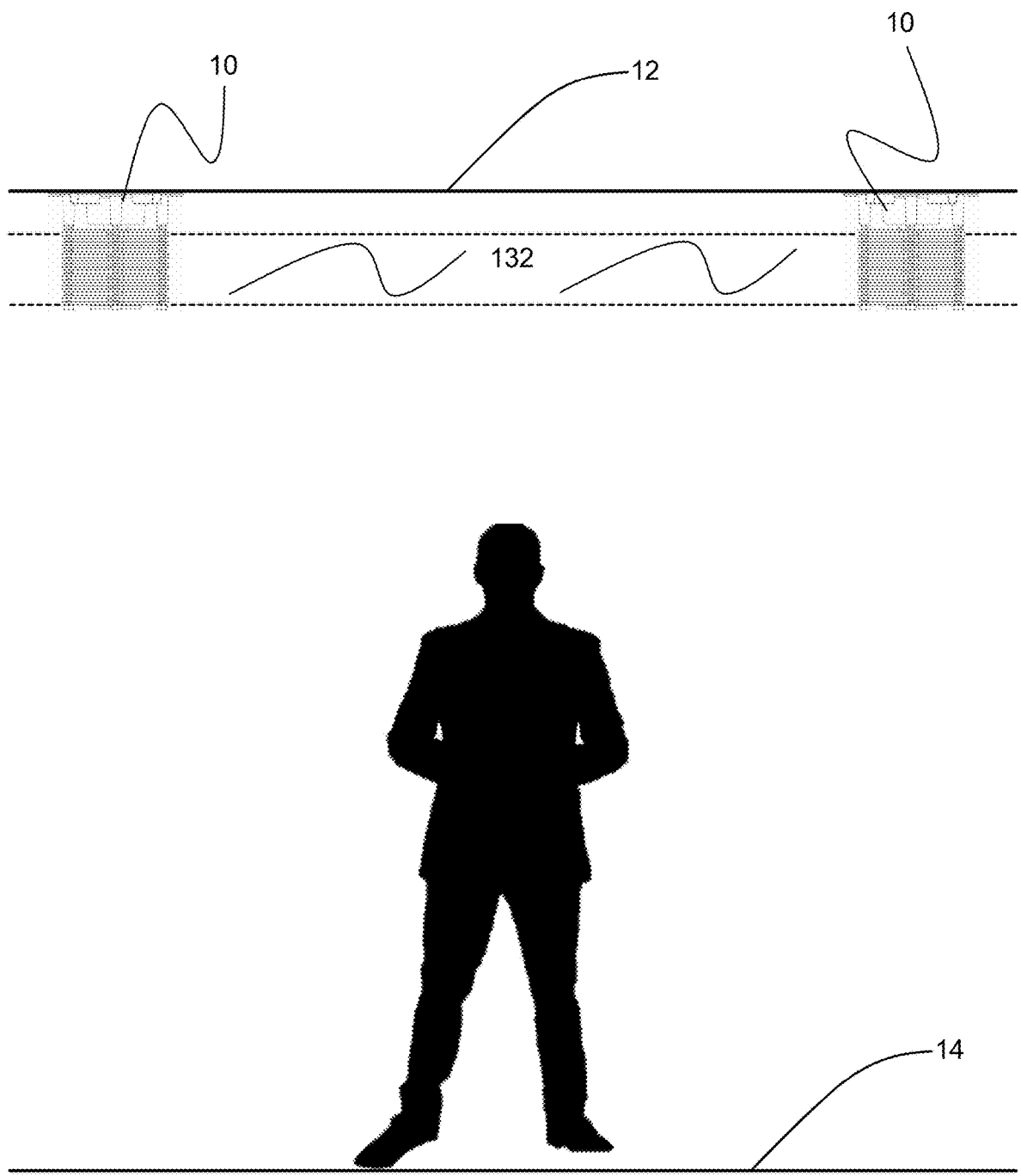
Figure 2C:
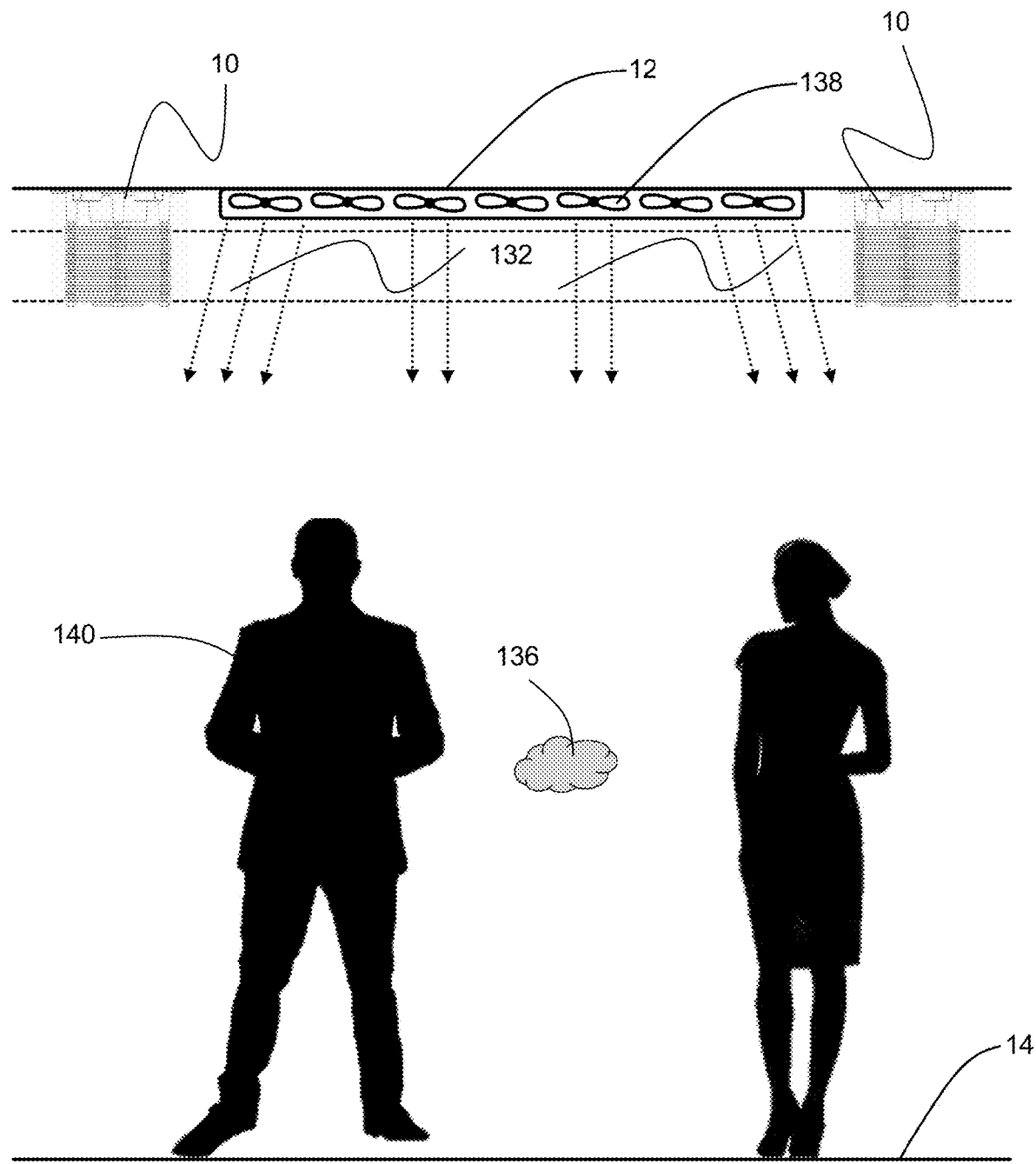
Figure 2D:
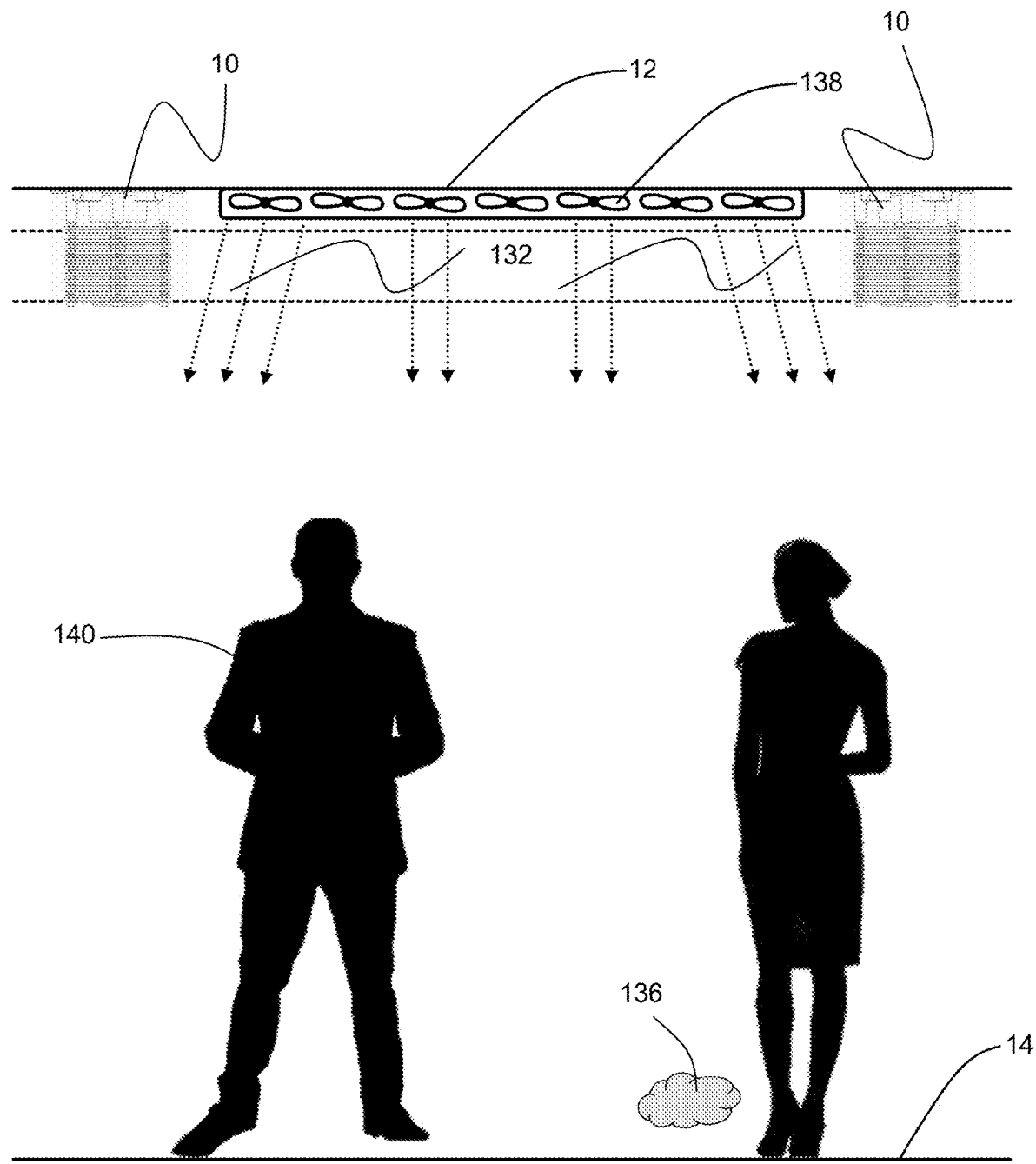
Figure 2E:
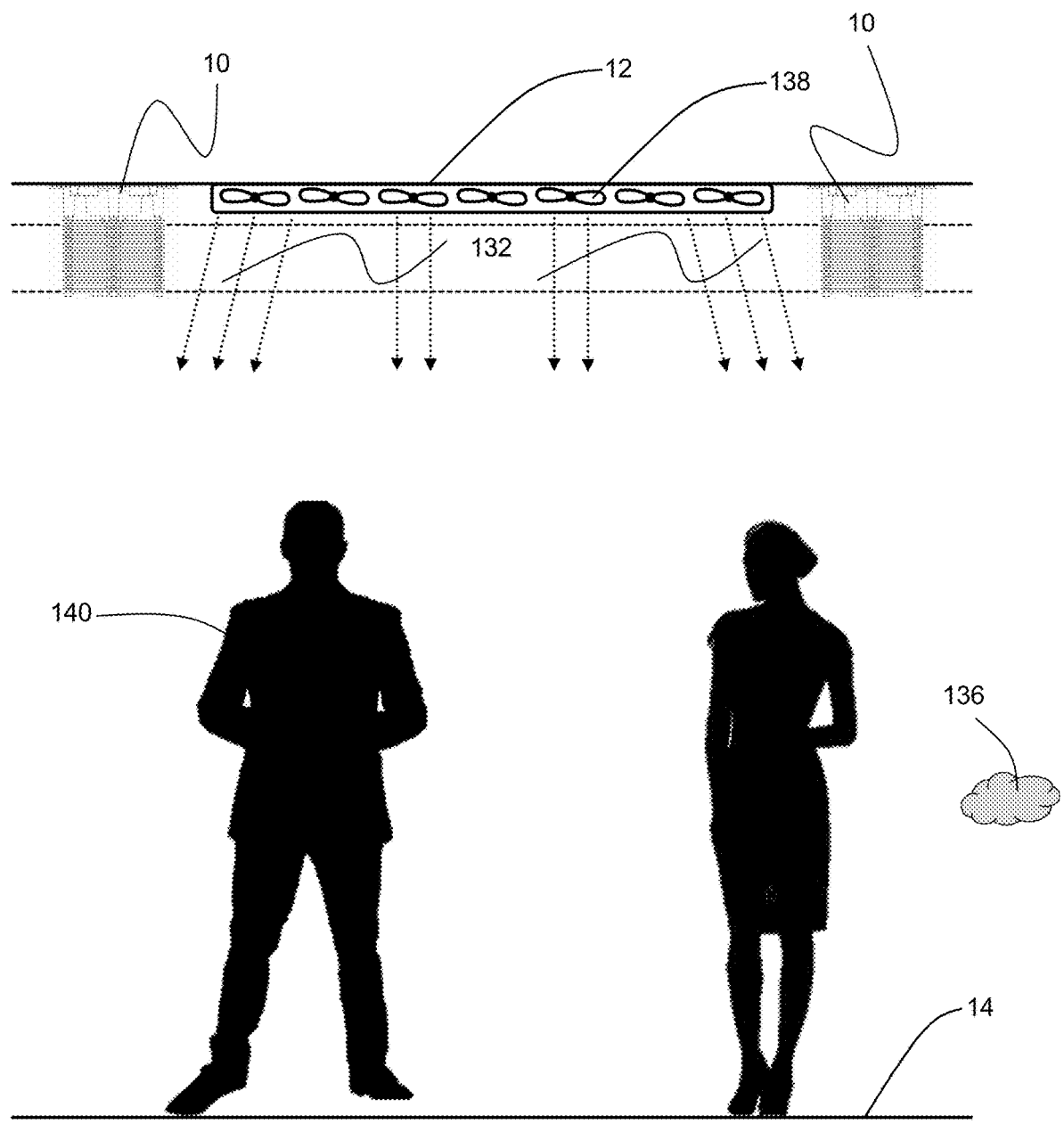
Figure 2F:
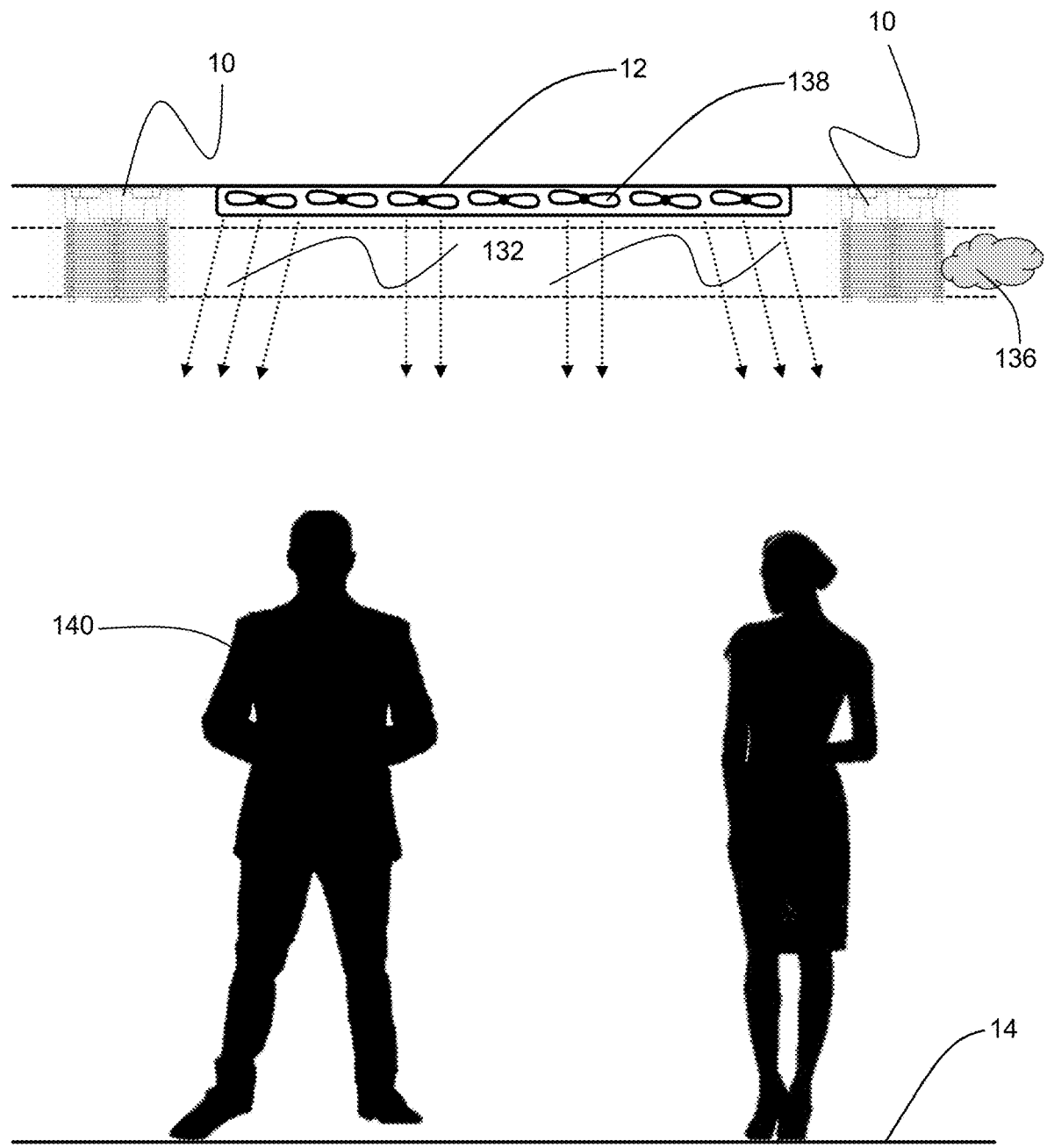
Figure 3:
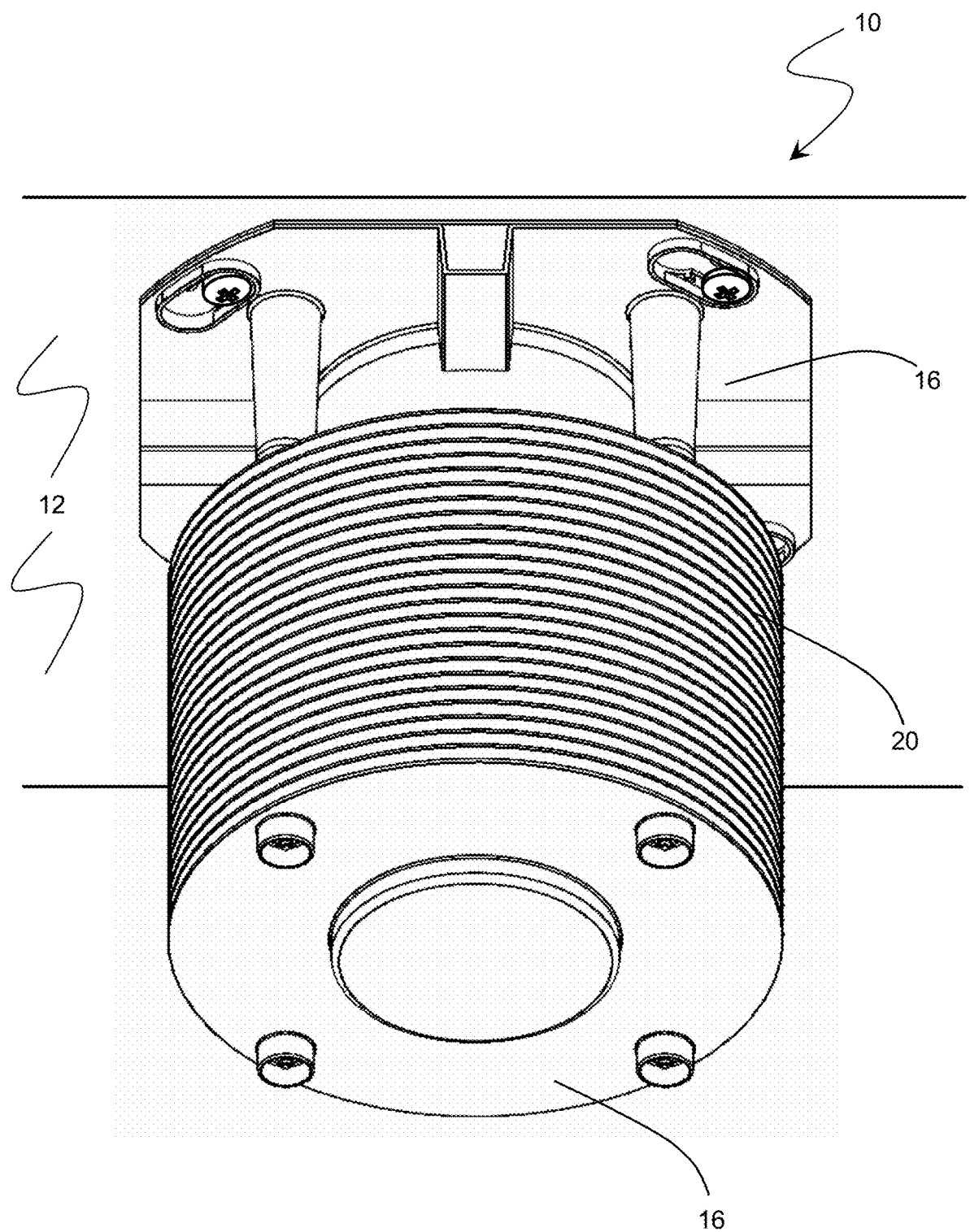
Figure 4:
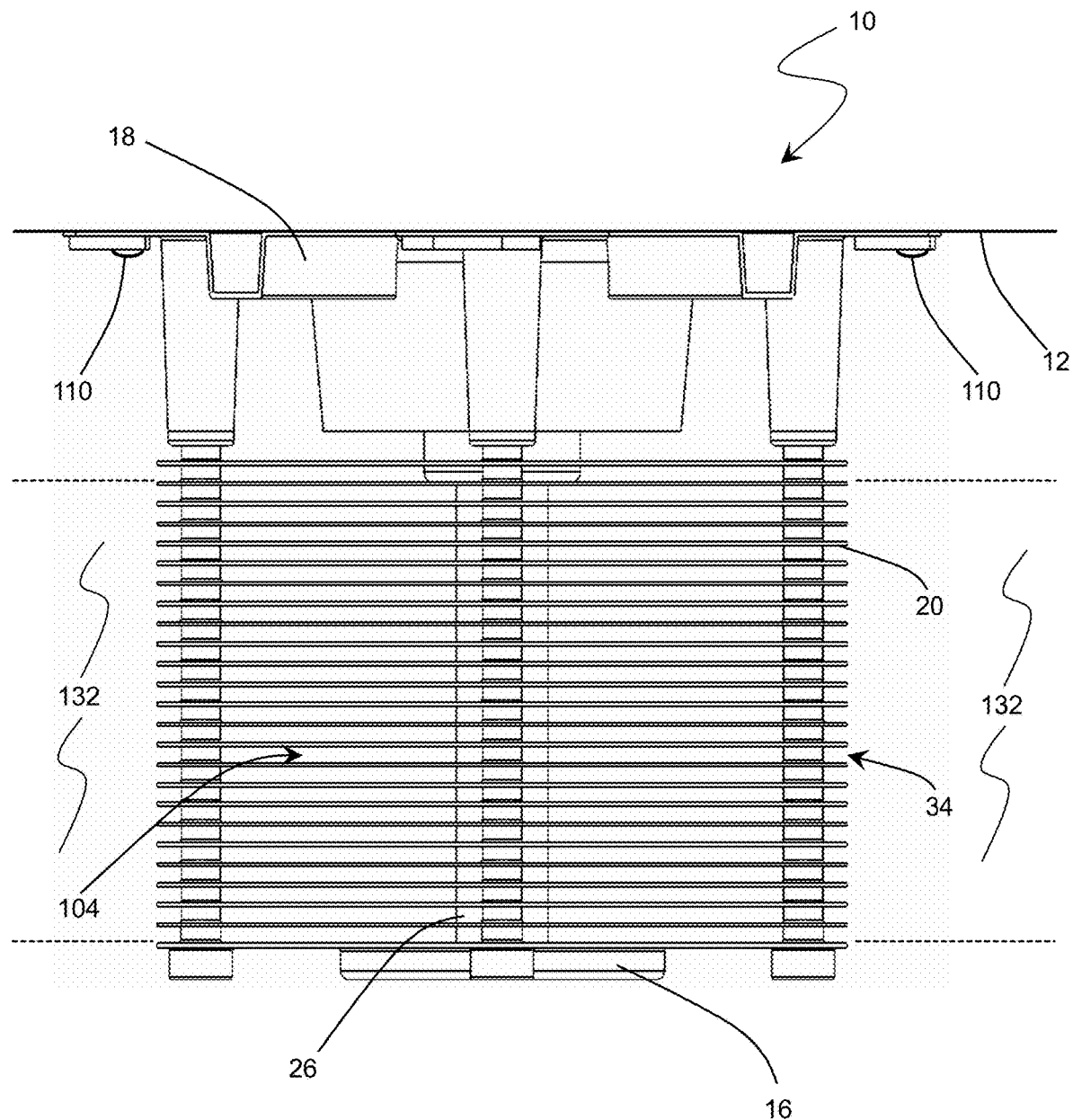
Figure 5:
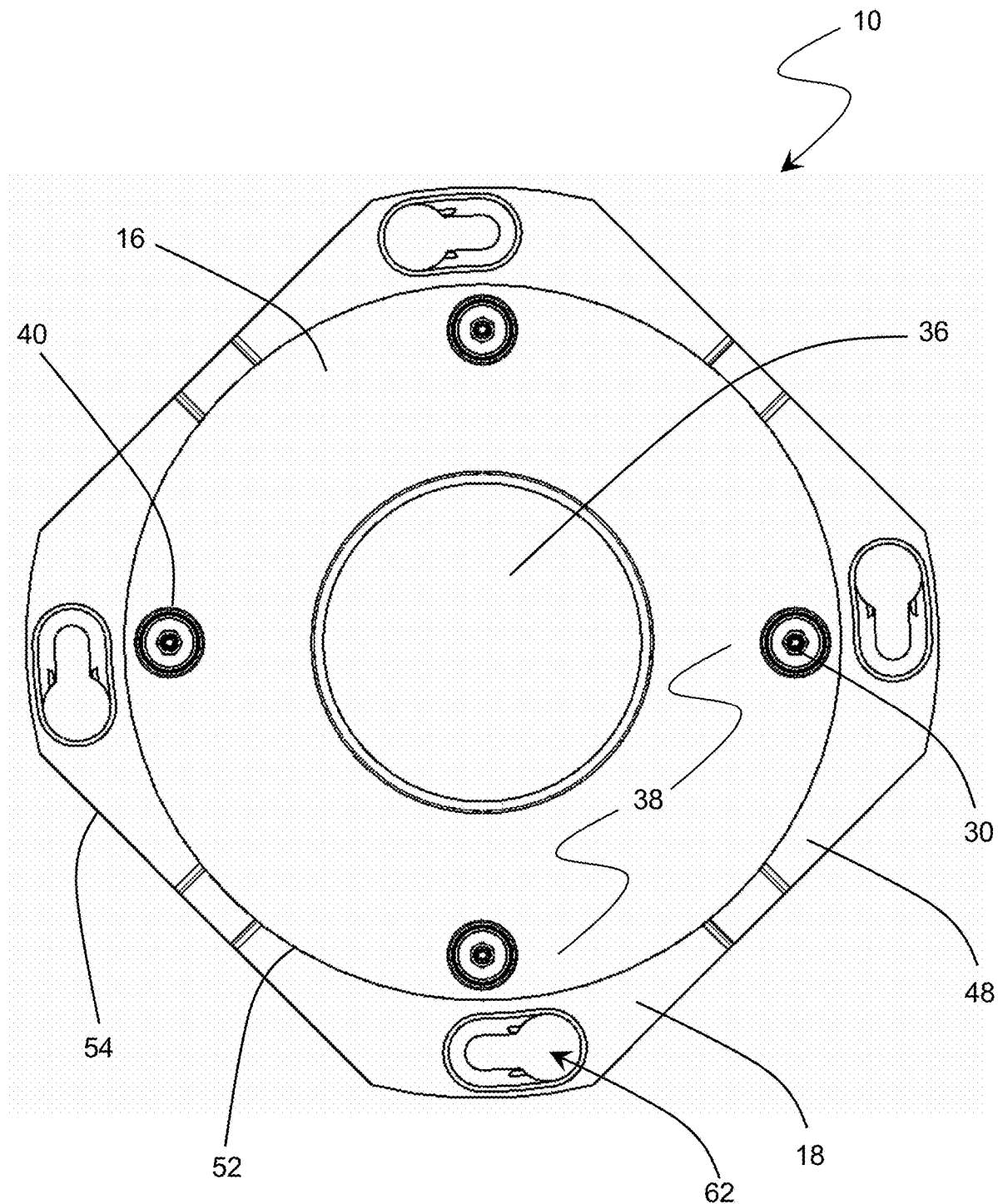
Figure 6:
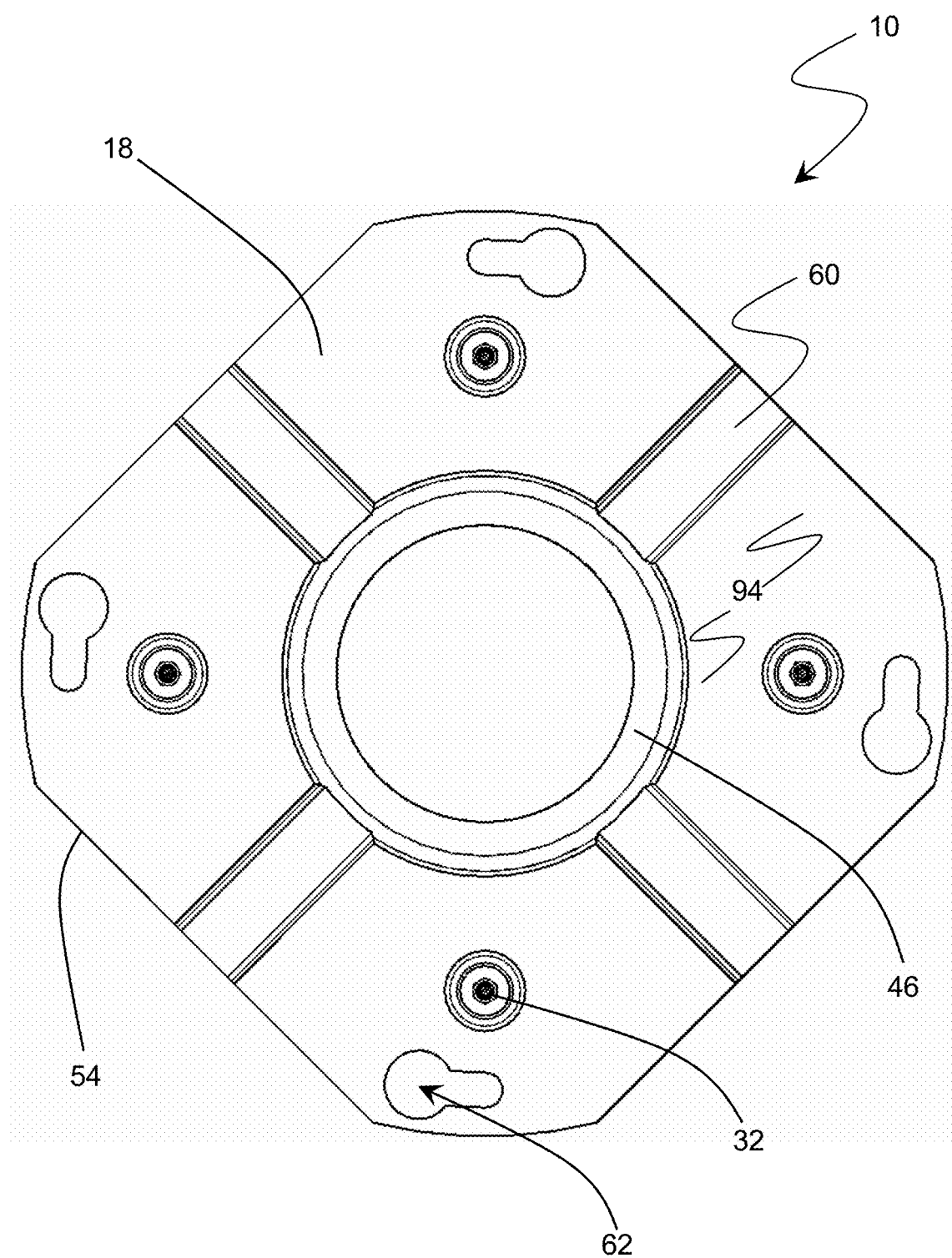

Referring now to the drawings, preferred illustrative embodiments of the present invention are shown in detail. Although the drawings represent embodiments of the present invention, the drawings are not necessarily to scale and certain features may be exaggerated to better illustrate and explain the present invention. Further, the embodiments set forth herein are not intended to be exhaustive or otherwise to limit or restrict the invention to the precise forms and configurations shown in the drawings and disclosed in the following detailed description.

The wearing of masks, other face coverings and shields as well as the use of plexiglass barriers and social distancing all work to help limit the transmission of infections and viruses such as influenza and SARS-CoV-2, however, these tools will not kill and eliminate the infectious viral and bacterial particles and pathogens. The present invention provides an ultraviolet light fixture 10 that will provide ultraviolet light and radiation having a wavelength of 200 nanometers-280 nanometers, also known as Ultraviolet-C (UV-C) light and radiation. Ultraviolet light fixture 10 will enable ultraviolet radiation to create a sterilization field and enter an area to eradicate infectious viral material, bacteria and pathogens, such as a cloud of infectious influenza or SARS-CoV-2 particles and the like. Light fixture 10 will direct the UV-C radiation in a manner such that any humans or animals present in the area during operation of an ultraviolet-C lamp will not be harmed by the UV-C radiation.

According to an embodiment of the present invention, ultraviolet light fixture 10 includes a top end cap 16, a base 18 and a plurality of louvers 22 as depicted in FIGS. 3-6. (See also FIGS. 14A-14C). FIGS. 2A-2F illustrate how fixture 10 along with an ultraviolet-C bulb 26 and blub holder 28, may be deployed in a typical room setting to sterilize and disinfect the air in the room. Fixture 10 may be secured to a ceiling 12 such that fixture 10 directs any UV-C radiation from bulb 26 outward from fixture 10 to create a sterilization field 132 (see also FIGS. 4, 16-20 and 21B) and away from any humans and animals that may be present in the room and standing on a floor 14. In this particular embodiment of the present invention, bulb 26 may be mounted vertically within fixture 10 to direct approximately 80% of UV-C radiation outward and generally horizontal from fixture 10 to sterilize any air flowing outside of fixture 10. Fixture 10 may be mounted in areas or rooms with a ceiling height of eight feet or more to ensure UV-C light and radiation is at a safe level above humans and animals and away from eyes that may be damaged by UV-C radiation.

Fixture 10 will work with the room's heating ventilation and air conditioning (HVAC) system 138 as well as in rooms with ceiling fans to ensure the air flowing within the room is sterilized and any viruses, bacteria and pathogens are eradicated from the air to help maintain the health of those individuals in the room. FIGS. 2B-2F illustrate how an infectious cloud 136 produced by a first individual 140 may travel through the room to sterilization field 132 and fixture 10.

Figure 7A:
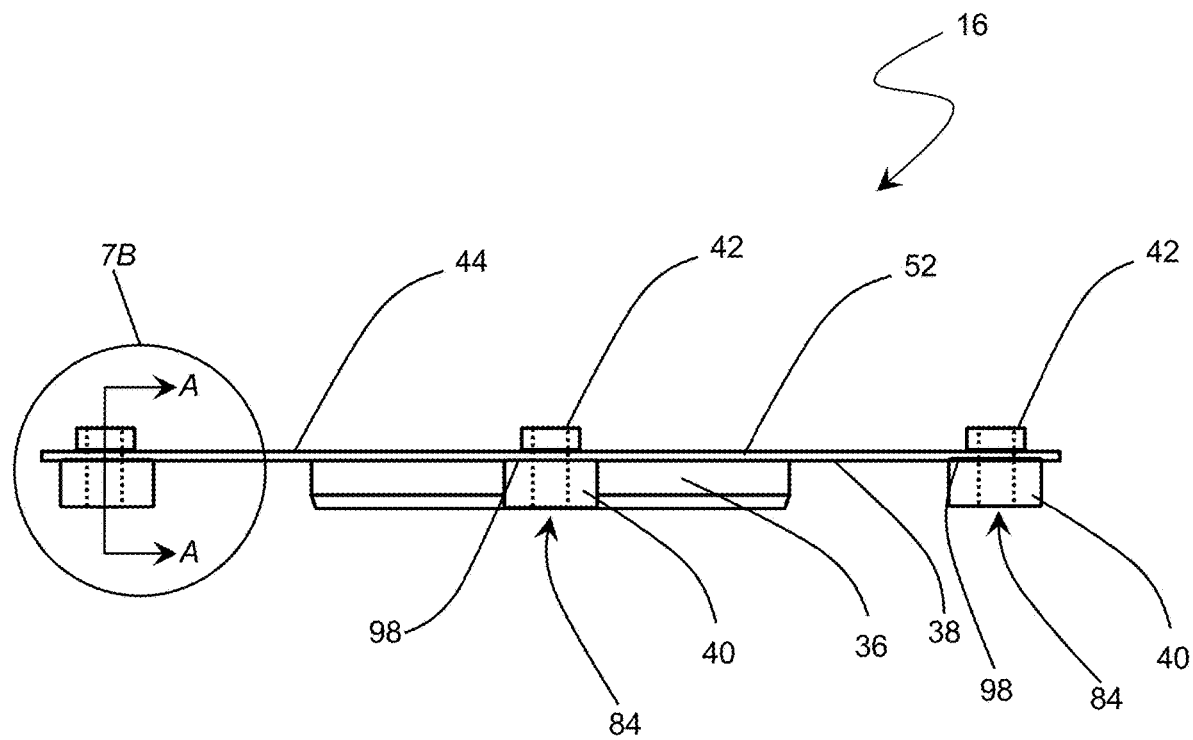
Figure 7B:
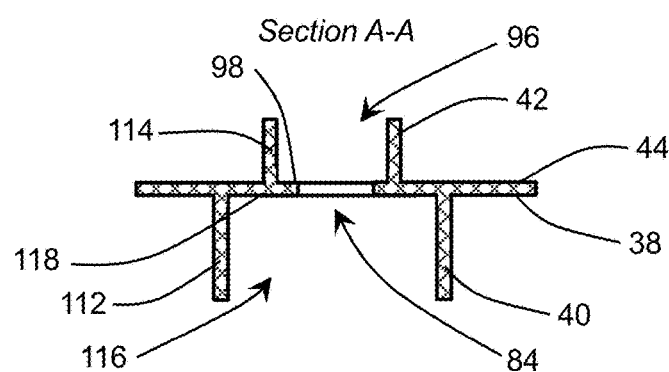
Figure 7C:
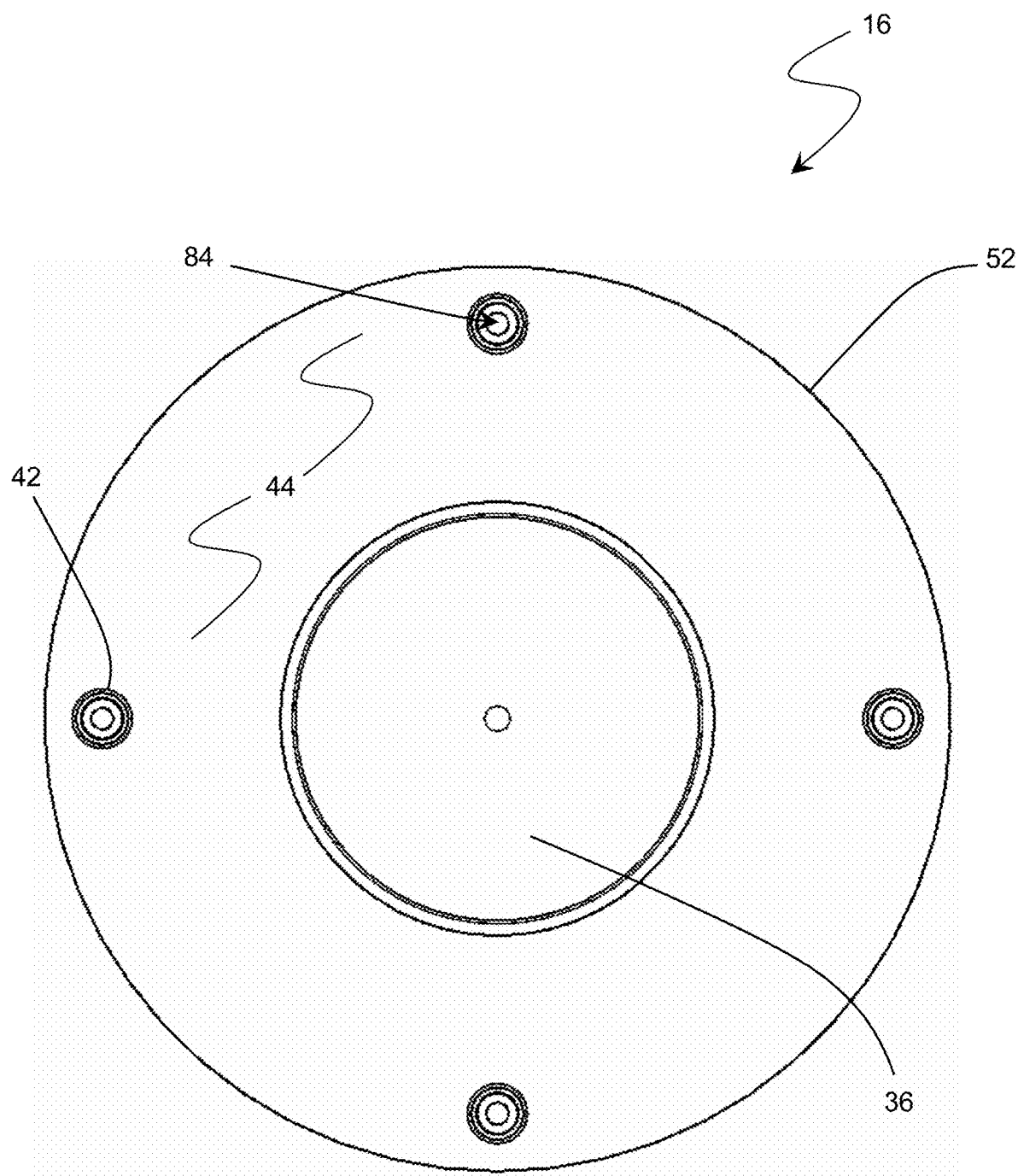

Now referring to FIGS. 7A-7C, top end cap 16 is illustrated. According to an embodiment of the present invention, end cap 16 is depicted in a generally round shape, but it is important to note, that end cap 16 may be of any shape, such as oval, rectangular, triangular and the like and fixture 10 will still function to enable UV-C radiation to pass outside fixture 10 and allow air to pass into fixture 10 such that the UV-C radiation can work to eradicate viruses, bacteria and pathogens from the air. Shape of end cap 16 may be modified to fit any type of aesthetic or architectural preference one so desires as well as engineering or design modifications required or dictated by any existing structure. End cap 16 may be manufactured of any type of material suitable for absorbing UV-C radiation including polymers such as glass fiber reinforced polypropylene (PP) or acrylonitrile butadiene styrene (ABS). The material may have a published tensile yield strength greater than 5,000 pounds per square inch (psi). The material may have a published heat deflection temperature (HDT) at 1.8 mega pascals (MPa) (264 psi) greater than 180 degrees Fahrenheit. The material may have a yellow Underwriters Laboratories (UL) 94 card with a flammability of V-0 at thickness of 1.5 mm.

Top end cap 16 includes a dome 36 that extends generally outward from a top surface 38 of end cap 16. Dome 36 may be generally circular in shape and may be sized to accommodate and provide clearance to an end of bulb 26. A plurality of fastener seats 40 extend generally outward from top surface 38 of end cap 16. In this particular embodiment of the present invention, four fastener seats 40 extend outward from top surface 38 and fastener seats 40 are generally round in shape. A plurality of female posts 42 extend generally outward from a bottom surface 44 of end cap 16. In this particular embodiment of the present invention, four female posts 42 extend outward from bottom surface 44 and female posts 42 are generally round in shape. However, it is important to note, that seats 40 and posts 42 may designed in any shape, such as oval, rectangular, triangular, and the like and still maintain the function of fixture 10. Seats 40 and posts 42 may be positioned on top end cap 16 between an outer edge 52 and dome 36 of top end cap 16.

Fastener seats 40 include a wall 112 that extends outward from top surface 38 to create a well 116, well 116 sized to capture a typical fastener 30 such as a threaded nut. Fastener seats 40 further include a shoulder 118 within well 116 to provide a bearing surface for fastener 30 to engage during assembly. Female posts 42 include a wall 114 that extends outward from bottom surface 44 to create a well 96. Female posts further include a shoulder 98 within well 96. A hole 84 passes through both fastener seat 40 and female post 42.

Figure 8A:
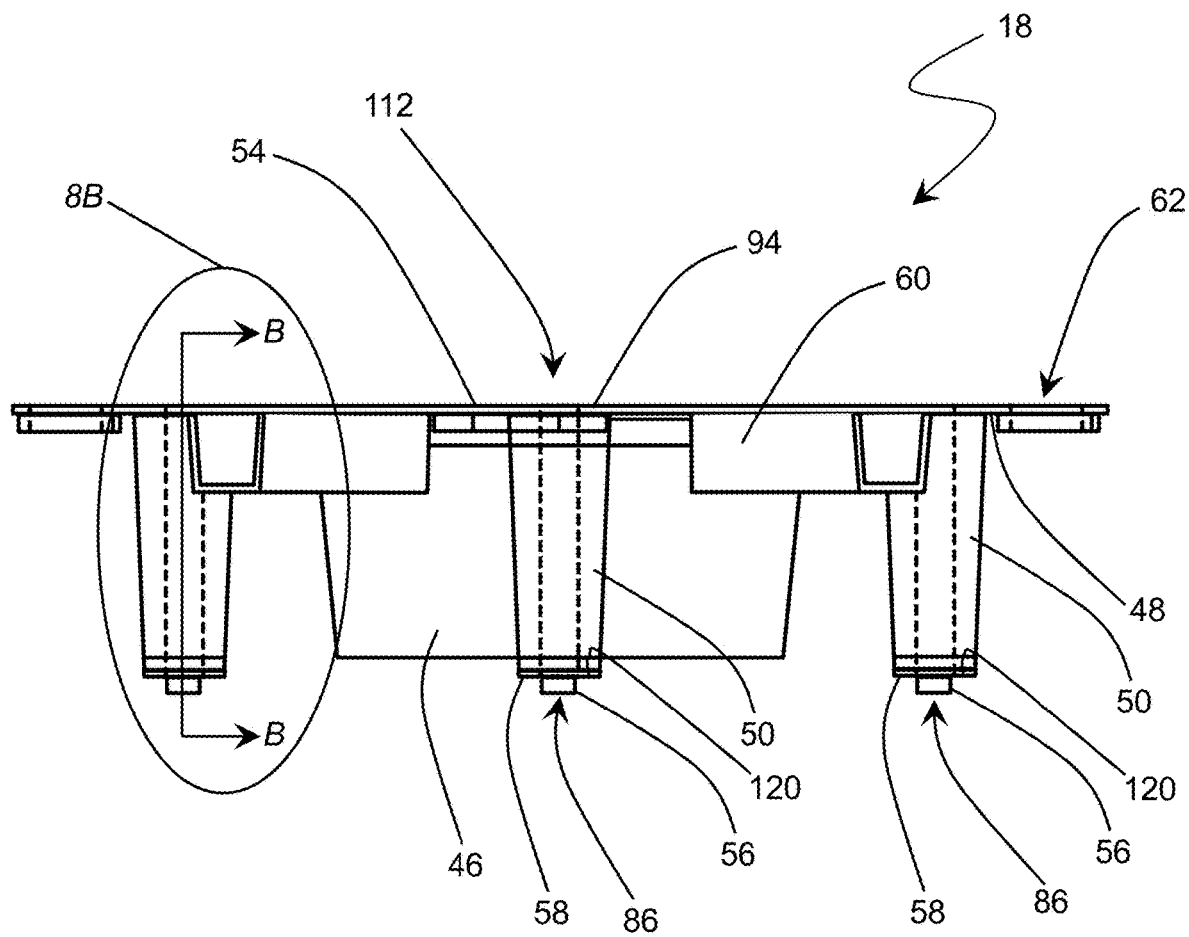
Figure 8B:
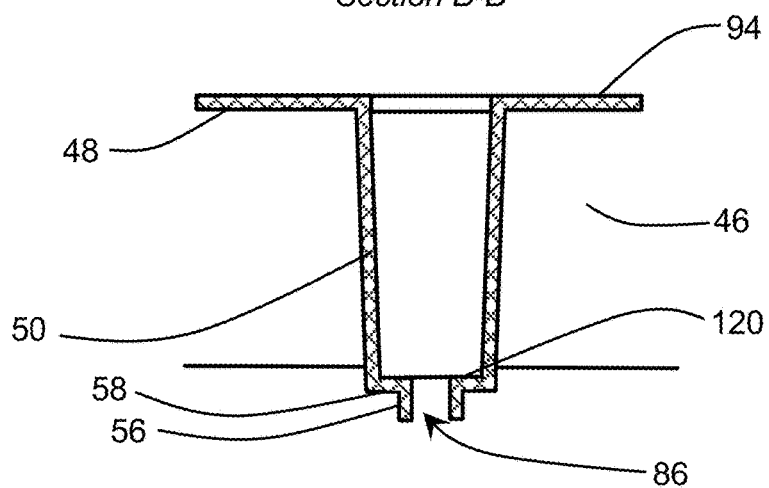
Figure 8C:
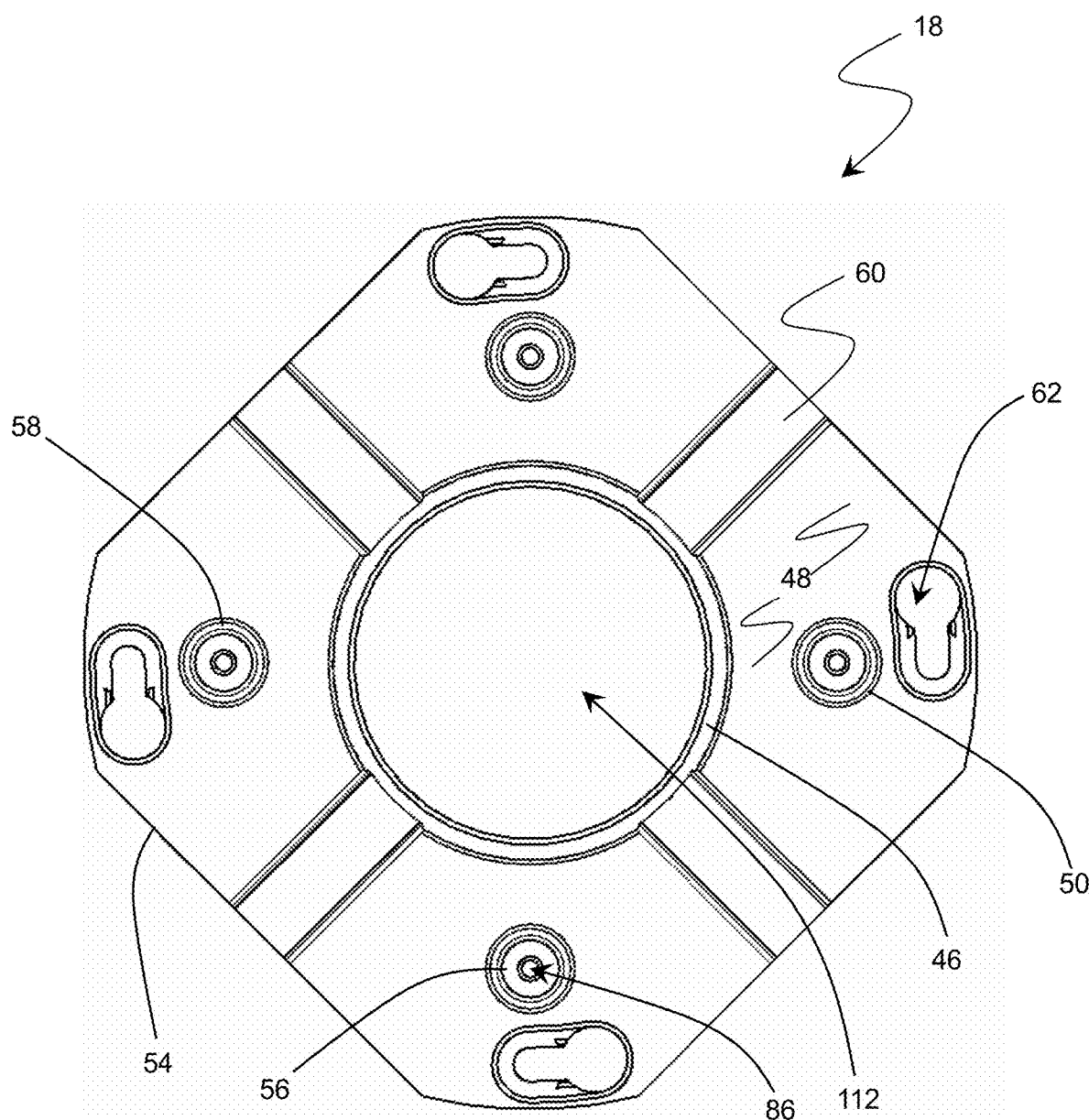

Referring now to FIGS. 8A-8C, base 18 is illustrated. According to an embodiment of the present invention, base 18 is depicted in a generally rectangular shape having rounded corners. However, it is important to note, that base 18 may be of any shape, such as circular, oval, rectangular, triangular and the like and fixture 10 will still function to enable UV-C radiation to pass outside fixture 10 and allow air to pass into fixture 10 such that the UV-C radiation can work to eradicate viruses, bacteria and pathogens from the air. Shape of base 18 may be modified to fit any type of aesthetic or architectural preference one so desires as well as engineering or design modifications required or dictated by any existing structure. Base 18 may be manufactured of any type of material suitable for absorbing UV-C radiation including polymers such as glass fiber reinforced polypropylene (PP) or acrylonitrile butadiene styrene (ABS). The material may have a published tensile yield strength greater than 5,000 pounds per square inch (psi). The material may have a published heat deflection temperature (HDT) at 1.8 mega pascals (MPa) (264 psi) greater than 180 degrees Fahrenheit. The material may have a yellow Underwriters Laboratories (UL) 94 card with a flammability of V-0 at thickness of 1.5 mm.

Base 18 includes a wall 46 extending generally outward from a upper surface 48 of base 18. Wall 46 may be generally circular in shape to provide an aperture 112. Aperture 112 may be sized to accept bulb holder 28 and allow clearance for bulb 26 to pass thorough. However, it is important to note, that wall 46 may designed in any shape, such as oval, rectangular, triangular, and the like and still maintain the function of fixture 10. Wall 46 may extend outward from upper surface 48 a distance to enclose a top of bulb holder 28. Wall 46 and aperture 112 may be positioned generally in the center of base 18 as depicted in FIG. 8C. Wall 46 may also include a shallow draft angle to enable ease manufacture.

Base 18 further includes a plurality of pillars 50 extending generally outward from top side 48 of base 18. Pillars 18 may be generally round in shape and extend a distance from top side 48 that may be slightly longer than wall 46. However, it is important to note, that pillar 18 may designed in any shape, such as oval, rectangular, triangular, and the like and still maintain the function of fixture 10. Pillars 50 may also include a shallow draft angle to enable ease of manufacture. Pillars 50 may be positioned on base 18 between an outer edge 54 and wall 46 of base 18. Pillars 50 may include a male peg 56 that extends outward from a top 58 of pillars 50 and peg 56 may be generally round in shape. However, it is important to note, that peg 56 may designed in any shape, such as oval, rectangular, triangular, and the like and still maintain the function of fixture 10. Pillars 50 further include a shoulder 120 at the underside of male peg 56 to provide a bearing surface for a fastener 32, such as a typical threaded nut, to engage during assembly. A hole 86 passes through pillar 50 and male peg 56.

Base 18 also include a plurality of struts 60 protruding generally outward from upper surface 48 of base 18 and extending from outer edge 54 to wall 46. Struts 60 may provide rigidity and support to base 18 as base 18 supports fixture 10. Base 18 further includes a plurality of holes 62 positioned near outer edge 54 of base 18. Holes 62 are sized to accommodate any type of fastener 110 (see FIG. 4) to secure base 18 and fixture 10 to any type of surface. In this particular embodiment of the present invention, holes 62 are in the general shape of a tear drop, a first portion of hole 62 has a larger diameter than a second portion of hole 62, a design generally known in the art to aid in the mounting of base 18 and fixture 10 to a surface. The diameter of the first portion hole 62 is generally larger than a diameter of a head of fastener 110, allowing for a head of fastener 110 to pass through hole 52. The diameter of the second portion of hole 62 is generally smaller than the diameter of the head of fastener 110, allowing hole 62 to capture fastener 110 to base 18 as a body of fastener 110 enters the second portion of the diameter of hole 62. When all fasteners have been secured to a surface, first portion of hole 62 may engage fasteners 110 at the heads. With all head of fasteners 110 extending through the first portion of hole 62, base 18 may be rotated such that the body of each of fasteners 110 enters the second portion of hole 62 thereby capturing fasteners 110 to base 18 to secure fixture 10 to the surface. It is important to note, however, that holes 62 may be of any shape such as round, oval, and the like and still act to secure base 18 and fixture 10 to any surface with any type of fasteners.

Figure 9A:
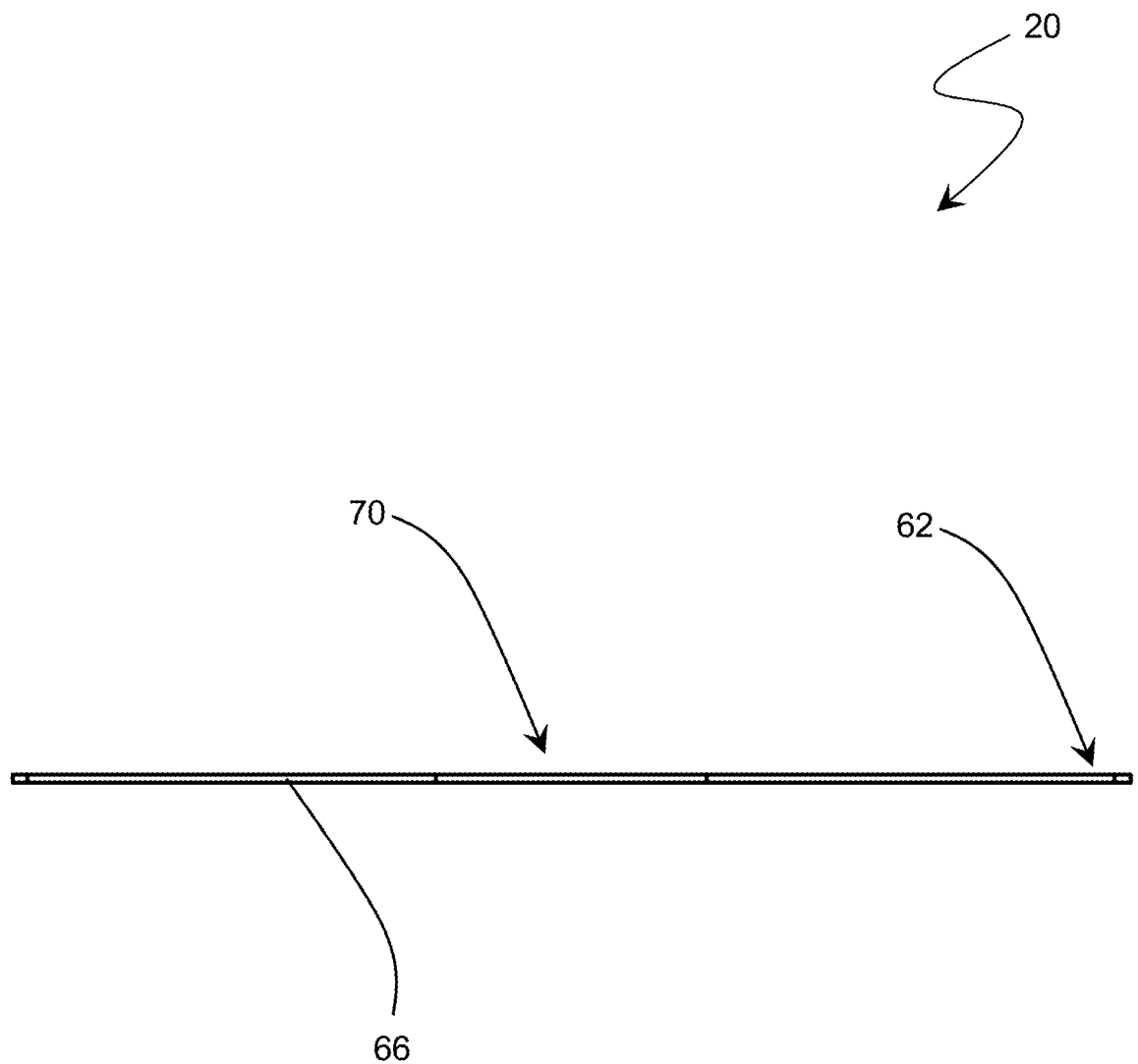
Figure 9B:
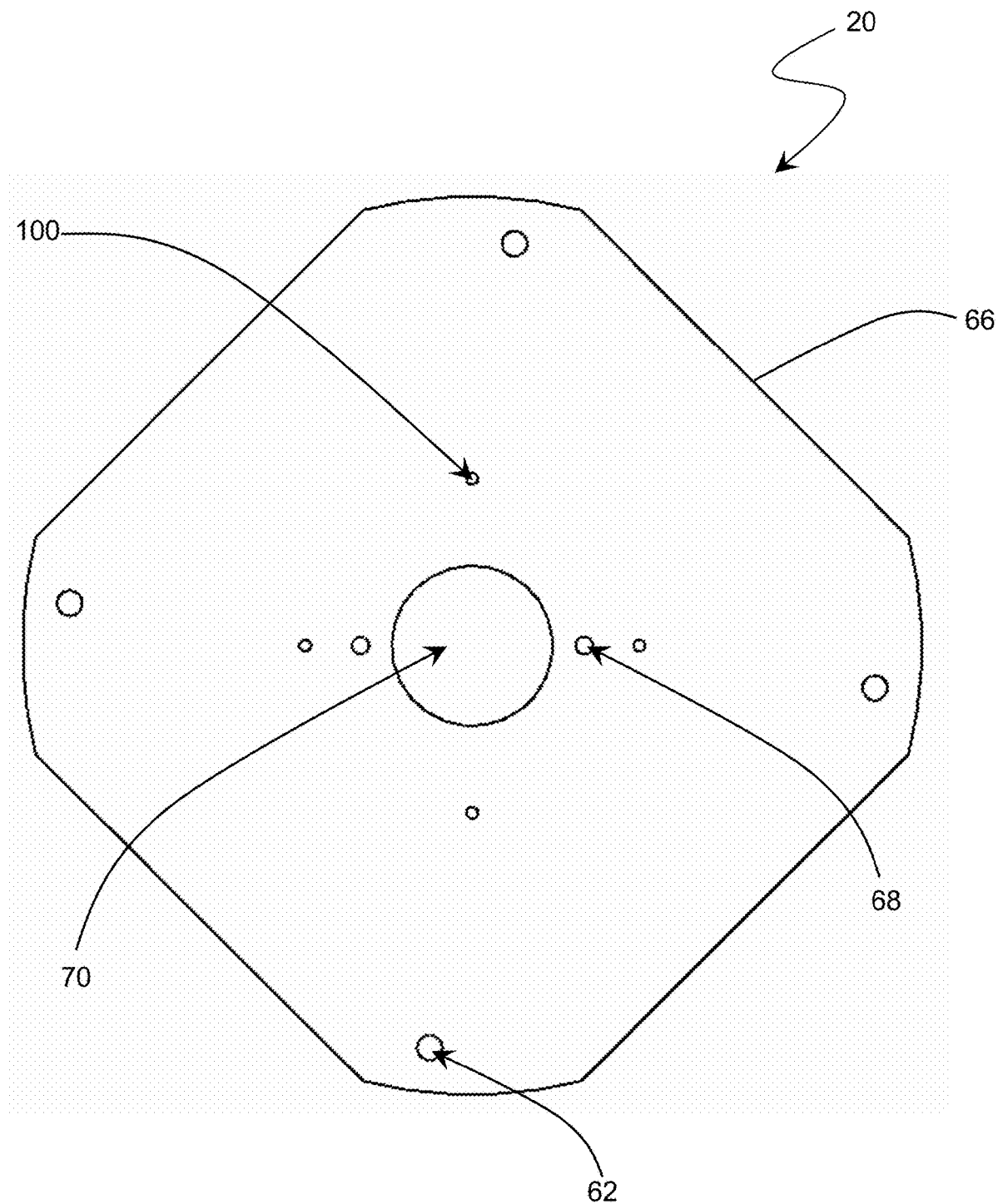
Figure 10A:
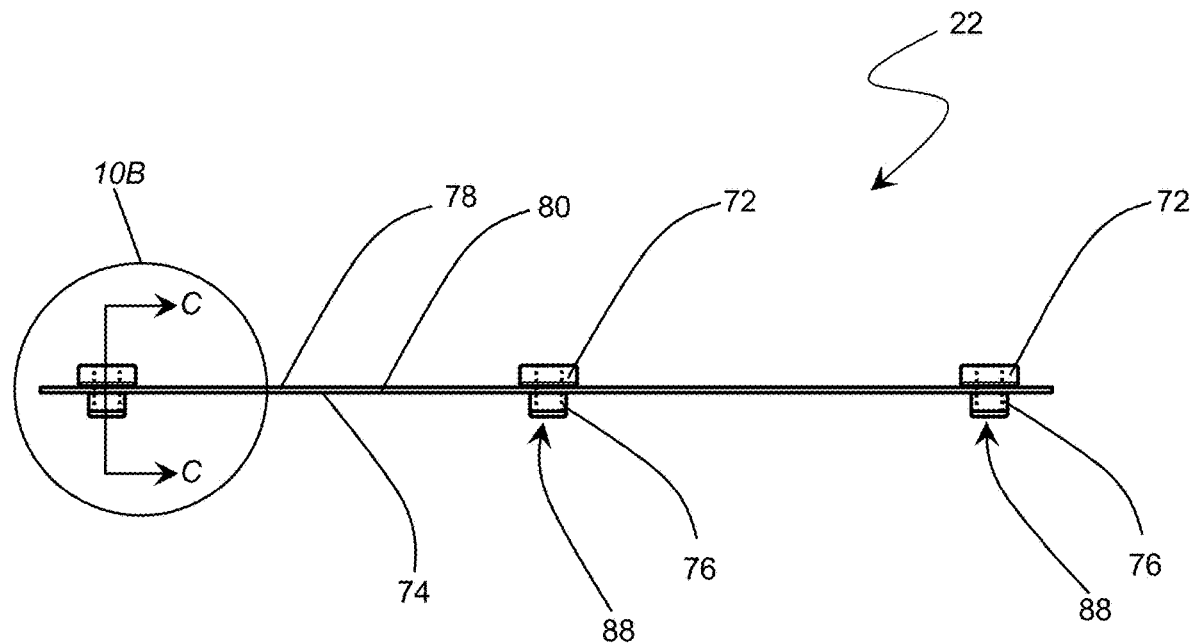
Figure 10B:
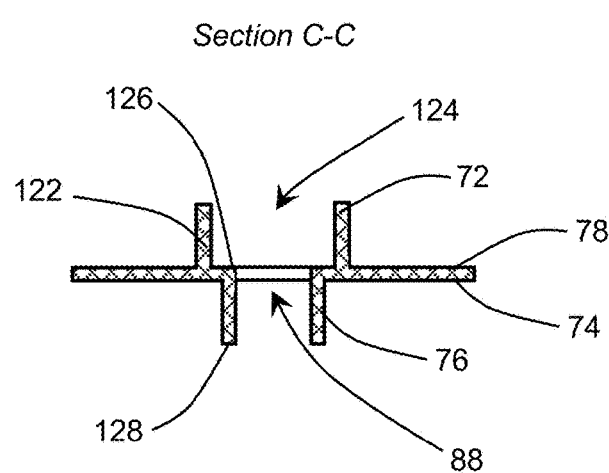
Figure 10C:
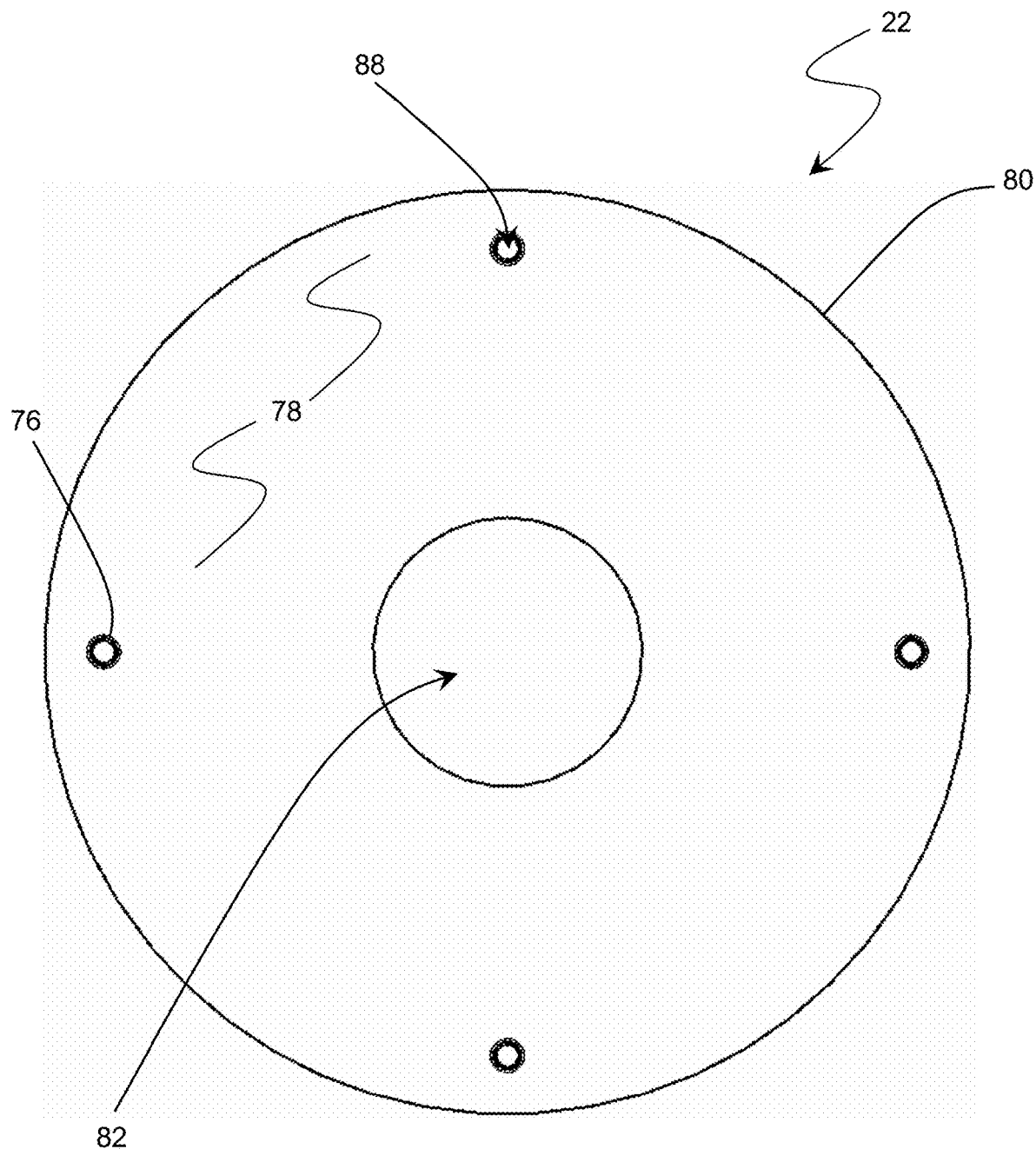
Figure 10D:
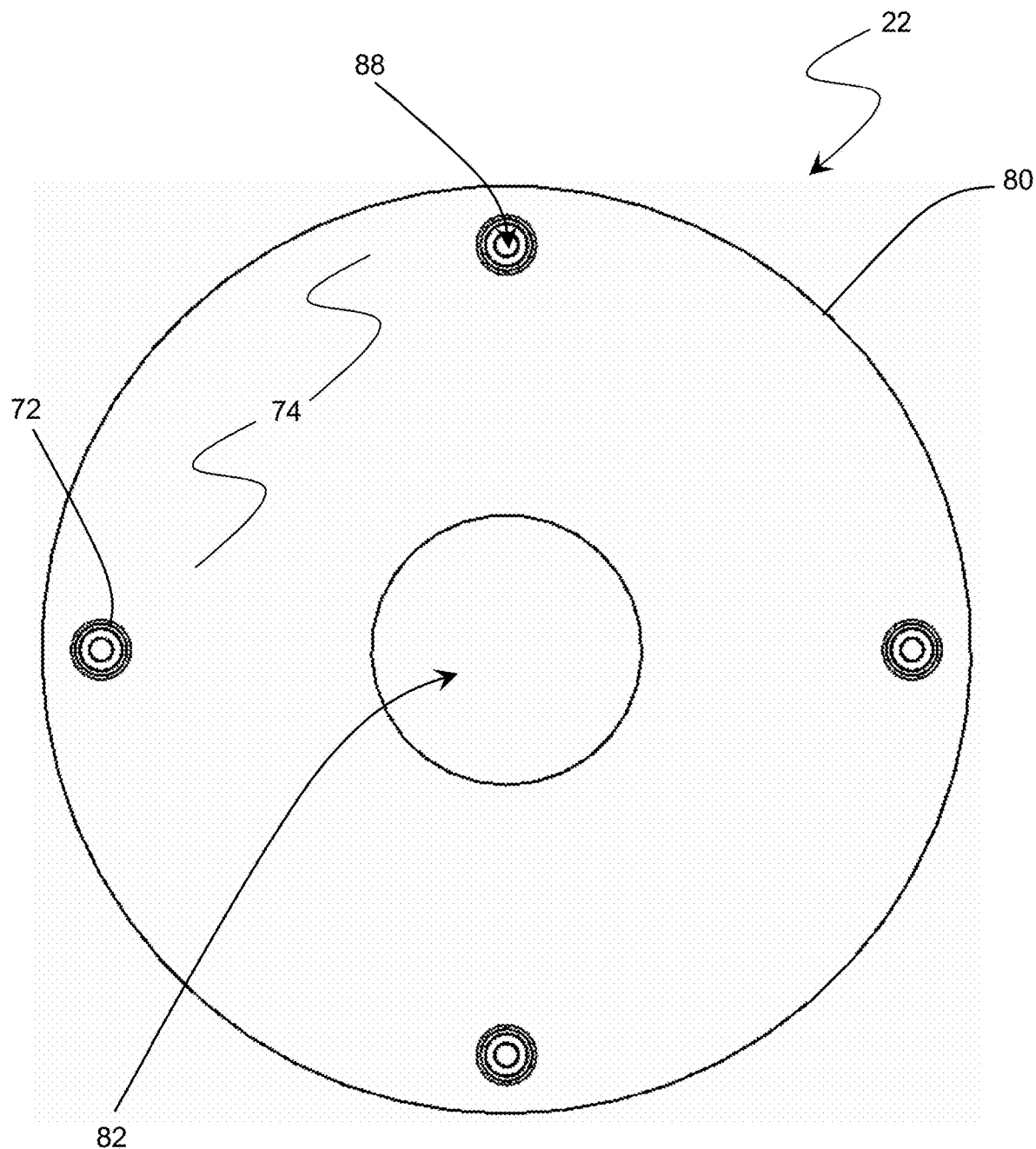

FIGS. 9A and 9B illustrate mounting plate 20. According to an embodiment of the present invention, a mounting plate 20 is depicted in a generally rectangular shape having rounded corners and may match the shape of base 18 at outer edge 54. However, it is important to note, that mounting plate 20 may be of any shape, such as circular, oval, rectangular, triangular and the like and still enable the function of fixture 10 to eradicate viruses, bacteria and pathogens from the air. Shape of mounting plate 20 may be modified to fit any type of aesthetic or architectural preference one so desires as well as engineering or design modifications required or dictated by any existing structure. Mounting plate 20 may be manufactured of any type of material to provide suitable support for bulb holder 28, bulb 26 and fixture 10 including but not limited to metals such as steel, aluminum and the like.

Mounting plate 20 includes a first plurality of holes 64 positioned near an outer edge 66 and configure to align with holes 62 of base 18 sized to accept fasteners 110 and secure plate 20, base 18 and fixture 10 to the surface. Mounting plate 20 also includes a second plurality of holes 68 positioned near a center of plate 20 configured to align with holes 70 of bulb holder 28 and sized to accept fasteners to secure bulb holder 28 to mounting plate 20 and fixture 10. Further, mounting plate includes an aperture 70 generally positioned at the center of plate 20 and sized to allow for the passage of any electrical wiring from a wall, floor, ceiling or other surface through plate 20 to bulb holder 28 to provide power to operate bulb 26. Still further, mounting plate 20 may include a plurality of holes 100 to accept fasteners to mount a typical electrical box 102. Electrical box 102 provided to house the electrical connections between bulb base 28 and the building or structures main electrical system to enable energy to pass to bulb 26 and have bulb 28 function to produce UV-C light.

Now referring to FIGS. 10A-10D, louver 22 is illustrated. According to an embodiment of the present invention, louver 22 is depicted in a generally round shape, but it is important to note, that louver 22 may be of any shape, such as oval, rectangular, triangular and the like and fixture 10 will still function to enable UV-C radiation to pass outside fixture 10 and allow air to pass into fixture 10 such that the UV-C radiation can work to eradicate viruses, bacteria and pathogens from the air. Shape of louver 22 may be modified to fit any type of aesthetic or architectural preference one so desires as well as engineering or design modifications required or dictated by any existing structure. Louver 22 may be manufactured of any type of material suitable for absorbing UV-C radiation including polymers such as glass fiber reinforced polypropylene (PP) or acrylonitrile butadiene styrene (ABS). The material may have a published tensile yield strength greater than 5,000 pounds per square inch (psi). The material may have a published heat deflection temperature (HDT) at 1.8 mega pascals (MPa) (264 psi) greater than 180 degrees Fahrenheit. The material may have a yellow Underwriters Laboratories (UL) 94 card with a flammability of V-0 at thickness of 1.5 mm. Louver 22 may also include an aluminum surface to facilitate better UV-C radiation reflection and output from fixture 10.

Louver 22 includes an aperture 82 at a center of louver 22. Aperture 22 may be generally circular in shape and may be sized to allow free passage of bulb 28. Louver 22 also includes a plurality of female posts 72 extend generally outward from a bottom surface 78 of louver 22. In this particular embodiment of the present invention, four female posts 72 extend outward from bottom surface 78 and female posts 72 are generally round in shape. A plurality of male pegs 76 extend generally outward from a top surface 74 of louver 22. In this particular embodiment of the present invention, four male pegs 76 extend outward from top surface 74 and male pegs 76 are generally round in shape. However, it is important to note, that post 72 and peg 76 may designed in any shape, such as oval, rectangular, triangular, and the like and still maintain the function of fixture 10. Post 72 and peg 76 may be positioned on louver 22 between an outer edge 80 and aperture 82 of louver 22.

The radial width of louver 22, the difference between the outside radius of louver 22 and the radius of aperture 82 may be designed to be relatively large to control the UV-C light or radiation leaving UV-C bulb 26 to create sterilization field 132 (see FIGS. 2, 4, 16-20 and 21B) and ensure the safety of any humans or animals proximate fixture 10. Further, the radius of aperture 82 may be relatively large to accommodate a number of different bulb 26 sizes.

Female posts 72 include a wall 122 that extends outward from bottom surface 78 to create a well 124 and a shoulder 126 within well 124. Well 124 has an inner diameter larger than the outer diameter of male pegs 76 to allow male pegs 76 to next within well 124 of female posts 72 as a first louver 22 is pressed against a second louver 22. Shoulder 126 provides a bearing surface for a top 128 of male pegs 76 to seat against when the first louver 22 is pressed against the second louver 22. A hole 88 passes through both female post 72 and male peg 76.

Figure 11:
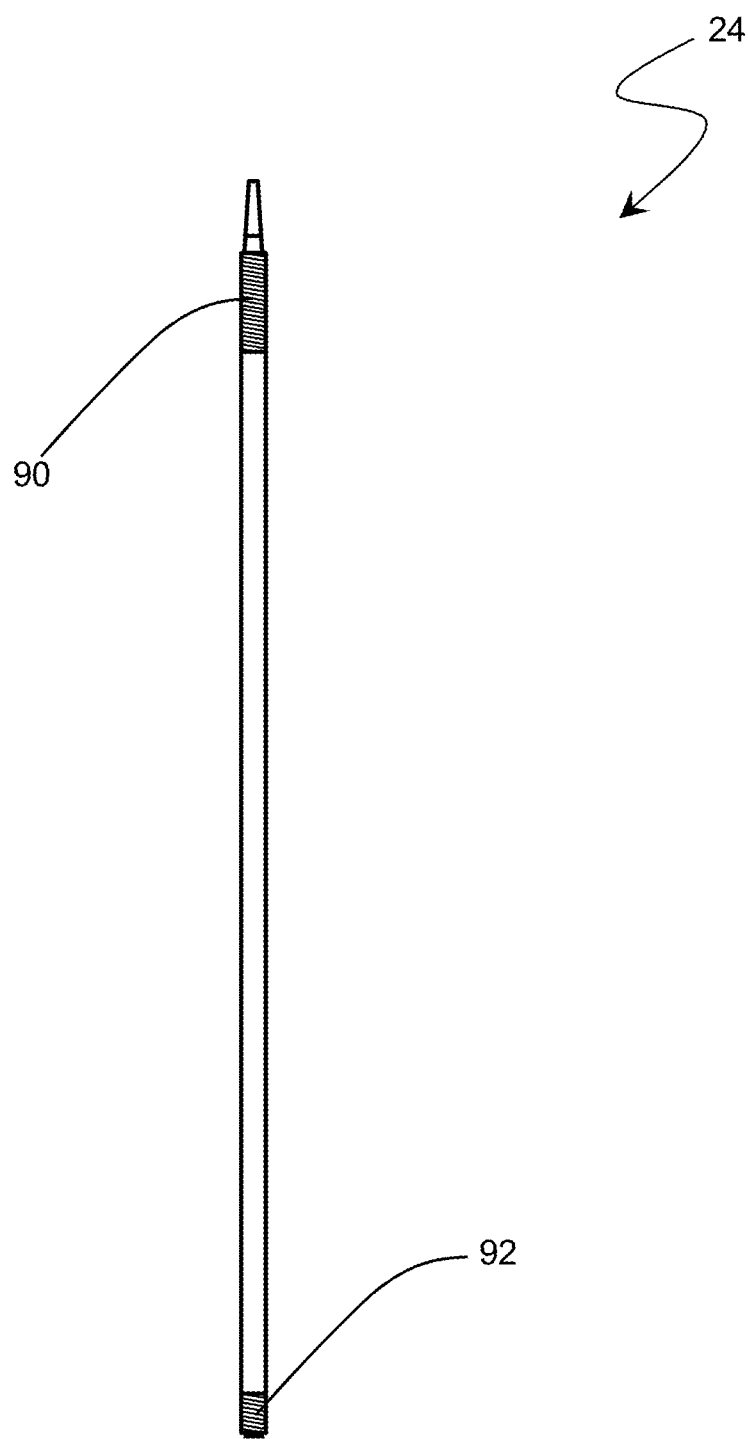

Referring now to FIG. 11, dowel 24 is depicted. According to an embodiment of the present invention, dowel 24 may have a generally circular cross-section and extend a length to accommodate the length of fixture 10. Dowel 24 may include threaded ends 90, 92 to accept and secure typical fasteners 30, 32, such as a threaded nut, to secure the fasteners to dowel 24. Dowel 24 may be manufactured of any type of material to provide suitable support for fixture 10 including but not limited to polymers and metals such as steel, aluminum and the like.

Figure 12:
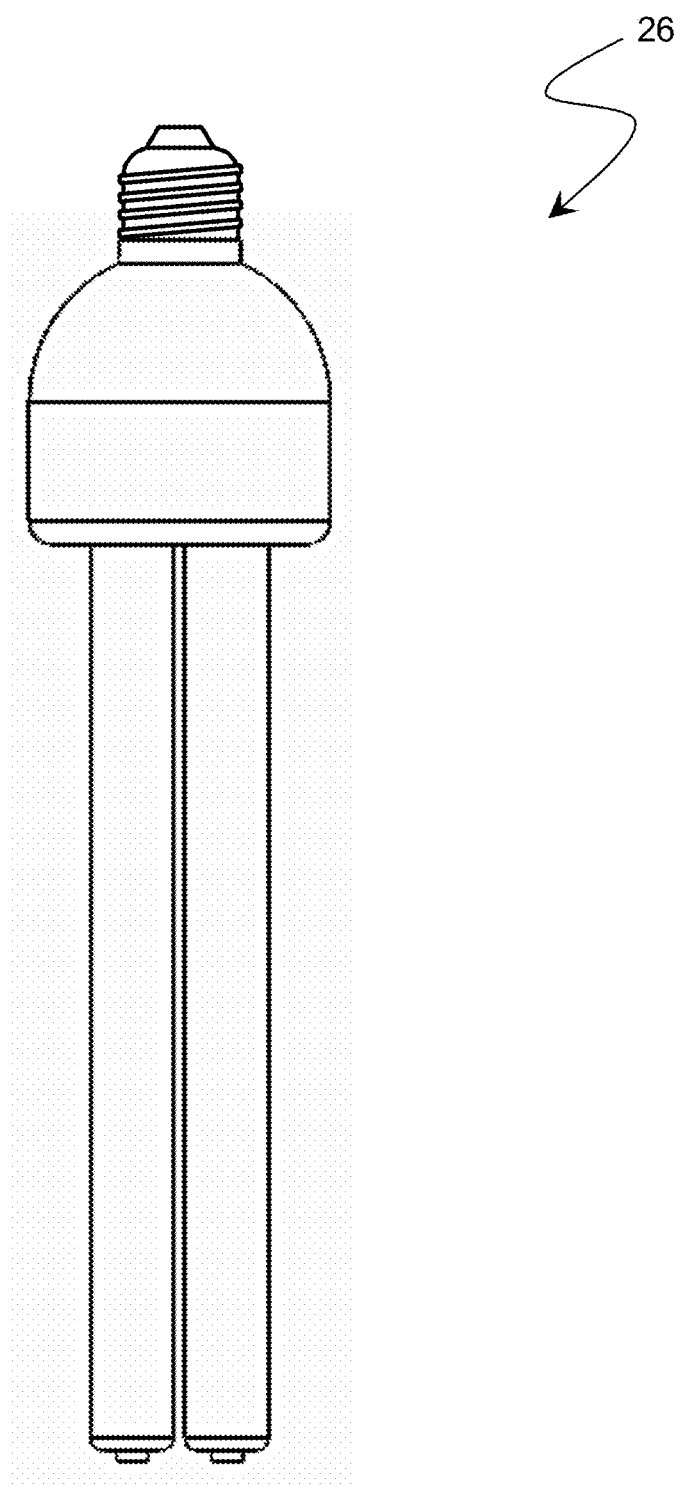
Figure 13:
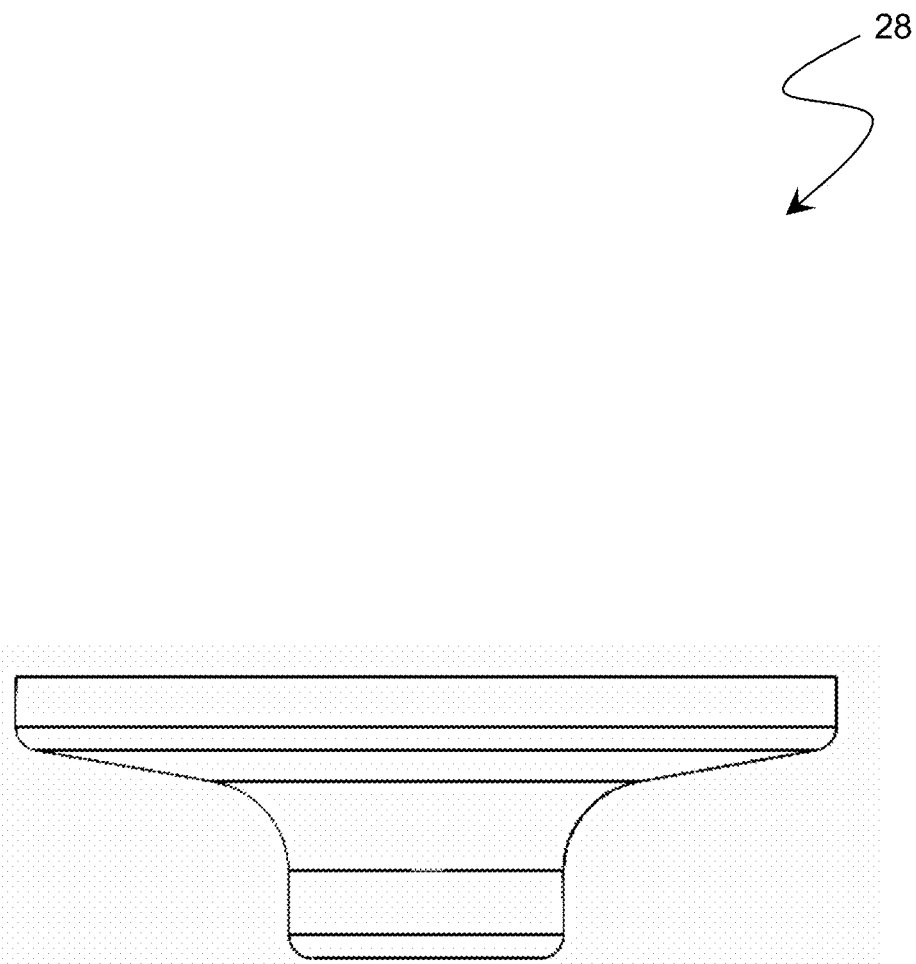

FIG. 12 illustrates the typical UV-C bulb 26 that may be installed in fixture 10 using bulb holder 28 depicted in FIG. 13.

Referring once again to FIGS. 7A-8C and FIGS. 10A-10D, as discussed above for louver 22, an outer diameter of male pegs 56, 76 are sized such that the outer diameter of male pegs 56, 76 is less than an inner diameter of female posts 42, 72 such that male pegs 56, 76 may nest within wells 96, 124 of female posts 42, 72, respectively as FIG. 10 is assembled (discussed further below). Also, as discussed above, fastener seat 40 and female post 42 include a hole 84 that extends through top end cap 16. Male peg 56 of pillar 50 of base 18 includes a hole 86. Male peg 76 and female post 72 include a hole 88 that extends through louver 22. Holes 84, 86, 88 are generally circular in shape and sized such that the inside diameter is larger than the outside diameter of dowel 24 to allow dowel 24 to pass freely through holes 84, 86, 88.

Male pegs 56, 76 and female posts 42, 72 may be designed to a specific height to enable a gap 34 between base 18 and louver 22, between individual louvers 22 and between louver 22 and top end cap 16. A large gap will enable more air to flow into a sterilization chamber 104 of fixture 10 to be sterilized by the UV-C lamp 28 while also allowing for a greater amount of UV-C light/radiation to leave the fixture and create sterilization field 132 (see FIGS. 2, 4, 16-20 and 21B) thereby sterilizing more of the air around the fixture. A narrow gap will enable less air to flow into the fixture to be sterilized by the UV-C lamp 28 while also allowing for a lesser amount of UV-C light/radiation to leave the fixture and create sterilization field 132 thereby sterilizing less of the air around the fixture. The size of gap 34 will be determined by the heights of pegs 56, 76 and post 42, 72. The ability to control and vary the size of gap 34 will enable a variety of uses for fixture 10. For example, fixture 10 may be configured with small gaps 34 for use in smaller compact areas where sterilization of the air is required, but the amount of UV-C radiation being expelled by fixture 10 should be tightly controlled to ensure the safety of individuals in close proximity to the lamp. A typical gap 34 size in an area with a ceiling height of approximately eight feet may be approximately 0.04 inches. Gap 34 may be increased to approximately 0.26 inches in an area with a ceiling height of approximately nine feet. In a larger area, with higher ceilings, fixture 200 may be configured with large gaps 134 (see FIGS. 21A-21D) where sterilization of the air in a larger area may be advantageous. A larger gap 134 will allow more air flow into sterilization chamber 104 for more sterilization of air flowing in the room. Gap 134 will also allow more UV-C radiation to leave fixture 200 sterilize more of the air surrounding fixture 200. The higher placement of fixture 200 due to the higher ceiling in the larger area will help ensure the increased UV-C radiation being expelled by fixture 200 will not be harmful to humans or animals. Gap 134 size in an area with a ceiling height of approximately 10 feet may be approximately 0.6 inches. Gap 134 may be increased to approximately 0.91 inches in an area with a ceiling height of approximately 20 feet.

The surface area of male pegs 56, 76 are sized to engage and seat at shoulders 126 of female posts 72 of louvers 22 and shoulders 98 of female posts 42. Pegs 56, 76, posts 74, 42 and shoulders 126, 98 are designed as sized to carry the compressive load created by the tightening of fasteners 30, 32 to dowel 24. Female posts 42, 72 are designed to be at a minimum cross-sectional area to carry the compressed loads of fixture 10 while enabling a maximum amount of airflow to pass through fixture 10 for sterilization of as much airflow as possible. The minimal cross-sectional area of female posts 42, 72 is also minimized to block or absorb a small percentage of the UV-C radiation leaving fixture 10 (approximately 20% of the UV-C radiation produced by bulb 26 may be absorbed with fixture 10 having a typical gap of 0.04 inches). Pegs 56, 76 and posts 74, 42 are positioned on base 18, louvers 22 and top end cap 16 to enable apertures 82, 112 to align and allow the passage of bulb 26 though fixture 10.

Figure 14A:
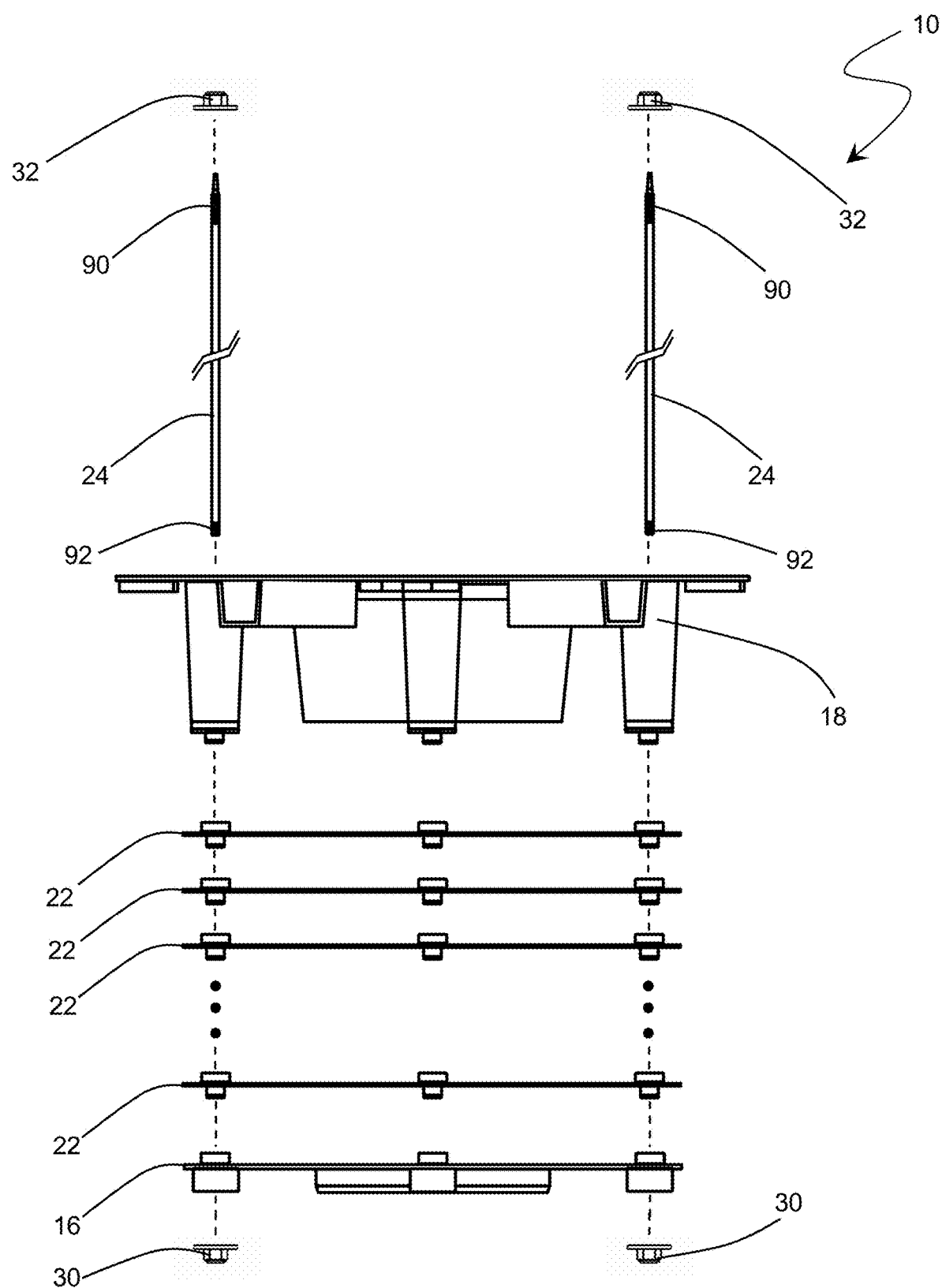

Now referring to FIG. 14A, fixture 10 may be assembled in the following manner. Fasteners 32 may be secured to first threaded end 90 of dowel 24. Second threaded end 92 of dowel 24 may be introduced into holes 86 of male pegs 56 of pillars 50 from an underside 94 of base 18 such that fastener 30 engages shoulder 120 of hole 86 to secure dowel 24 to base 18. Dowel 24 will extend outward from pillars 50 and upper surface 48 of base 18. With dowels 24 positioned and secure at each of holes 86, louvers 22 may be added to fixture 10.

Each of holes 88 of female post 72 and male peg of 76 of louver 22 may be aligned to dowels 24. Dowels 24 may be introduced into holes 88 such that dowels 24 pass freely through holes 88 and louver 22 may be slid toward base 18 as illustrated in FIG. 14A. As louver 22 approaches base 18, female post 72 of louver 22 will engage male peg 56 of pillar 50 and base 18. As described above, male pegs are sized to nest within female posts when fixture 10 is assembled. Male peg 56 will nest within well 124 of female post 72 and limit the lateral motion of louver 22 relative to base 18 as louvers 22 are added to the assembly of fixture 10. With the first louver 22 in position on base 18, additional louvers 22 may be added in the same manner as described above to add the first louver 22 to the base 18. Male peg 76 will nest within well 124 of female post 72. Louvers 22 are designed to be stackable on base 18 and onto subsequent louvers 22.

Figure 16:
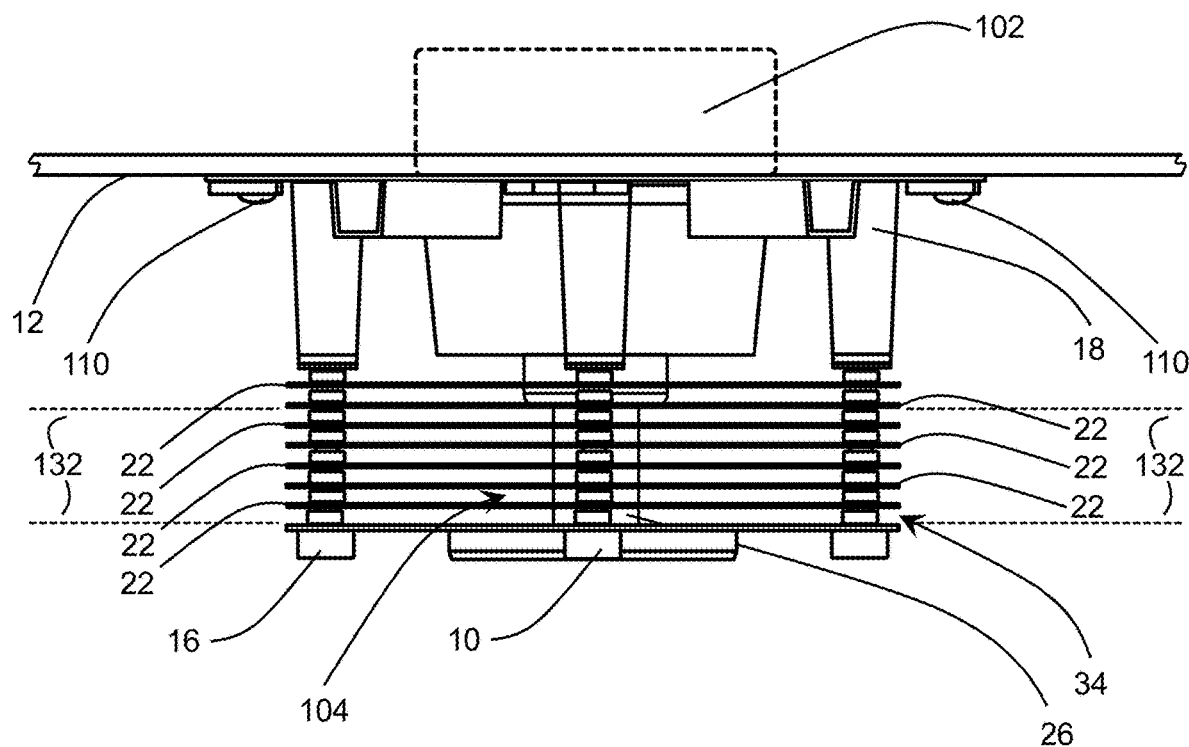
Figure 17:
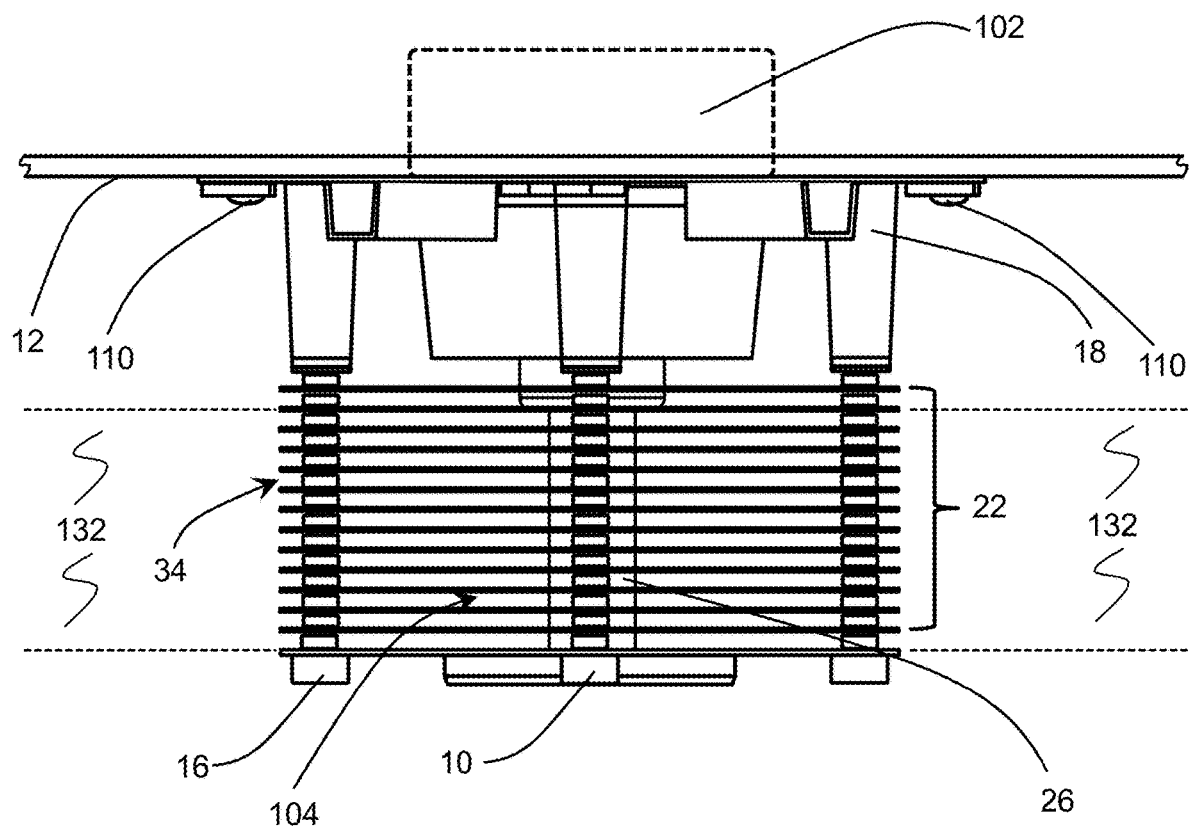
Figure 18:
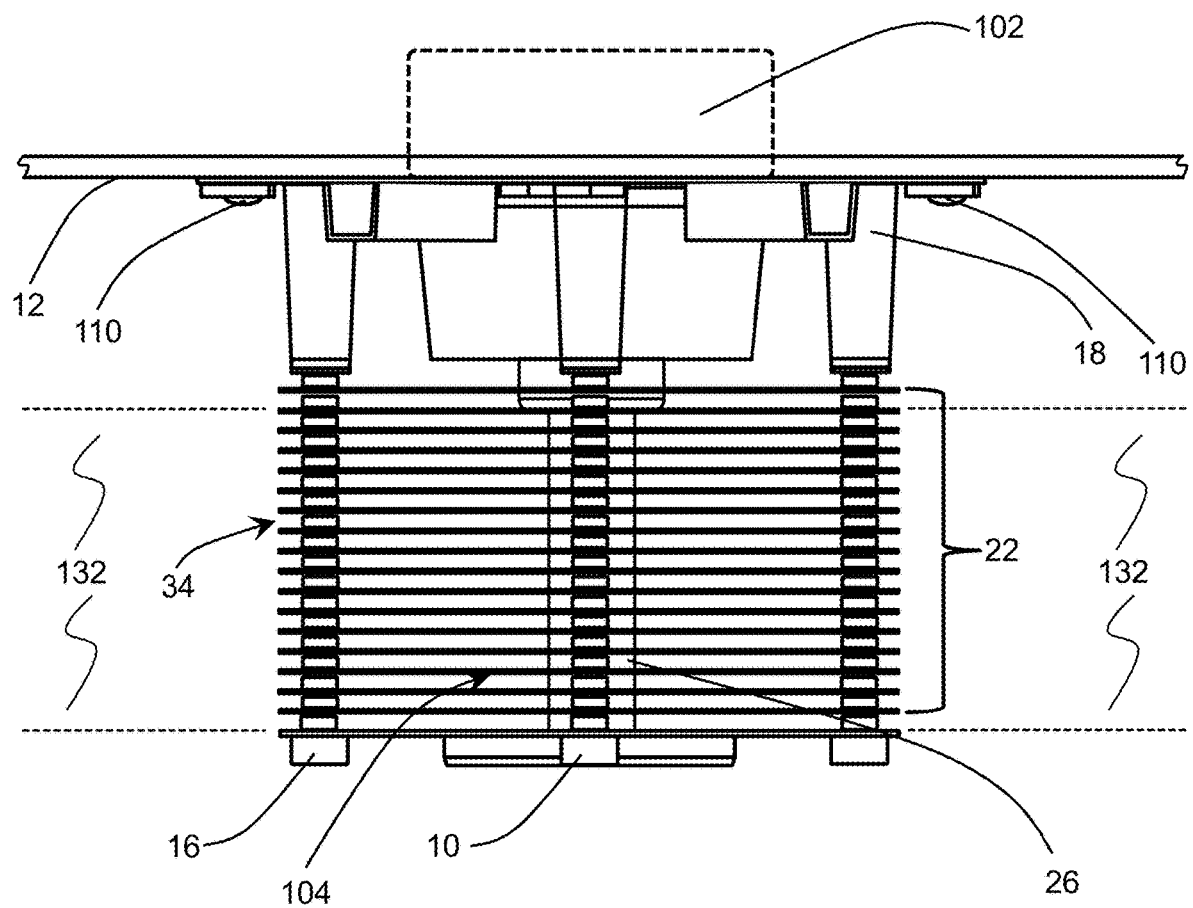
Figure 19:
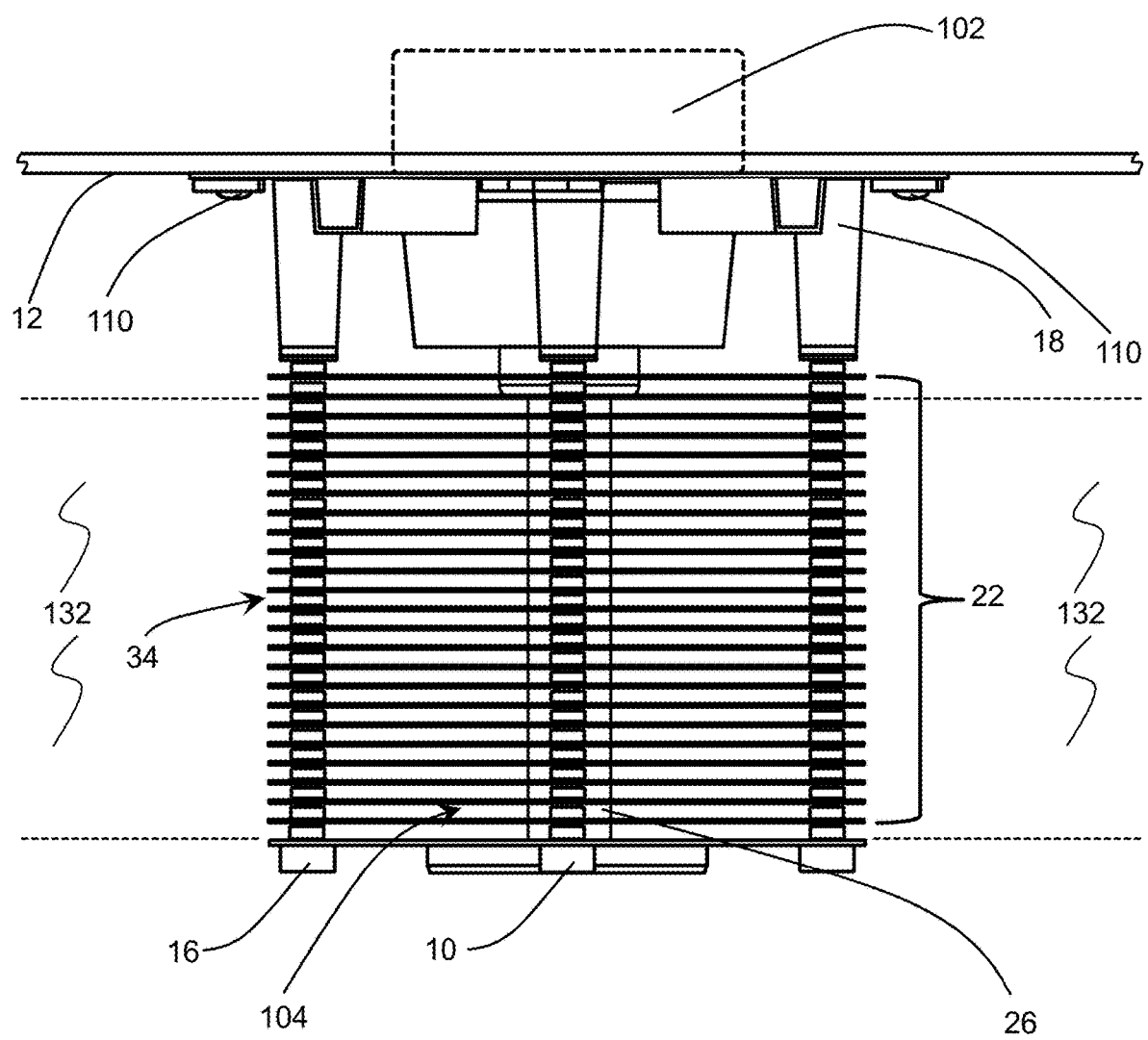
Figure 20:
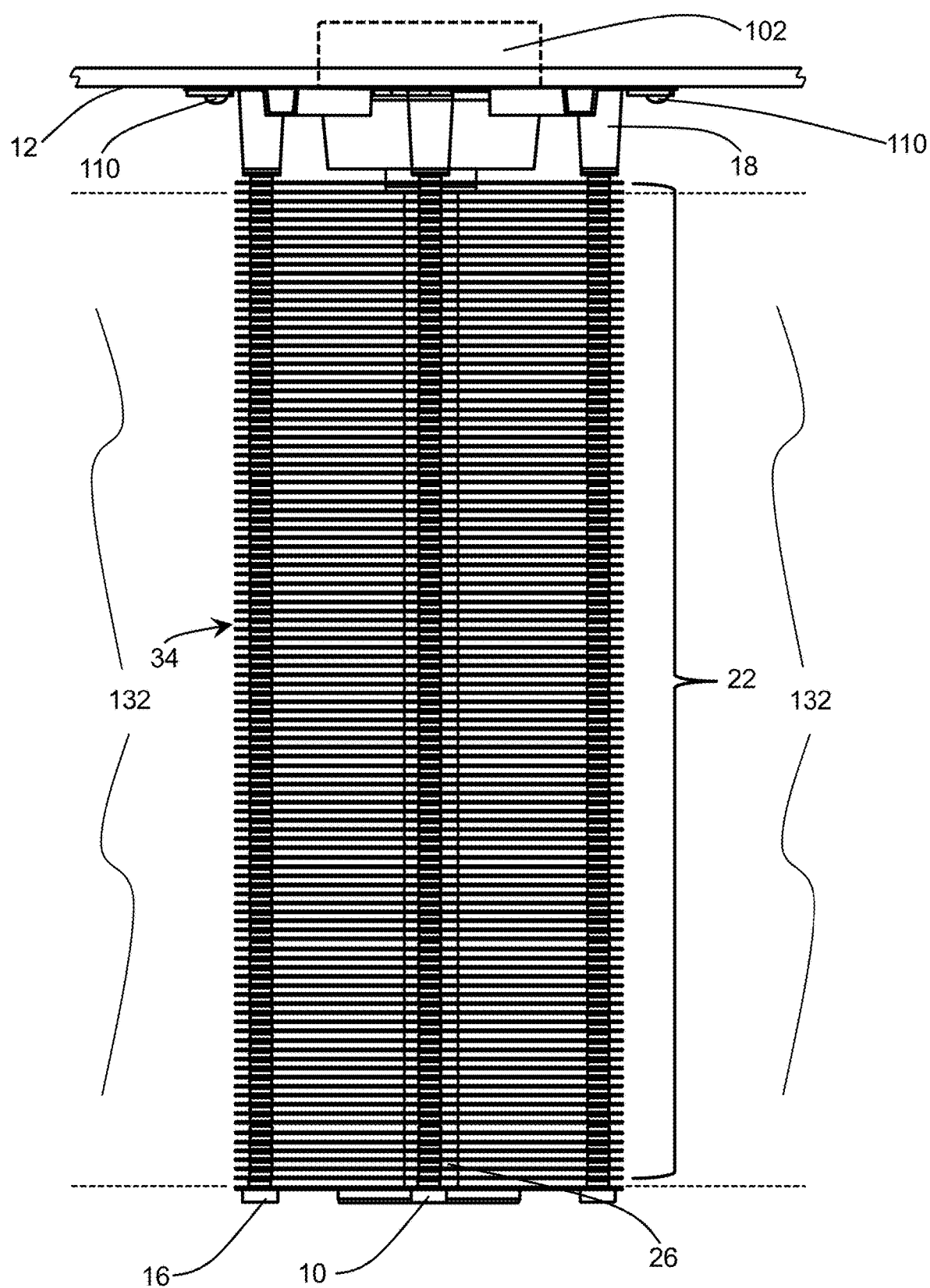

The number of louvers 22 will be dictated by the size of bulb 28. Larger bulbs 28 will generate a higher intensity of UV-C radiation. The design flexibility of fixture 10 to adapt to a number of different sized bulbs will enable fixture 10 to be used in a number of different areas and a variety of different sized and shaped rooms. FIGS. 16-20 illustrate different sizes of fixtures 10 to accommodate the different bulb lengths. The differences between each of the fixtures depicted in the different drawing figures may be attributed to the number of louvers 22 and the length of dowels 24. A single top end cap 16 and a single base 18 may be used. FIG. 16 illustrates fixture 10 that may be used with a light emitting diode (LED) type UV-C bulb and seven louvers 22. FIG. 17 depicts fixture 10 that may be used with a 15-watt UV-C bulb and 13 louvers. FIG. 18 illustrates fixture 10 that may be used with a 25-watt UV-C bulb and 17 louvers and may continuously sterilize approximately 400 cubic feet of air while the UV-C lamp is operating. FIG. 19 depicts fixture 10 that may be used with a 36-watt UV-C bulb and 24 louvers and may continuously sterilize approximately 600 cubic feet of air while the UV-C lamp is operating. FIG. 20 illustrates fixture 10 that may be used with a UV-C bulb that may be 36 inches in length and 110 louvers for large area such as manufacturing plants, sports arenas and gyms, large box stores and other areas with high ceilings and may continuously sterilize approximately 1,800 cubic feet of air while the UV-C lamp is operating.

No referring back to FIG. 14A, with the desired louvers 22 in place for the specified size of lamp 26, top end cap 16 may be added and secured to fixture 10. Holes 84 of female posts 42 and fastener seats 40 may be aligned to dowels 24. Dowels 24 may be introduced into holes 84 such that dowels 24 pass freely through holes 84 and top end cap 16 may be slid toward the top louver 22. As top end cap 16 approaches louver 22, female post 42 of top end cap 16 will engage male peg 76 of louvre 22. As described above, male pegs 76 are sized to nest within female posts 42 and engage shoulder 98 of well 96 when fixture 10 is assembled. With top end cap 16 in position on louver 22, fasteners 30 may be added to second end 92 of dowel 24 to secure fastener 30 to dowel 24. As fastener 30 is secured to dowel 24, fastener 30 will engage shoulder 118 of fastener seat 40 to finally secure base 18, a plurality of louvers 22 and top end cap 16 together to create fixture 10.

Figure 14B:
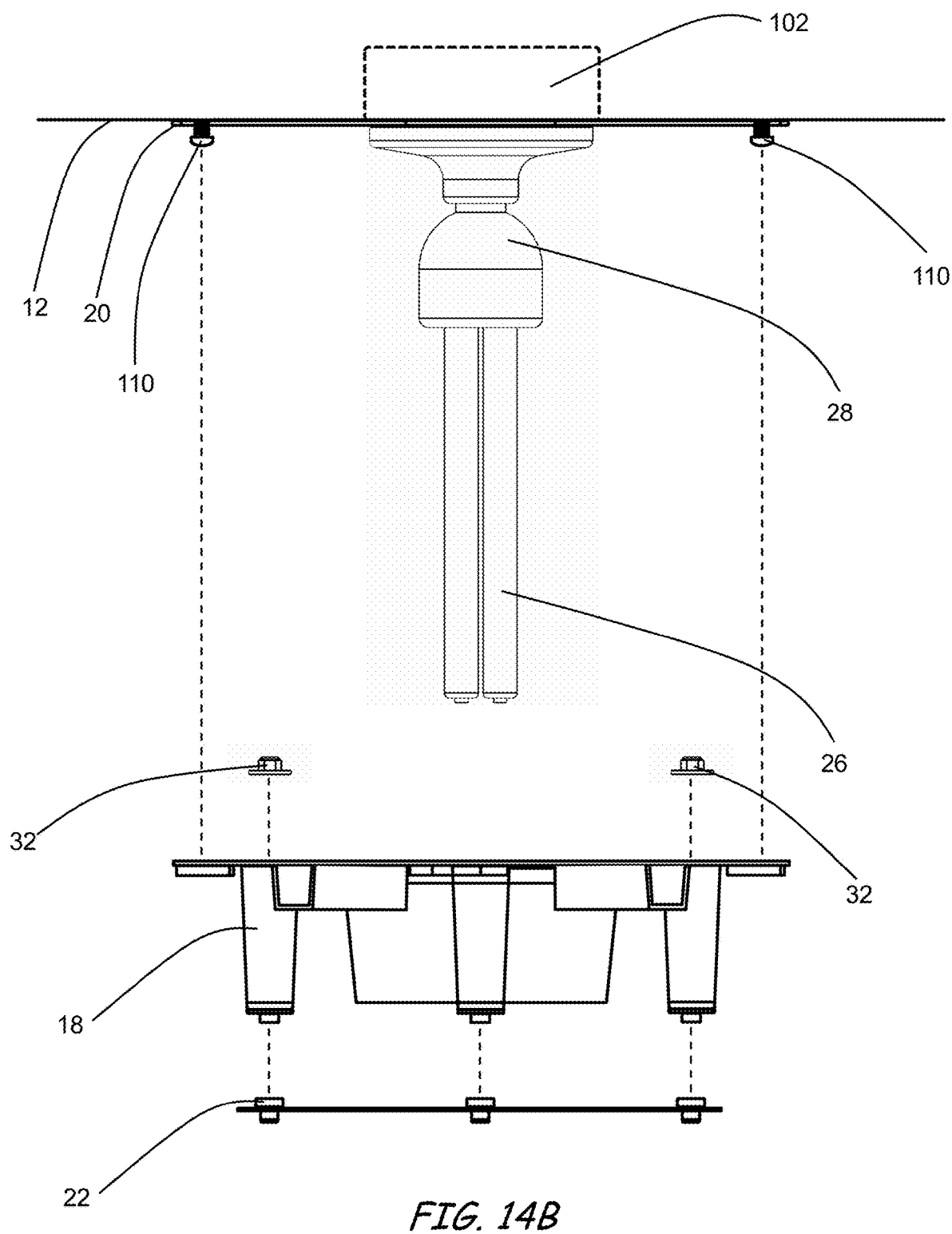
Figure 14C:
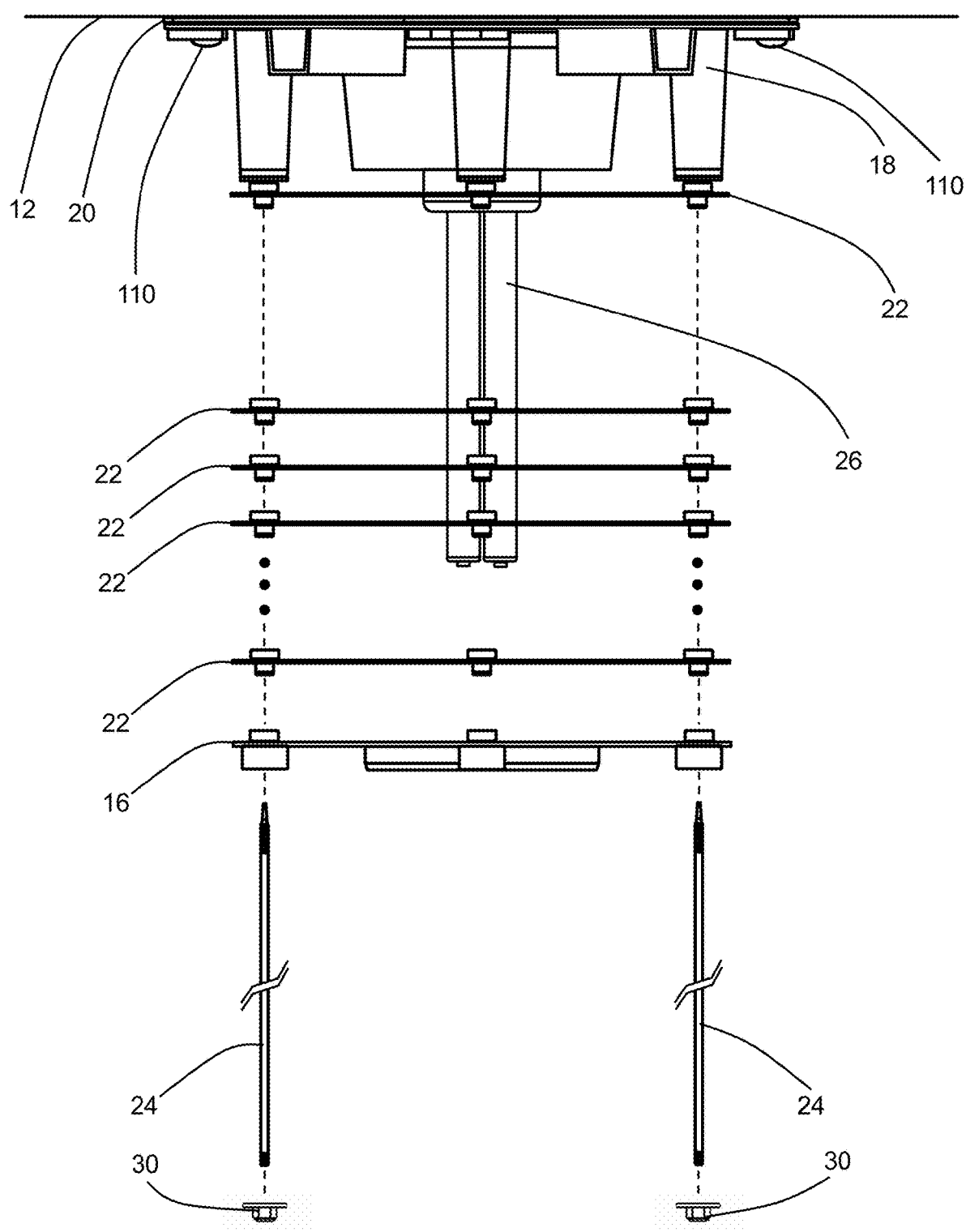
Figure 15A:
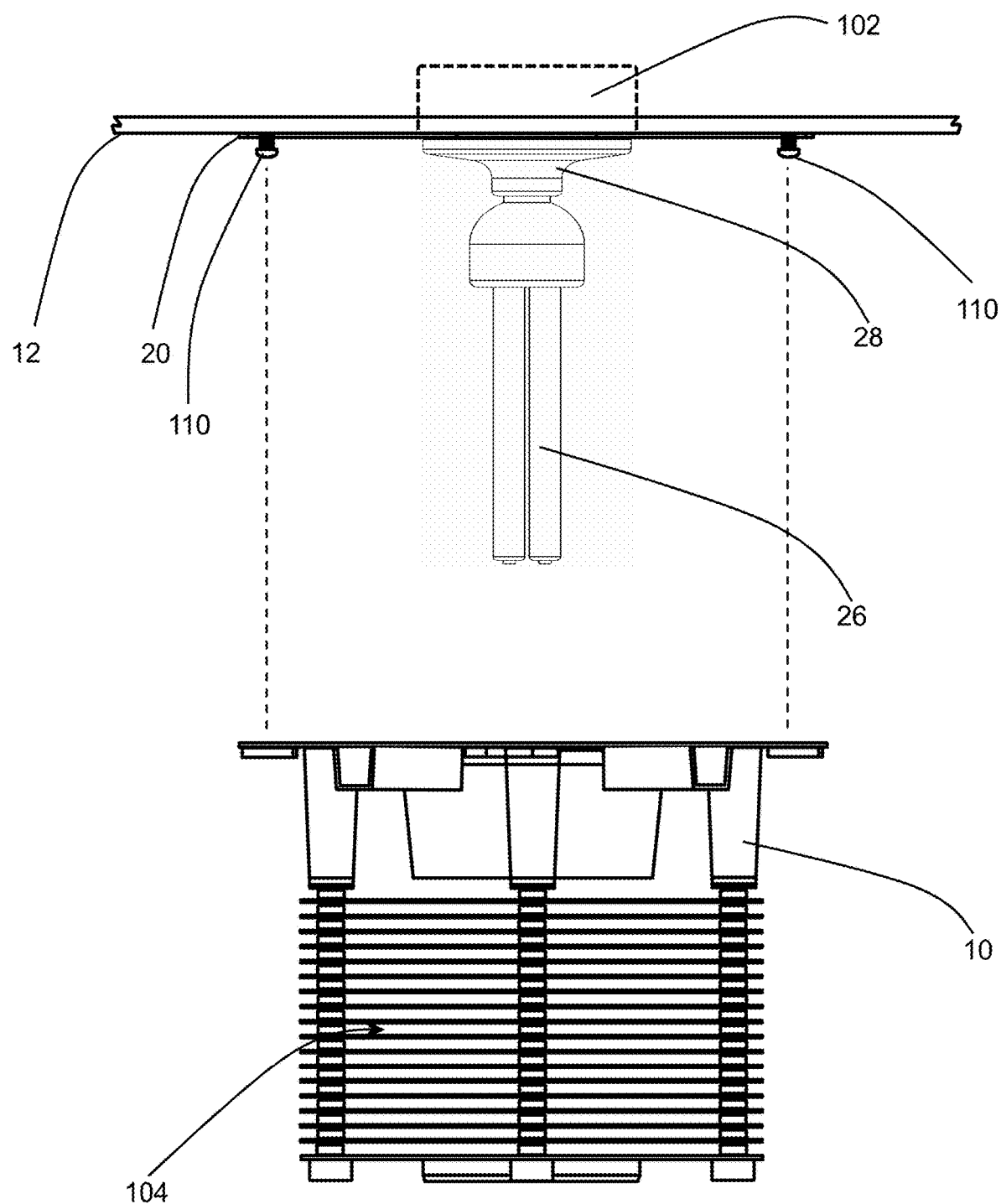

FIGS. 14B and 14C illustrate the exploded view of fixture 10 being assembled to mounting plate 20 that is secured to ceiling 12. Base 18 may be assembled to mounting plate 20 with fasteners 110 as described above. Fasteners 110 may be any type of fasteners such as a bolt, screw, hurricane bolt and the like, and fastened to mounting plate 20 and ceiling 12. FIG. 15A depicts fixture 10 being secured to ceiling 12 with mounting plate 20 and fasteners 110. In this particular assembly, bulb holder 28 and bulb 26 have been secured to mounting plate 20, electrical box 102 and ceiling 12. The electrical wiring to operate bulb 26 from box 102 may be passed through aperture 70 of plate 20 and assembled to bulb holder 28. Fixture 10 assembly may be slid over bulb 26 and holder 28. Holes 62 of base 18 may be aligned to accept fasteners 110 to secure fixture 10 to plate 20 and ceiling 12 to enable the use of bulb 26 with fixture 10.

Figure 14D:
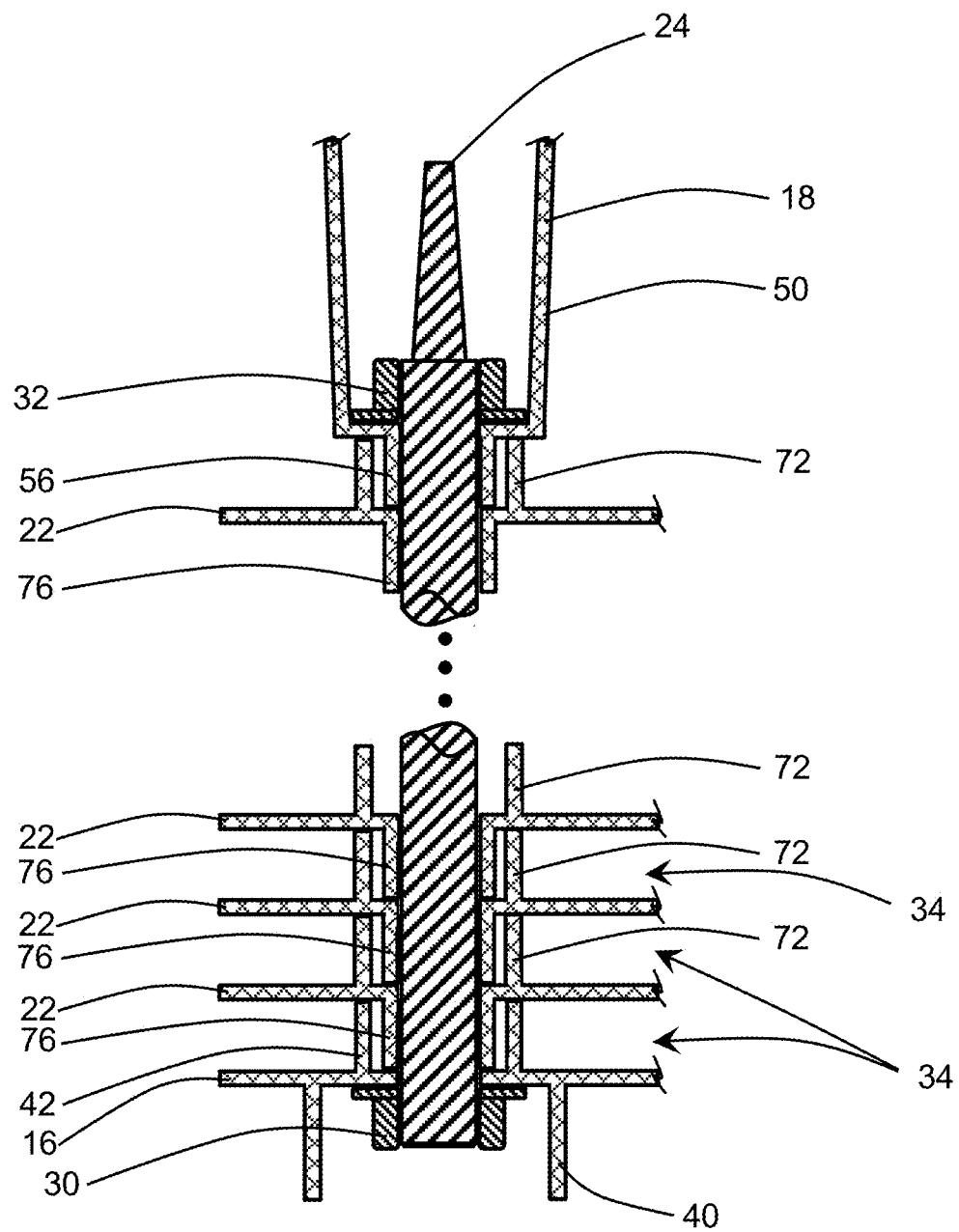

FIG. 14D is an enlarged cross-sectional view of top end cap 16, louver 22, pillar 50 of base 18 and dowel 24. FIG. 14D illustrates how male pegs 76 are nested within female posts 72 of louvers 22 to create gap 34 when fixture 10 is fully assembled. Male pegs 56 of pillar 50 is also nested into female posts 72 of louvers 22 to position base 18 and louver 22. Male pegs 76 of lover 22 is nested into female posts 42 of top end cap 16 to position top end cap 16 and louver 22. Dowel 24 and fasteners 30, 32 are added to secure base 18, louvers 22 and top end cap 16 to create fixture 10.

Figure 15B:
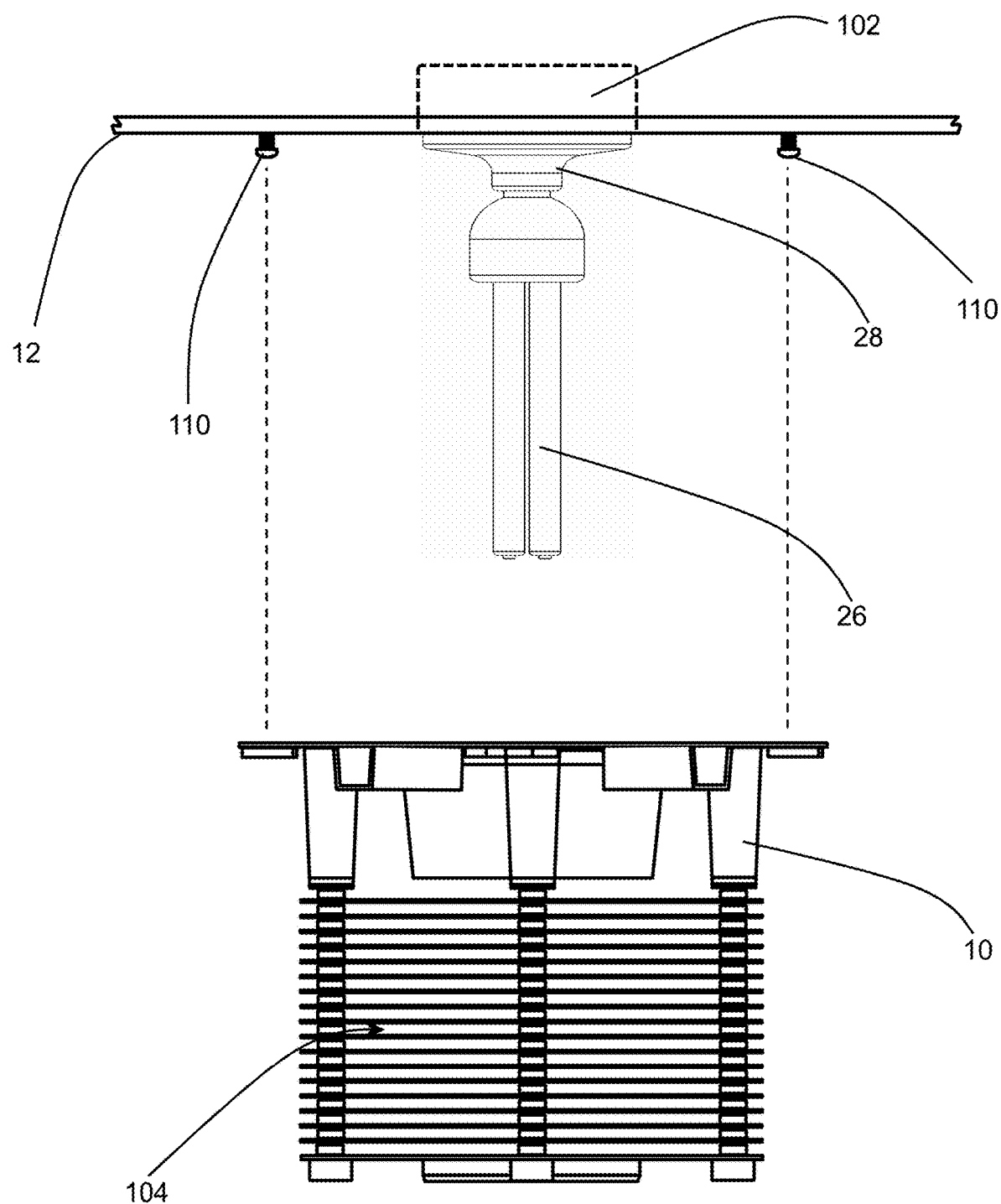
Figure 15C:
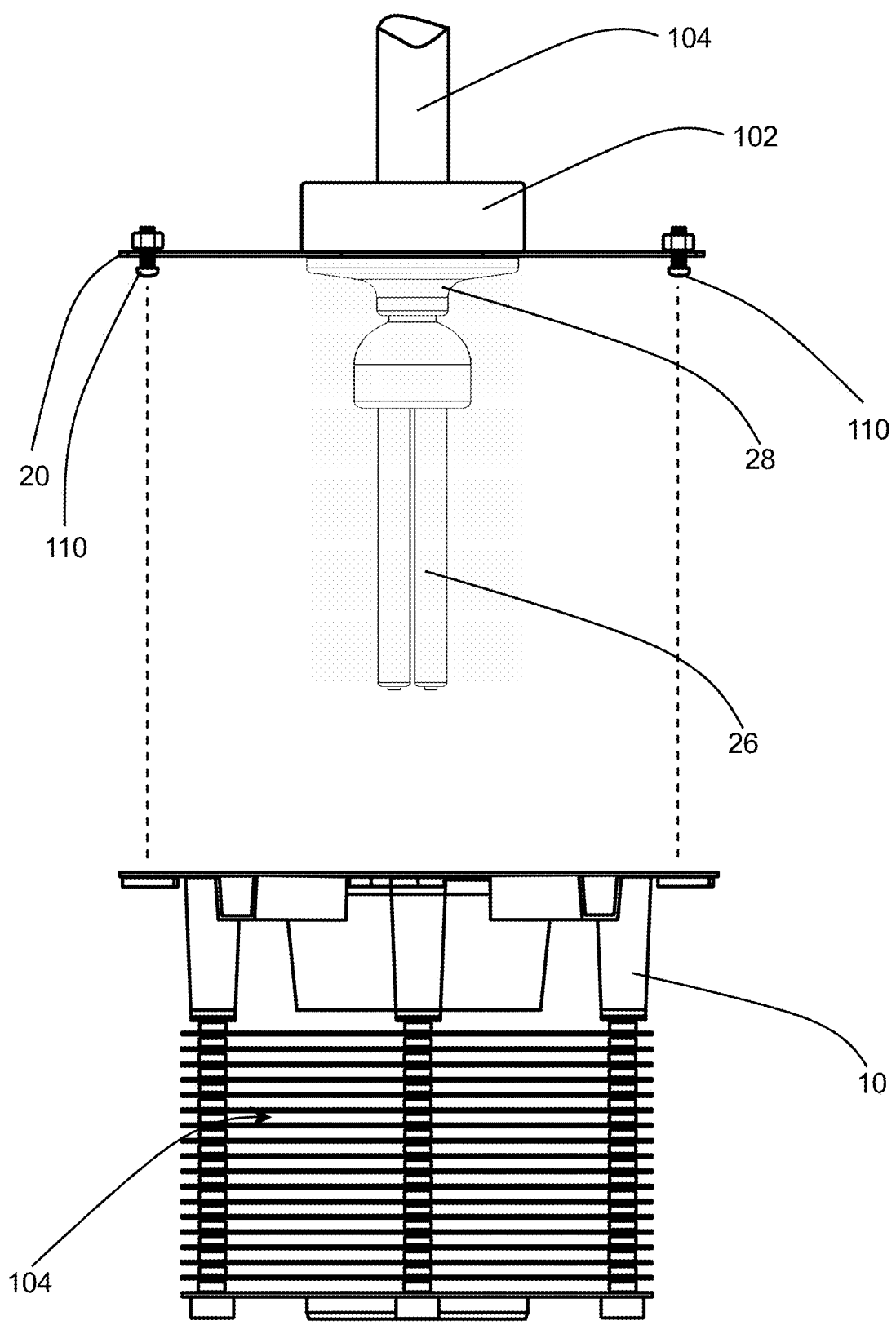
Figure 15D:
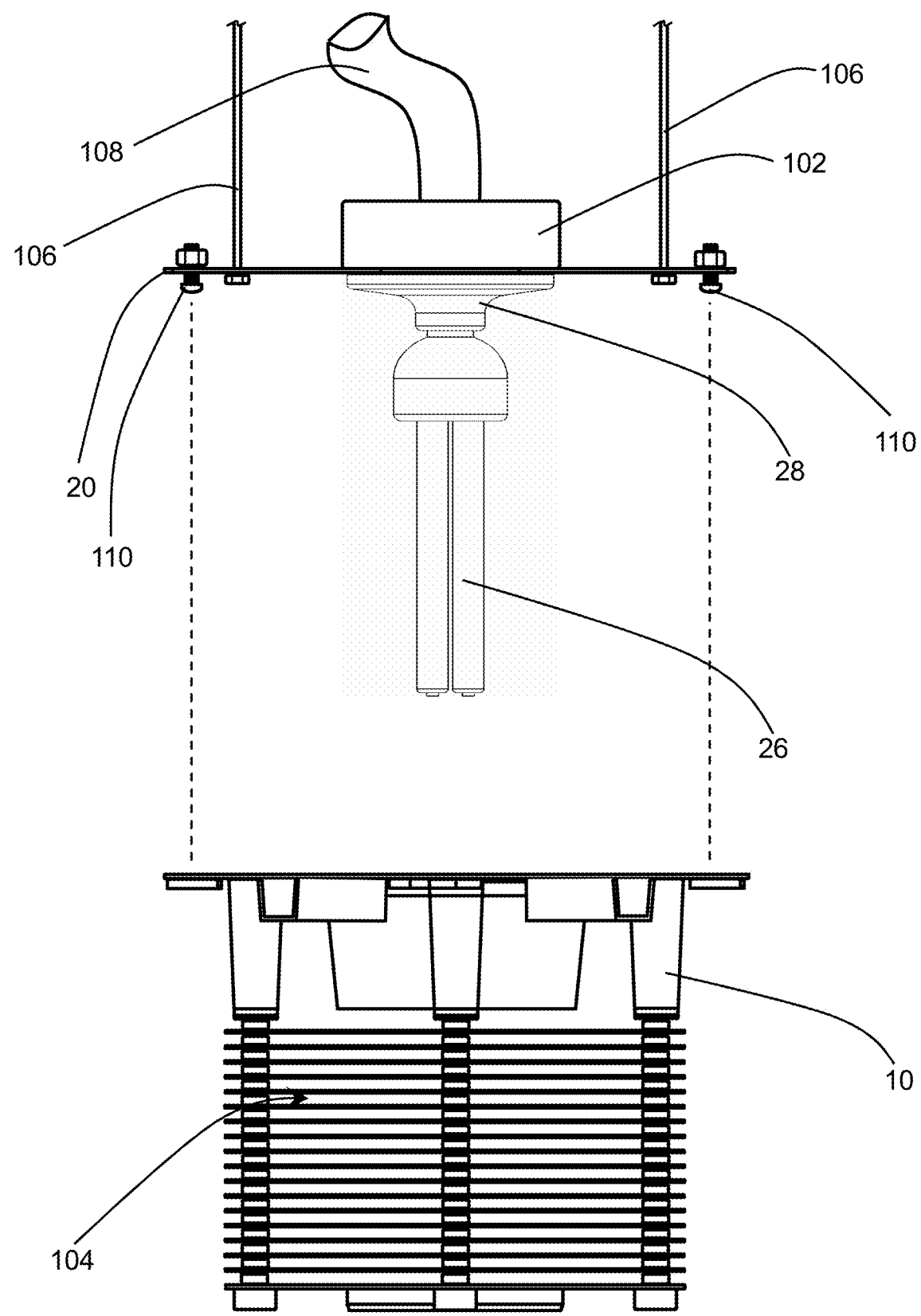

FIGS. 15B-15D portray alternative means to mount fixture 10 within the room of a building or a structure. FIG. 15B illustrates the assembly of fixture 10 directly mounted to ceiling 12 without the use of mounting plate 20. Fasteners 110, as stated above, may be any type of fasteners such as a bolt, screw, hurricane bolt and the like, and may be fastened directly to ceiling 12 without the use of mounting plate 20. Bulb holder 26 may be assembled directly to electrical box 102. In this particular assembly, bulb holder 28 and bulb 26 have been secured to electrical box 102 and ceiling 12. Fixture 10 assembly may be slid over bulb 26 and holder 28. Holes 62 of base 18 may be aligned to accept fasteners 110 to secure fixture 10 to ceiling 12 to enable the use of bulb 26 with fixture 10.

FIG. 15C illustrates the assembly of fixture 10 directly mounted to mounting plate 20. This type of assembly may be used in structures or buildings with high ceilings. Support for fixture 10, mounting plate 20, bulb 26, bulb holder 28 and box 102 may rely on a conduit 104 that extends from a high ceiling a length downward to an acceptable height for the dispersion of UV-C radiation. Conduit 104 extends from the electrical source to electrical box 102 to carry the electrical wiring to bulb holder 28 to energize bulb 26. In this particular assembly, bulb holder 28 and bulb 26 have been secured to mounting plate 20 and box 102. Fixture 10 assembly may be slid over bulb 26 and holder 28. Holes 62 of base 18 may be aligned to accept fasteners 110 to secure fixture 10 to plate 20 to enable the use of bulb 26 with fixture 10 at the desired height within the area.

FIG. 15D illustrates the assembly of fixture 10 directly mounted to mounting plate 20. This type of assembly may be used in structures or buildings with high ceilings as well. Support for fixture 10, mounting plate 20, bulb 26, bulb holder 28 and box 102 may rely on a plurality of support cables 106 that extend from a high ceiling a length downward to an acceptable height for the dispersion of UV-C radiation. A flexible conduit 108 extends from the electrical source to electrical box 102 to carry the electrical wiring to bulb holder 28 to energize bulb 26. In this particular assembly, bulb holder 28 and bulb 26 have been secured to mounting plate 20 and box 102. Fixture 10 assembly may be slid over bulb 26 and holder 28. Holes 62 of base 18 may be aligned to accept fasteners 110 to secure fixture 10 to plate 20 to enable the use of bulb 26 with fixture 10 at the desired height within the area.

Figure 21A:
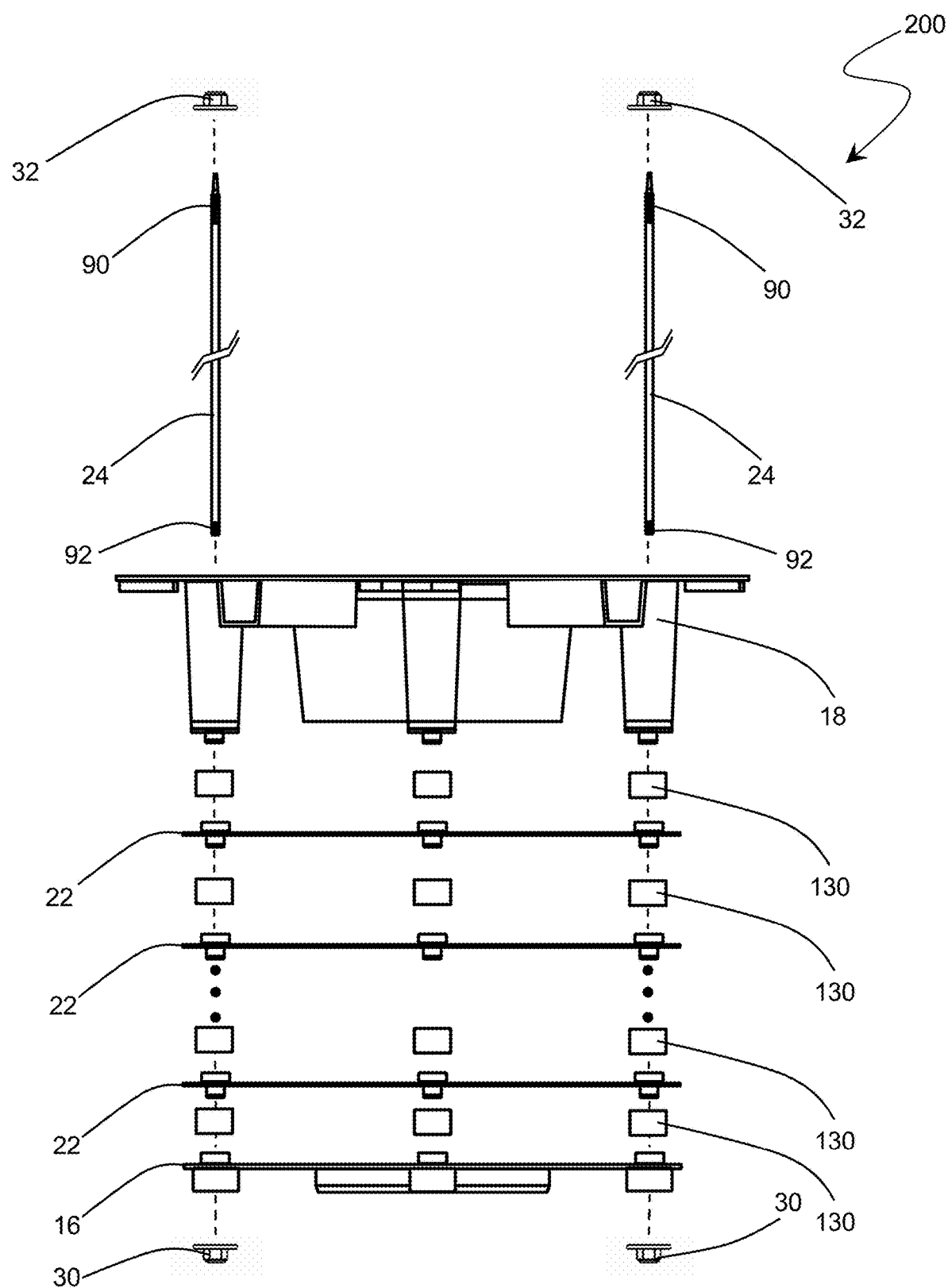
Figure 21B:
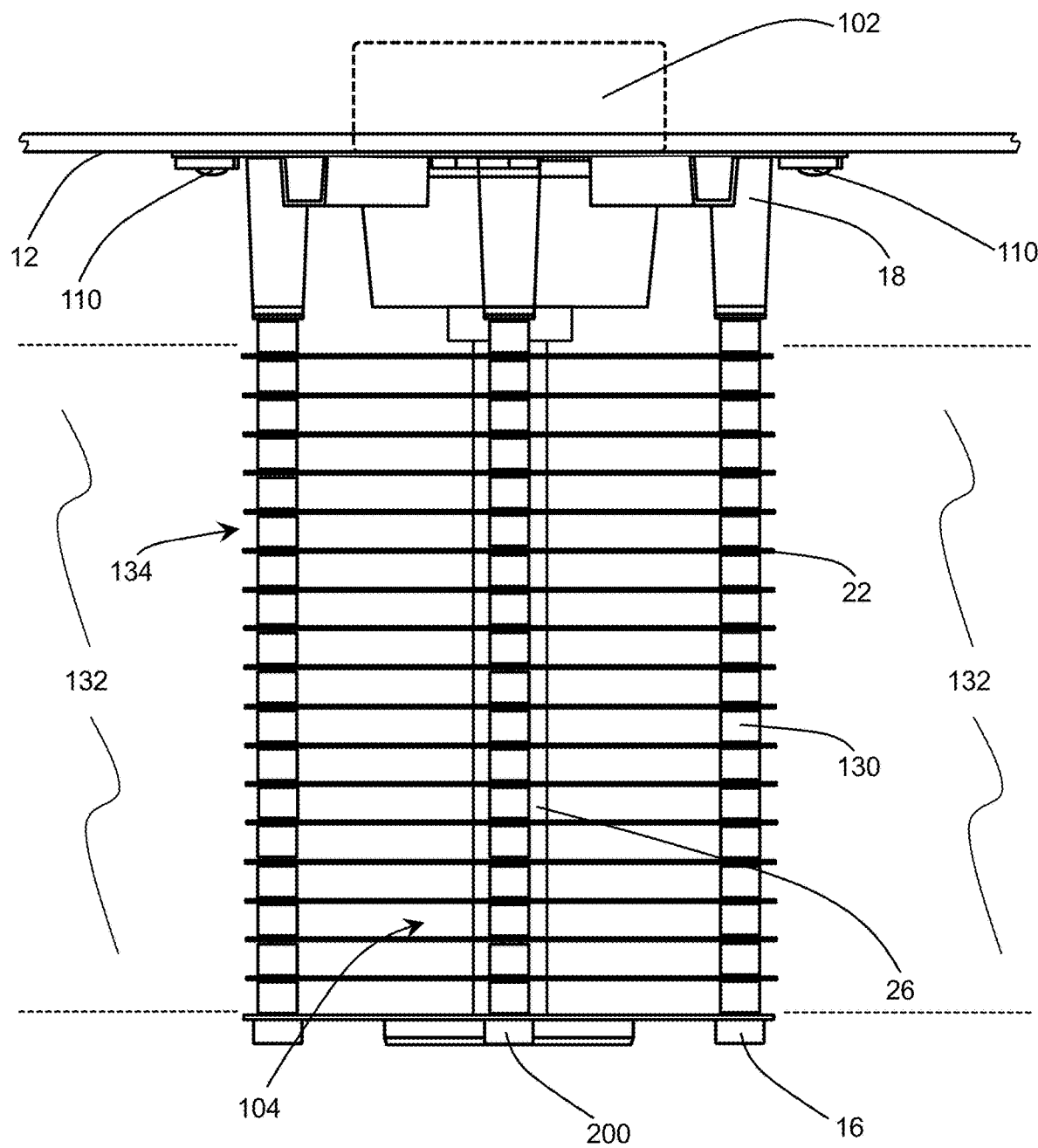
Figure 21C:
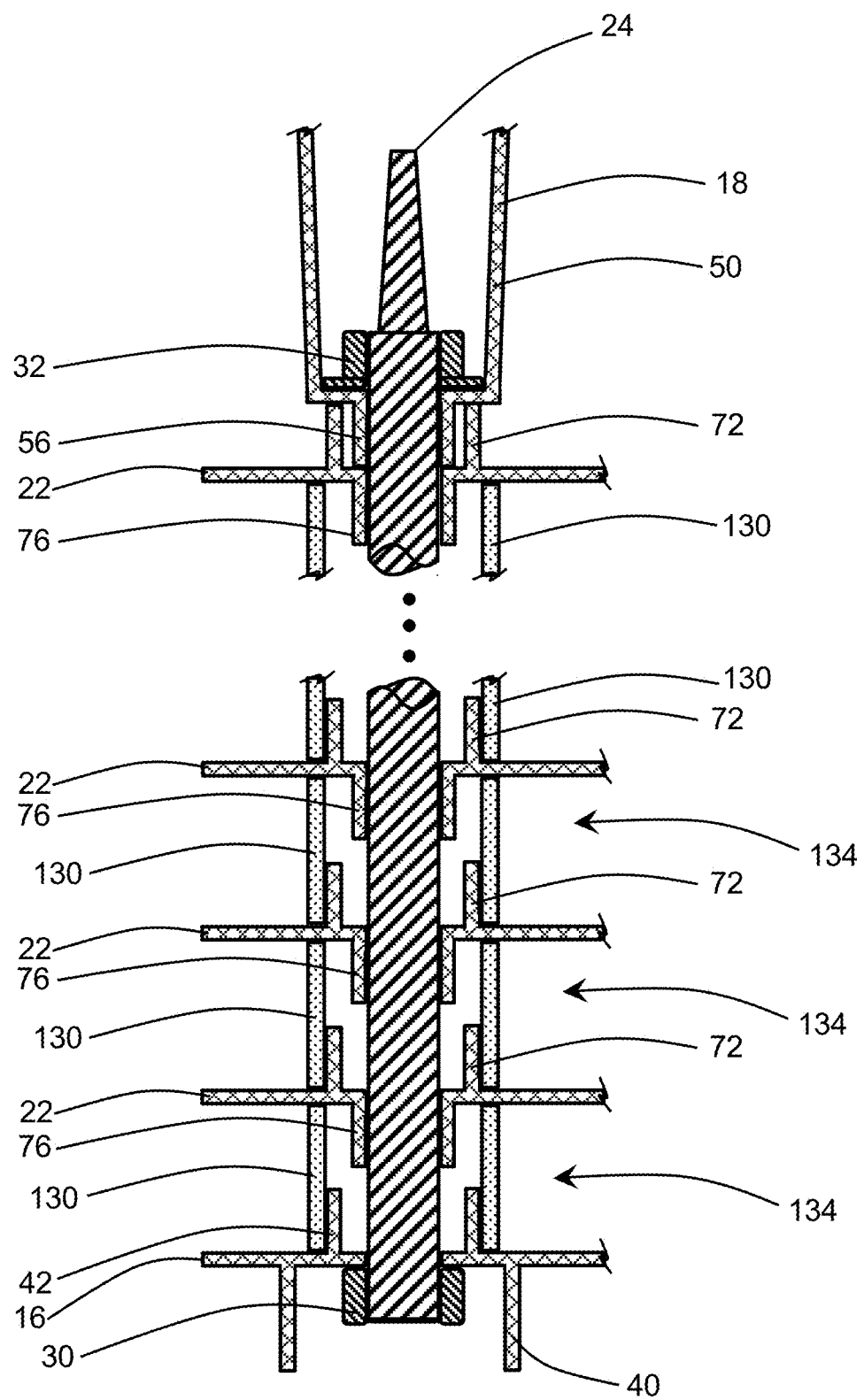

FIGS. 21A-21C illustrate fixture 200 according to another embodiment of the present invention. In this particular embodiment of the present invention, sleeves 130 may be added to fixture 200 to create gap 134. Gap 134 will be a wider gap than gap 34 of fixture 10 to allow more air to flow into sterilization chamber 104 and allow more UV-C radiation to be expelled from fixture 200. As described above, fixture 200 may be used in areas with higher ceilings to help ensure any increase in UV-C radiation being expelled from fixture 200 will not harm any humans or animals. Typically, fixture 200 may be used in areas having a ceiling height of approximately 10 feet or higher. Allowing more air into sterilization chamber 104 and more UV-C radiation out of fixture 200 will enable fixture 200 to sterilize a wider area and eradicate the air of any pathogens, viruses and bacterias.

Figure 21D:
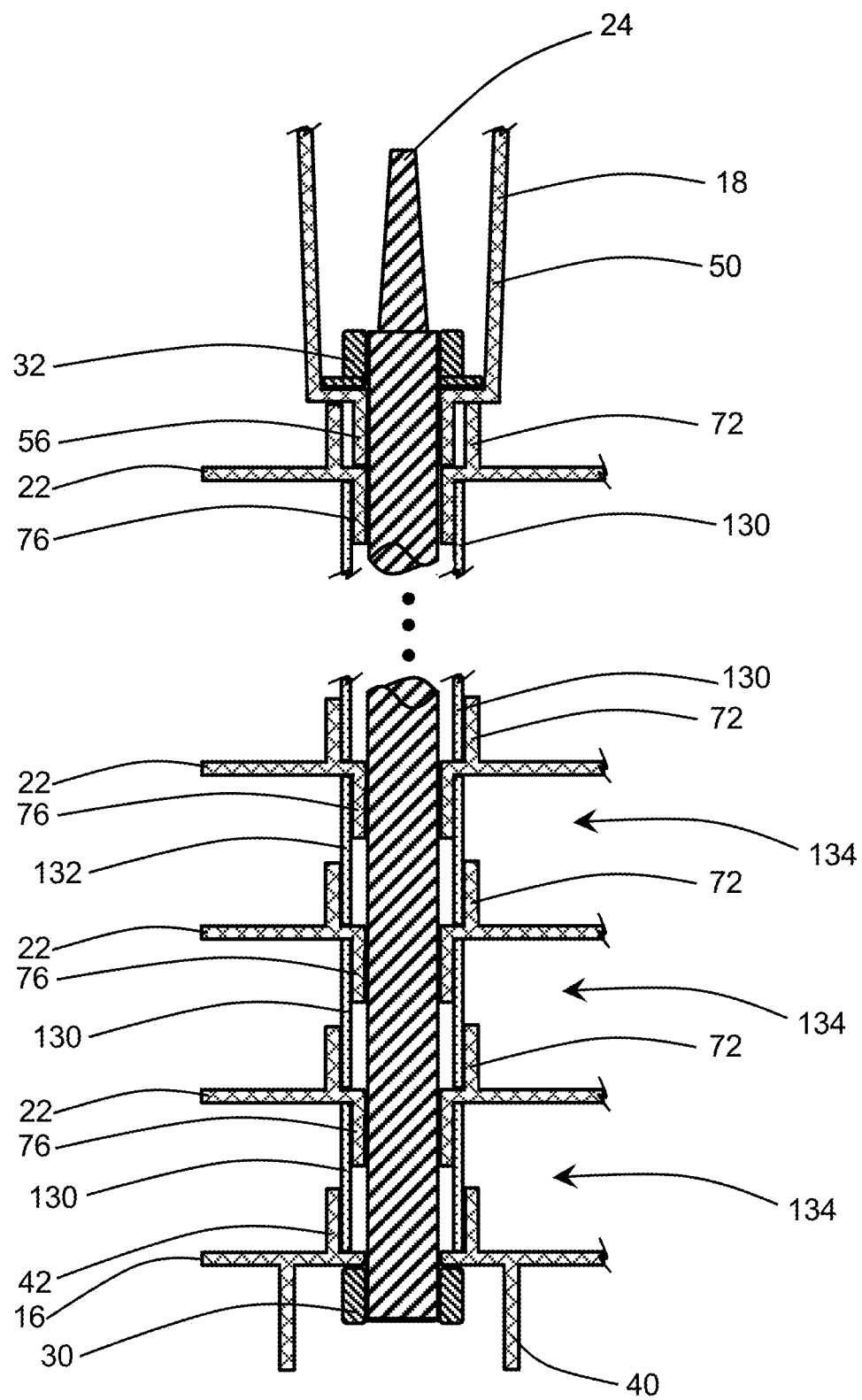

Sleeve 130 may be positioned at the outside diameter of female posts 42 of top end cap 16 and female posts 72 of louvers 22 and secured between base 18, louvers 22 and end cap 16 to create gap 134 when dowel 24 and fasteners 30, 32 are positioned and secured to create fixture 200 as illustrated in FIG. 21C. Alternatively, sleeve 130 may be positioned at the inside diameter of female posts 42 of top end cap 16 and female posts 72 of louvers 22 and the outside diameter of male pegs 56 of pillar 50 and male pegs 76 of louvers 22. Sleeve 130 may be secured between base 18, louvers 22 and end cap 16 to create gap 134 when dowel 24 and fasteners 30, 32 are positioned and secured to create fixture 200 as illustrated in FIG. 21D.

In this particular embodiment of the present invention, sleeves 130 may be generally round/cylindrical in shape. However, it is important to note, that sleeves 130 may designed in any shape, such as oval, rectangular, triangular, and the like and still maintain the function of fixture 200. Sleeves 130 may be manufactured of any material such as plastic, metal and the like. However, it is important to note, sleeve 130 may be manufactured from aluminum to reduce any absorption of UV-C radiation at sleeve 130 to ensure the maximum amount of UV-C radiation is being expelled from fixture 200 and used for the sterilization of the air proximate fixture 200.

Figure 22:
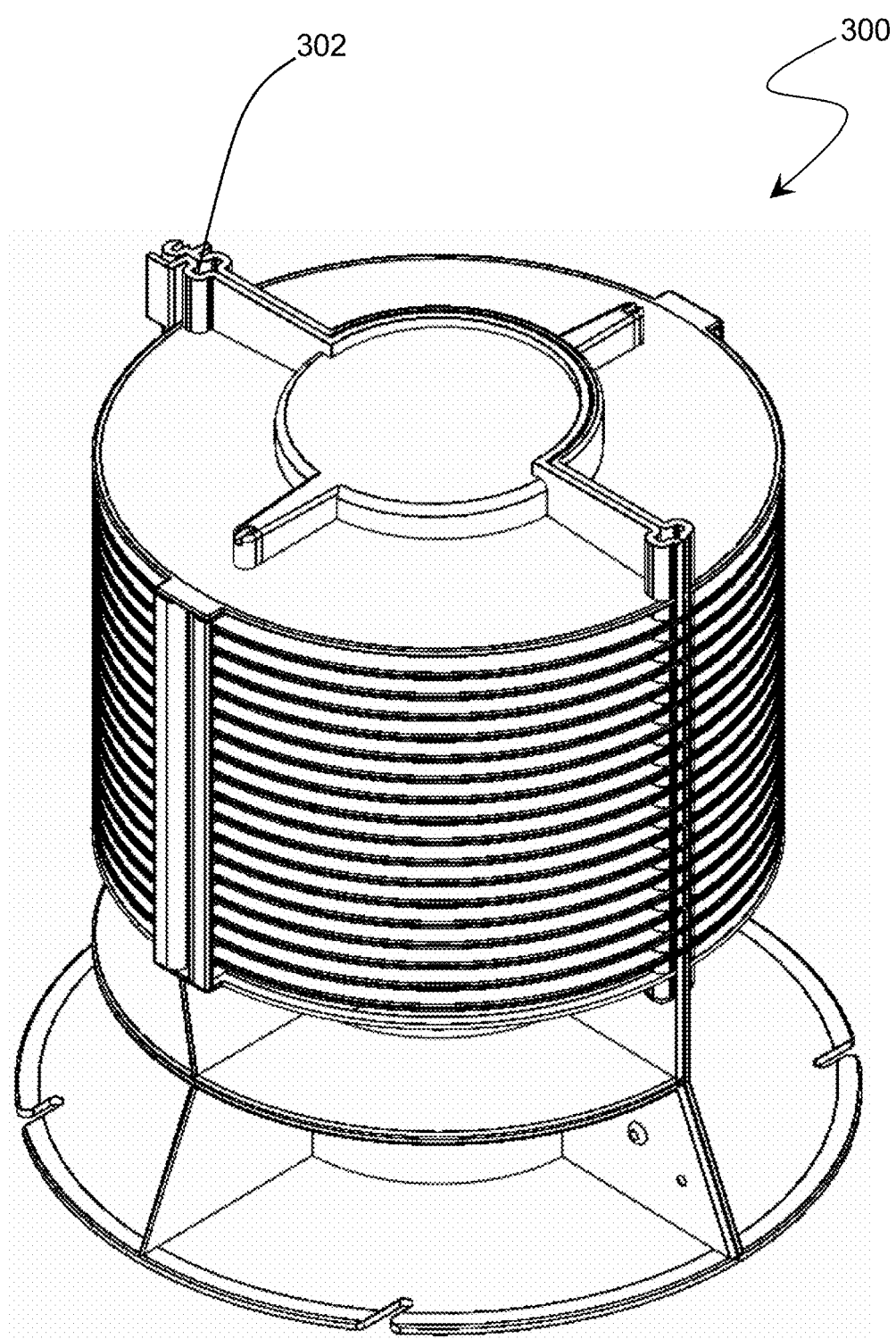
FIG. 22 is an isometric view of the ultraviolet light fixture according to yet another embodiment of the present invention.
Figure 23:
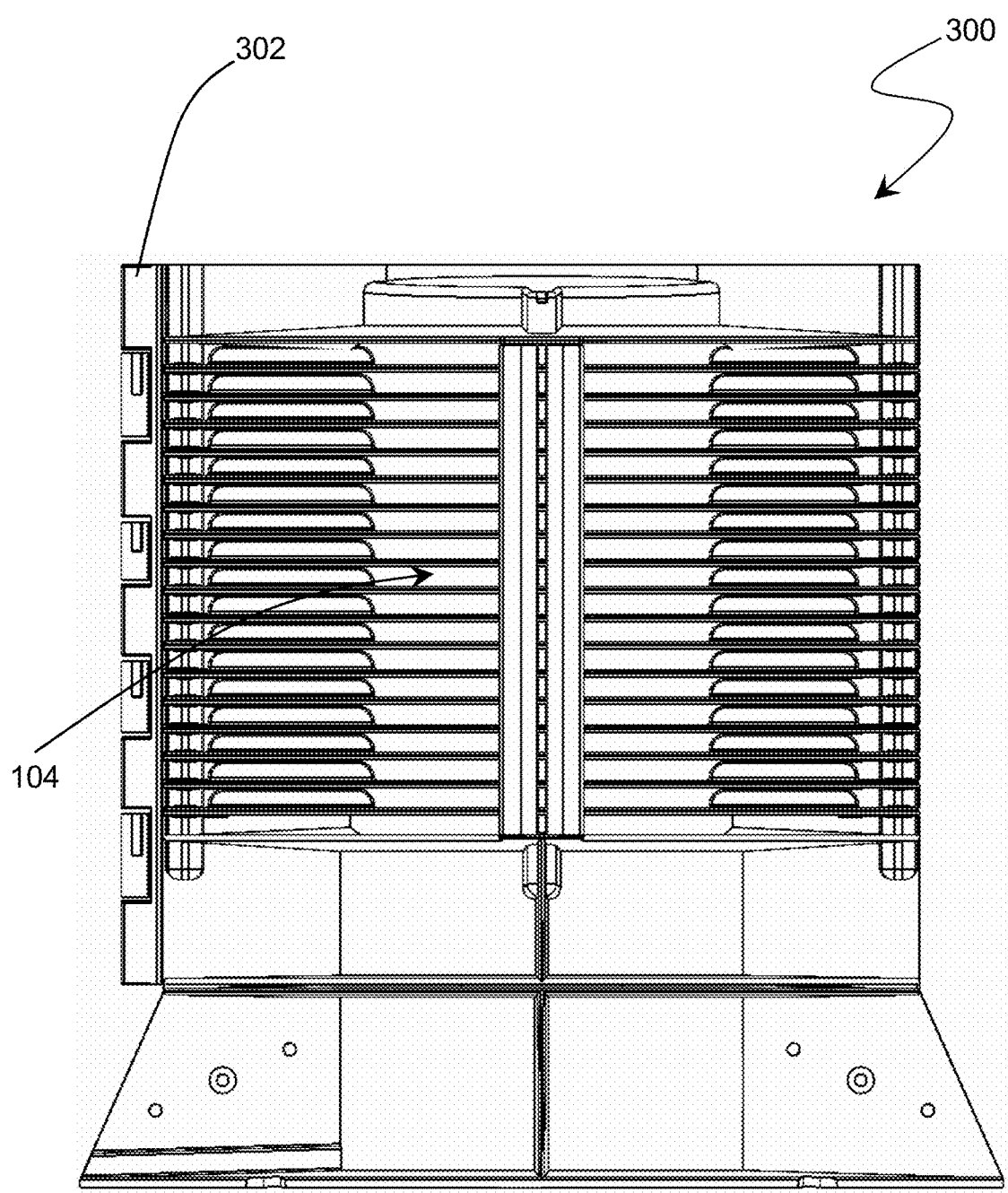
FIG. 23 is a plan view of the ultraviolet light fixture according to the embodiment of the present invention.

FIGS. 22 and 23 illustrate fixture 300 according to yet another embodiment of the present invention. Fixture 300 includes a similar louver and gap design as described with fixture 10 to enable air flow into and out of fixture 300 as well as allow UV-C radiation to extend outside of fixture 300. Fixture 300 further includes a hinge 302 to enable fixture 300 to be opened while not in operation to service bulb 28 if needed.

Fixtures 10, 200, 300 will provide the following advantages over the prior art. Each of mounting plate 20, base 18, louvers 22, top end cap 16 and dowels 24 are inexpensive to manufacture from inexpensive materials using inexpensive tooling and manufacturing means to produce each component and assemble the components to create fixture 10, 200, 300. Materials used in Fixture 10, 200, 300 enable a smaller and lighter fixture that is less expensive than prior art lamps and may be adapted for many uses. Fixture 10, 200, 300 enables a wide range of flexibility to be used with a number of different sized UV-C bulbs and in a variety of different areas or enclosures. Louvers 22 are stackable upon one another and may be added or removed from fixture 10, 200, 300 with ease to accommodate the different lengths of UV-C bulbs. Polished surfaces or reflective surfaces may be used in fixture 10, 200, 300, but are not required like they are in prior art UV-C lamps limit absorption of the UV-C radiation by the fixture. Nor are elaborate parabolic reflectors required as they are in prior art UV-C lamps to facilitate UV-C radiation outside of the lamp enclosure. Polished surfaces, reflective surfaces and elaborate parabolic reflectors add expense to the prior art UV-C lamps. Fixtures 10, 200, 300 may be configured for use with a number of different ceiling heights (see FIGS. 15A-15D) as well to ensure ample UV-C radiation to sterilize the air while maintaining the safety of the individuals in the area while the UV-C lamp is in operation. The size of gap 34, 134 will enable sufficient air flow into and out of sterilization chamber 104 of fixture 10, 200, 300 to maximize sterilization of the air flowing into and out of the lamp. At the same time, the size of gap 34, 134 will limit the amount of amount of UV-C light or radiation that is absorbed by fixture 10, 200, 300 thereby allowing more UV-C radiation to extend out past the fixture creating sterilization field 132 to sterilize any air that does not flow into fixture 10, 200, 300.

Figure 24:
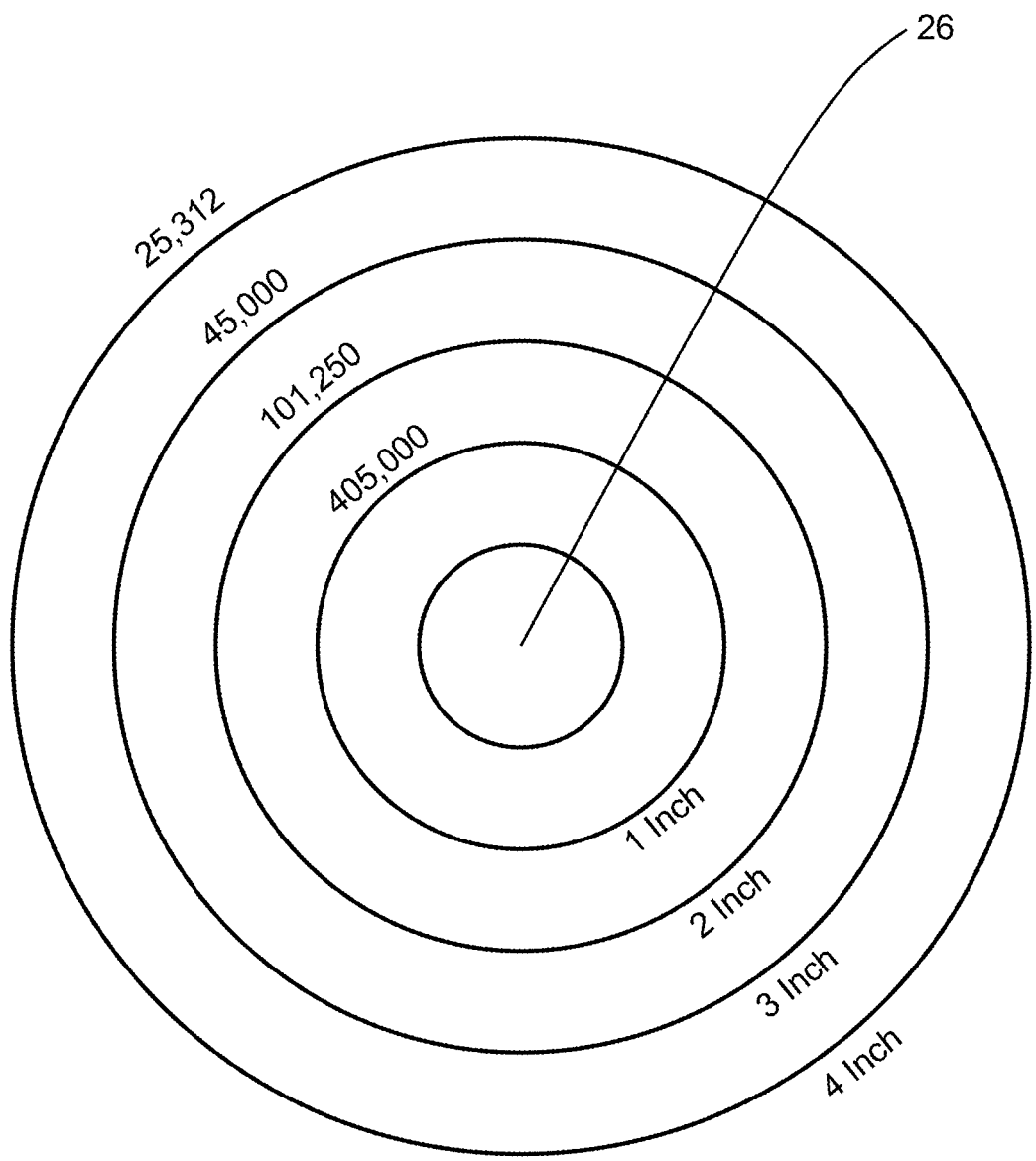
FIG. 24 is a chart illustrating the intensity of ultraviolet light radiation at a distance from the center of the bulb according to an embodiment of the present invention.

FIG. 24 is a chart illustrating how the intensity of UV-C light radiation decreases for specific distances away from UV-C bulb 26. FIG. 25 is a table showing how the intensity of UV-C light radiation decreases for specific distances away from UV-C bulb 26 and the disinfection or sterilization time for the air at a given distance from UV-C bulb 26. The last column of the table depicts the percentage of disinfection or sterilization for air flow at five inches per second for one inch of travel. Both the chart and table illustrate how fast the intensity of the UV-C radiation decreases the further away from the UV-C bulb 26. Any absorption of the UV-C radiation by any UV-C fixture will decrease the intensity of the radiation away from the lamp even further thus requiring more fixtures in a given area as dictated by the prior art. The chart and table also indicate how important air flow through sterilization chamber 104 and around bulb 26 is to adequately disinfect or sterilize the air. The present invention enables air flow to enter fixture 10, 200, 300, from all 360 degrees thereby ensuring more air flow will enter sterilization chamber 104 then any of the prior art that disclose wall mounted fixtures or fixtures having small gaps to allow airflow around the UV-C bulb. The present invention also limits the amount of UV-C radiation being absorbed by the fixture 10, 200, 300 itself thus enabling a broader sterilization field 132 outside fixture 10, 200, 300 than any of the prior art fixtures. The present invention will enable more sterilization in a room having a given size with a lower number of fixtures and, therefore, less cost than any of the prior art fixtures.

The present invention has been particularly shown and described with reference to the foregoing embodiments, which are merely illustrative of the best modes presently known for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method within the scope of these claims and their equivalents be covered thereby. This description of the invention should be understood to include all novel and non-obvious combination of elements described herein, and claims may be presented in this or a later application to any novel non-obvious combination of these elements. Moreover, the foregoing embodiments are illustrative, and no single feature or element is essential to all possible combinations that may be claimed in this or a later application.

What is claimed is:
1. An ultraviolet light fixture comprising:
at least one ultraviolet light bulb to sterilize an air flow;
an ultraviolet radiation field created by said at least one ultraviolet light bulb to sterilize the air flow;
a top end cap;
a base; and a plurality of louvers, said plurality of louvers positioned proximate one another, said top end cap and said base to create a gap, said gap sized to allow ultraviolet radiation to pass outside said ultraviolet light fixture to create a sterilization field outside said ultraviolet light fixture to eradicate bacterial, viral or pathogen particles from the air flow surrounding the fixture and said gap sized to allow passage of the air flow containing a cloud of infectious bacterial, viral or pathogen particles to pass through a sterilization chamber within said ultraviolet light fixture to eradicate bacterial, viral or pathogen particles from the air flow;

wherein said base includes:

at least one pillar, said pillar including a first male peg; and a first aperture; said first aperture sized to allow passage of said at least one ultraviolet light bulb.

2. The ultraviolet light fixture as recited in claim 1, wherein said top end cap includes a plurality of first female posts.

3. The ultraviolet light fixture as recited in claim 2, wherein said plurality of louvers each include:

a plurality of second male pegs;

a plurality of second female posts; and a second aperture; said second aperture sized to allow passage of said at least one ultraviolet light bulb.

4. The ultraviolet light fixture as recited in claim 3, wherein said plurality of second male pegs of plurality of said louvers are sized to nest within said plurality of first female posts of said top end cap and said plurality of second male pegs of plurality of said louvers are sized to nest within said plurality of second female posts of said plurality of louvers.

5. The ultraviolet light fixture as recited in claim 3, wherein said first male peg of said base is sized to nest within said second female post of said plurality of louvers.

6. The ultraviolet light fixture as recited in claim 3, wherein said ultraviolet light fixture includes a sleeve, said sleeve sized to change the size of said gap.

7. The ultraviolet light fixture as recited in claim 1, wherein said ultraviolet light fixture includes at least one dowel to secure said top end cap, said base and said plurality of louvers together.

8. The ultraviolet light fixture as recited in claim 1, wherein said ultraviolet light fixture includes a hinge.

9. The ultraviolet light fixture as recited in claim 1, wherein said ultraviolet bulb is secured in a vertical position relative to said ultraviolet light fixture and a ceiling in an area.

10. The ultraviolet light fixture as recited in claim 1, wherein said ultraviolet bulb operates at a wavelength of 200 nanometers to 280 nanometers.

11. An ultraviolet light fixture comprising:

at least one ultraviolet light bulb to sterilize an air flow, said ultraviolet light bulb secured in a vertical position relative to said ultraviolet light fixture and a ceiling in an area;

an ultraviolet radiation field created by said at least one ultraviolet light bulb to sterilize the air flow;

a top end cap, said top end cap including a plurality of first female posts;

a base, said base including at least one pillar, said pillar including:

a first male peg; and a first aperture; said first aperture sized to allow passage of said at least one ultraviolet light bulb;

a plurality of louvers, said plurality of louvers each including:

a plurality of second male pegs;

a plurality of second female posts; and a second aperture; said second aperture sized to allow passage of said at least one ultraviolet light bulb; and wherein said plurality of louvers are positioned proximate one another, said top end cap and said base to create a gap, said gap sized to allow ultraviolet radiation to pass outside said ultraviolet light fixture to create a sterilization field outside said ultraviolet light fixture to eradicate bacterial, viral or pathogen particles from the air flow surrounding the fixture and said gap sized to allow passage of the air flow containing a cloud of infectious bacterial, viral or pathogen particles to pass through a sterilization chamber within said ultraviolet light fixture to eradicate bacterial, viral or pathogen particles from the air flow.

12. The ultraviolet light fixture as recited in claim 11, wherein said plurality of second male pegs of plurality of said louvers are sized to nest within said plurality of first female posts of said top end cap and said plurality of second male pegs of plurality of said louvers are sized to nest within said plurality of second female posts of said plurality of louvers.

13. The ultraviolet light fixture as recited in claim 11, wherein said first male peg of said base is sized to nest within said second female post of said plurality of louvers.

14. The ultraviolet light fixture as recited in claim 11, wherein said ultraviolet light fixture includes a sleeve, said sleeve sized to change the size of said gap.

15. The ultraviolet light fixture as recited in claim 11, wherein said ultraviolet light fixture includes at least one dowel to secure said top end cap, said base and said plurality of louvers together.

16. The ultraviolet light fixture as recited in claim 11, wherein said ultraviolet light fixture includes a hinge.

17. The ultraviolet light fixture as recited in claim 11, wherein said ultraviolet bulb operates at a wavelength of 200 nanometers to 280 nanometers.

* * * * *